US012663401B2

(12) United States Patent
Bauer

(10) Patent No.: US 12,663,401 B2
(45) Date of Patent: Jun. 23, 2026

(54) REAL-TIME PREDICTION OF TISSUE FIXATION TIME

(71) Applicant: Ventana Medical Systems, Inc.,
Tucson, AZ (US)

(72) Inventor: Daniel R. Bauer, Tucson, AZ (US)

(73) Assignee: Ventana Medical Systems, Inc.,
Tucson, AZ (US)

( * ) Notice: Subject to any disclaimer, the term of this
patent is extended or adjusted under 35
U.S.C. 154(b) by 319 days.

(21) Appl. No.: 18/386,539

(22) Filed: Nov. 2, 2023

(65) Prior Publication Data

US 2024/0077456 A1 Mar. 7, 2024

Related U.S. Application Data

(63) Continuation of application No.
PCT/EP2022/062751, filed on May 11, 2022.
(Continued)

(51) Int. Cl.
*G01N 29/07* (2006.01)
*A61B 8/00* (2006.01)
(Continued)

(52) U.S. Cl.
CPC .............. *G01N 29/07* (2013.01); *G01N 1/30*
(2013.01); *A61B 8/5223* (2013.01);
(Continued)

(58) Field of Classification Search
CPC .... G01N 29/07; G01N 1/30; G01N 2291/011;
G01N 2291/0256; G01N 2291/02475;
(Continued)

(56) References Cited

U.S. PATENT DOCUMENTS

2003/0219719 A1* 11/2003 Bowman ................ A61B 5/413
703/11
2017/0336363 A1 11/2017 Bauer et al.
(Continued)

FOREIGN PATENT DOCUMENTS

JP 2018509599 A 4/2018
JP 2020502259 A 1/2020
(Continued)

OTHER PUBLICATIONS

International Preliminary Report on Patentability for PCT/EP2022/
062751, dated Nov. 14, 2023.
(Continued)

*Primary Examiner* — Peter J Macchiarolo
*Assistant Examiner* — John M Royston
(74) *Attorney, Agent, or Firm* — Charney IP Law LLC;
Thomas M. Finetti

(57) ABSTRACT

The present disclosure provides systems and methods which
facilitate the prediction of an estimated time in which one or
more fluids will optimally be diffused into a biological
specimen, e.g., a tissue sample derived from a human
subject. In some embodiments, the present disclosure pro-
vides systems and methods which facilitate the prediction of
an estimated time until a biological specimen will optimally
be fixed with one or more fixatives. In other embodiments,
the prediction of a future time at which the biological
specimen will be optimally fixed is based on time-of-flight
data acquired at a particular point in time during the fixation
of the biological specimen that has been deemed sufficiently
accurate to predict the time at which the biological specimen
will be optimally diffused with fixative.

20 Claims, 28 Drawing Sheets

401 — Acquire Acoustic Data Through At Least a Portion of a Biological Specimen

402 — Generate TOF Data Based on the Acquired Acoustic Data

403 — Compute At Least Two Different Confidence Models Based on the Generated TOF Data 404 — Assess Whether At Least Two of the Confidence Models Meet Predetermined Threshold Criteria 405 — Calculate the Time at Which the Biological Specimen will Ideally be Fixed

Related U.S. Application Data

(60) Provisional application No. 63/187,976, filed on May 13, 2021.

(51) Int. Cl.
*G01N 1/30* (2006.01)
*G01N 29/024* (2006.01)
*G01N 29/44* (2006.01)

(52) U.S. Cl.
CPC ....... *G01N 29/024* (2013.01); *G01N 29/4427* (2013.01); *G01N 29/4472* (2013.01); *G01N 2291/011* (2013.01); *G01N 2291/02475* (2013.01); *G01N 2291/0256* (2013.01)

(58) Field of Classification Search
CPC ........... G01N 29/4427; G01N 29/4472; G01N 29/024; A61B 8/5223
USPC .......................................................... 73/597
See application file for complete search history.

(56) References Cited

U.S. PATENT DOCUMENTS

| | | | |
|---|---|---|---|
| 2019/0293525 | A1 | 9/2019 | Bauer et al. |
| 2019/0310169 | A1 | 10/2019 | Bauer et al. |
| 2022/0034845 | A1 | 2/2022 | Bauer et al. |
| 2023/0204470 | A1 | 6/2023 | Bauer et al. |
| 2023/0213416 | A1 | 7/2023 | Bauer et al. |

FOREIGN PATENT DOCUMENTS

| | | | |
|---|---|---|---|
| WO | 2016128299 | A1 | 8/2016 |
| WO | 2016129299 | A1 | 8/2016 |
| WO | 2018119189 | A1 | 6/2018 |
| WO | 2018119194 | A1 | 6/2018 |

OTHER PUBLICATIONS

International Search Report and Written Opinion for PCT/EP2022/062751, mailed on Oct. 12, 2022.

* cited by examiner

101 Receive Time-of-flight (ToF) Data Across One or More Positions Within a Tissue Sample 102 In Real-time, Determine if the Received ToF Data is Valid 105 Predict a Diffusion Time of Fixative into the Tissue Sample Once it is Determined that the ToF Data is Valid

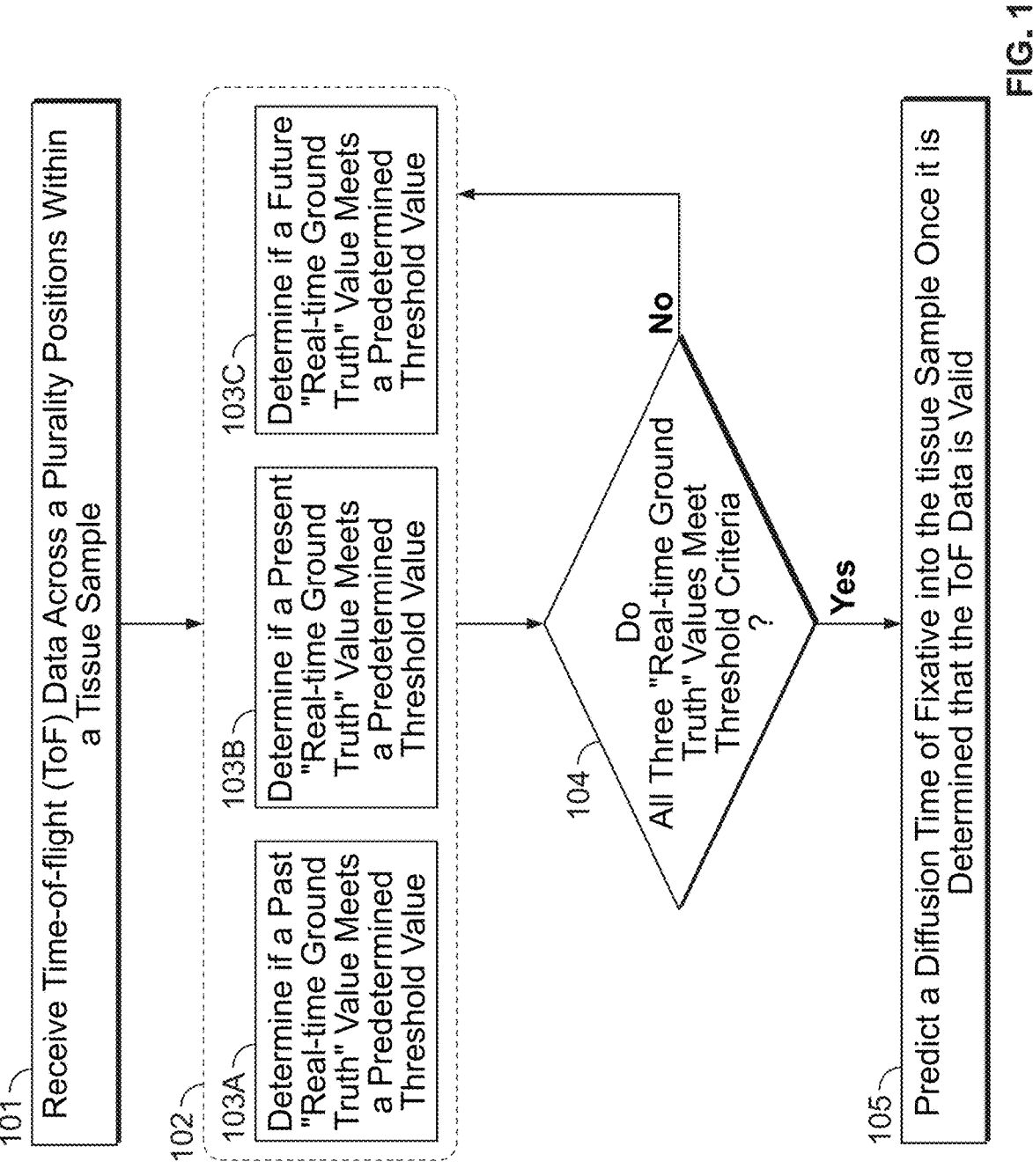

101  Receive Time-of-flight (ToF) Data Across a Plurality Positions Within a Tissue Sample

102

103A  Determine if a Past "Real-time Ground Truth" Value Meets a Predetermined Threshold Value 103B  Determine if a Present "Real-time Ground Truth" Value Meets a Predetermined Threshold Value 103C  Determine if a Future "Real-time Ground Truth" Value Meets a Predetermined Threshold Value 104  Do All Three "Real-time Ground Truth" Values Meet Threshold Criteria ?

No

Yes

105  Predict a Diffusion Time of Fixative into the tissue Sample Once it is Determined that the ToF Data is Valid

FIG. 1B

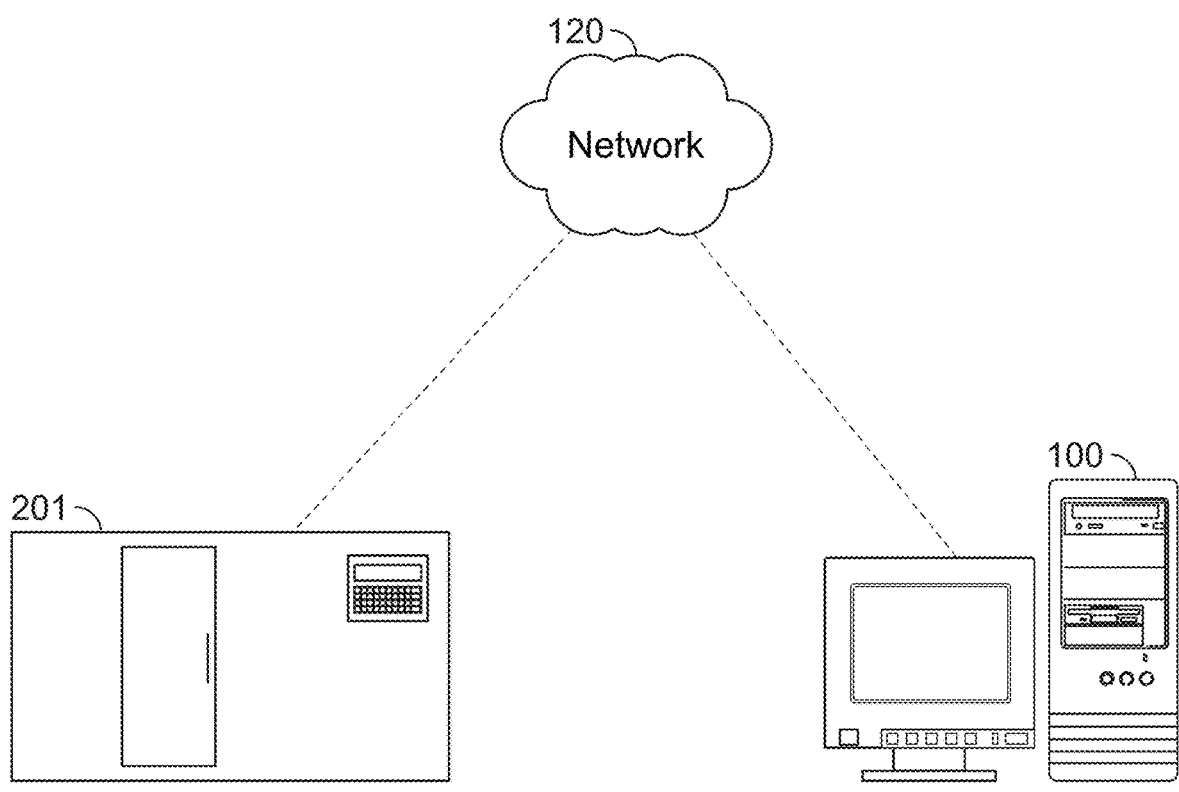
FIG. 2

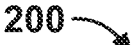
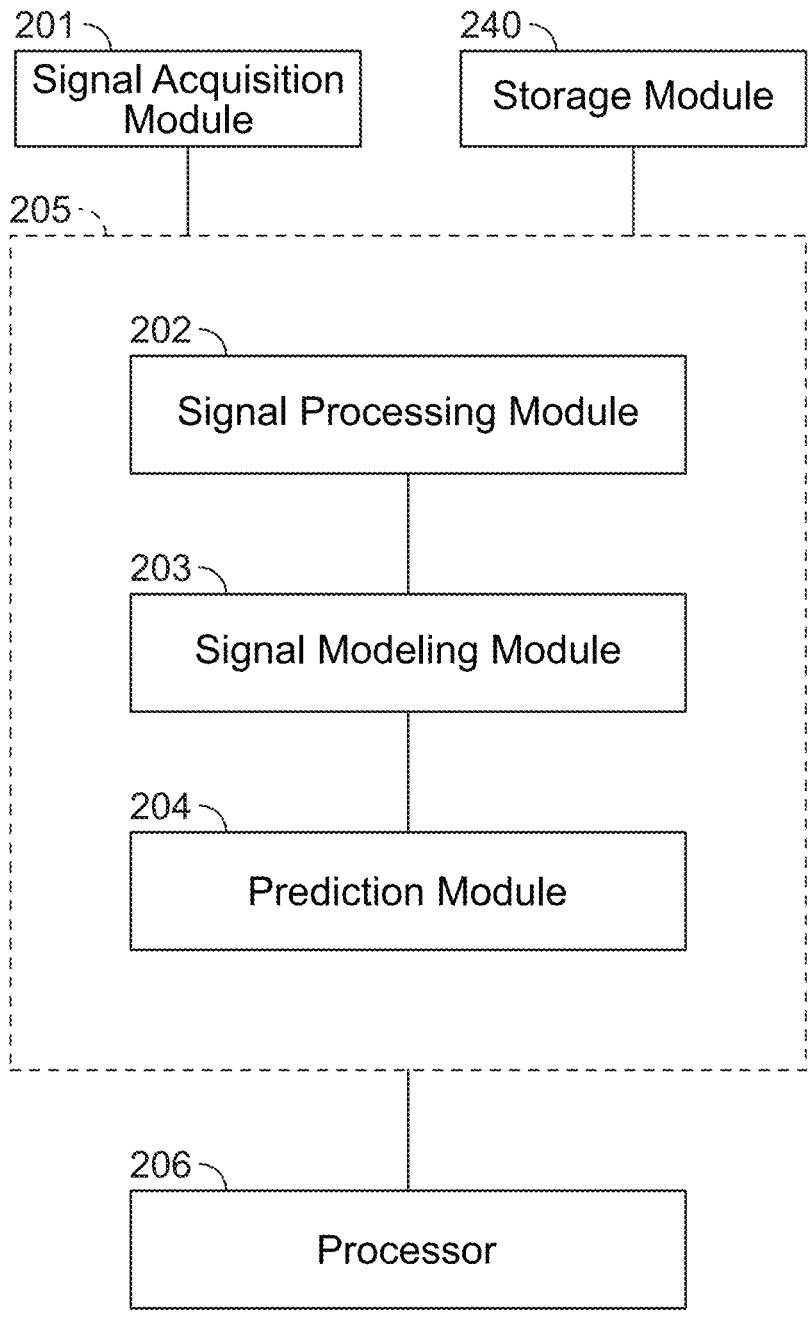
FIG. 3

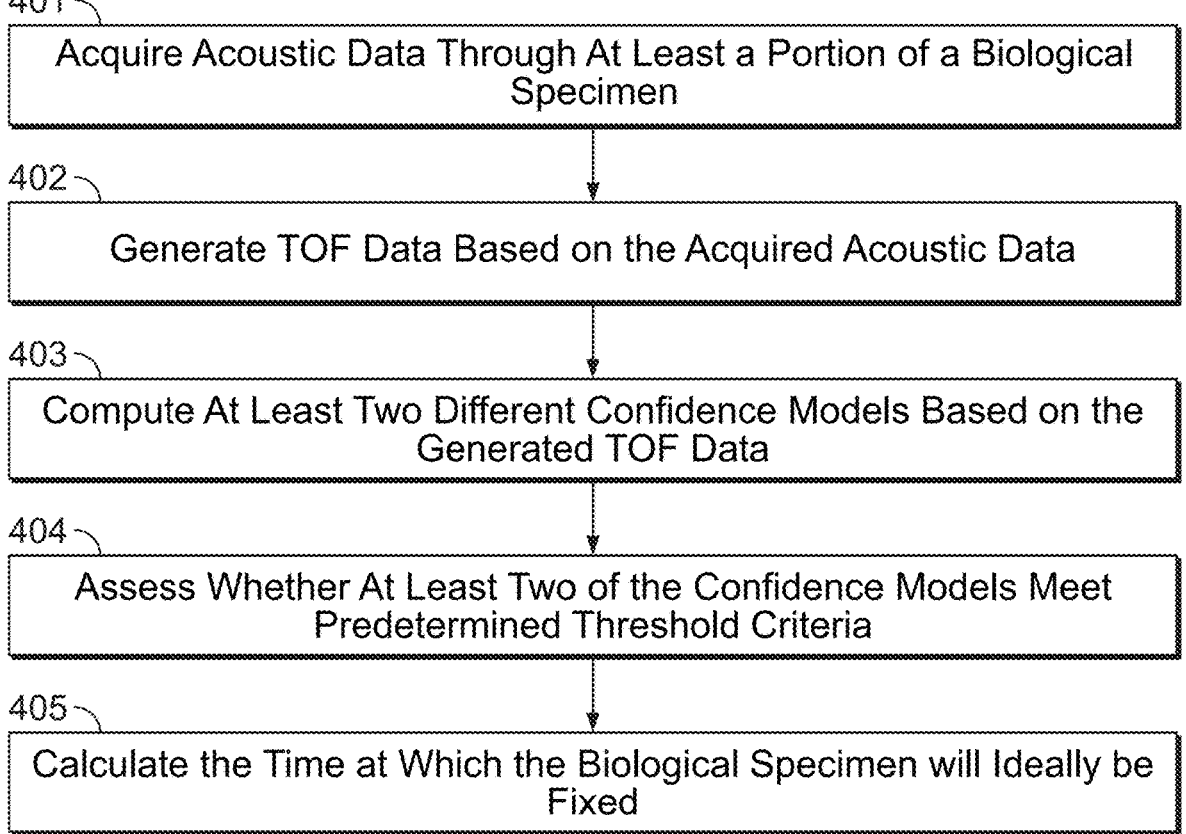

401 — Acquire Acoustic Data Through At Least a Portion of a Biological Specimen

402 — Generate TOF Data Based on the Acquired Acoustic Data

403 — Compute At Least Two Different Confidence Models Based on the Generated TOF Data 404 — Assess Whether At Least Two of the Confidence Models Meet Predetermined Threshold Criteria 405 — Calculate the Time at Which the Biological Specimen will Ideally be Fixed

FIG. 4

$$TOF\ (t) = C + Ae^{-t/\tau}$$

95% CI

±0.44 ns

95% CI

±7 min

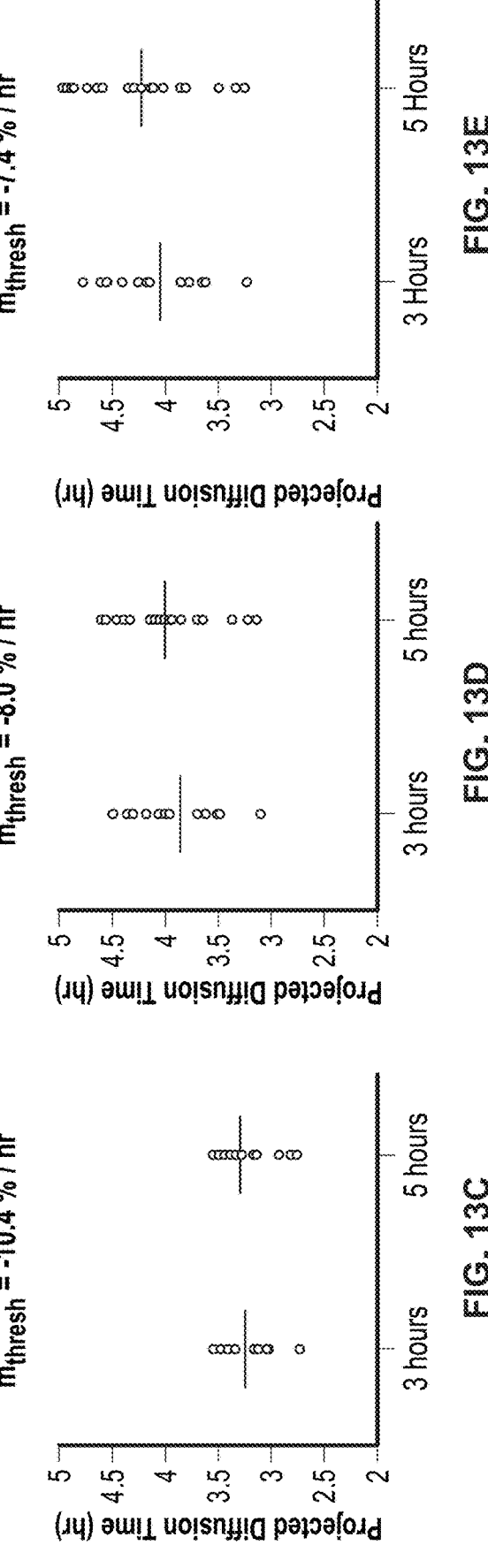

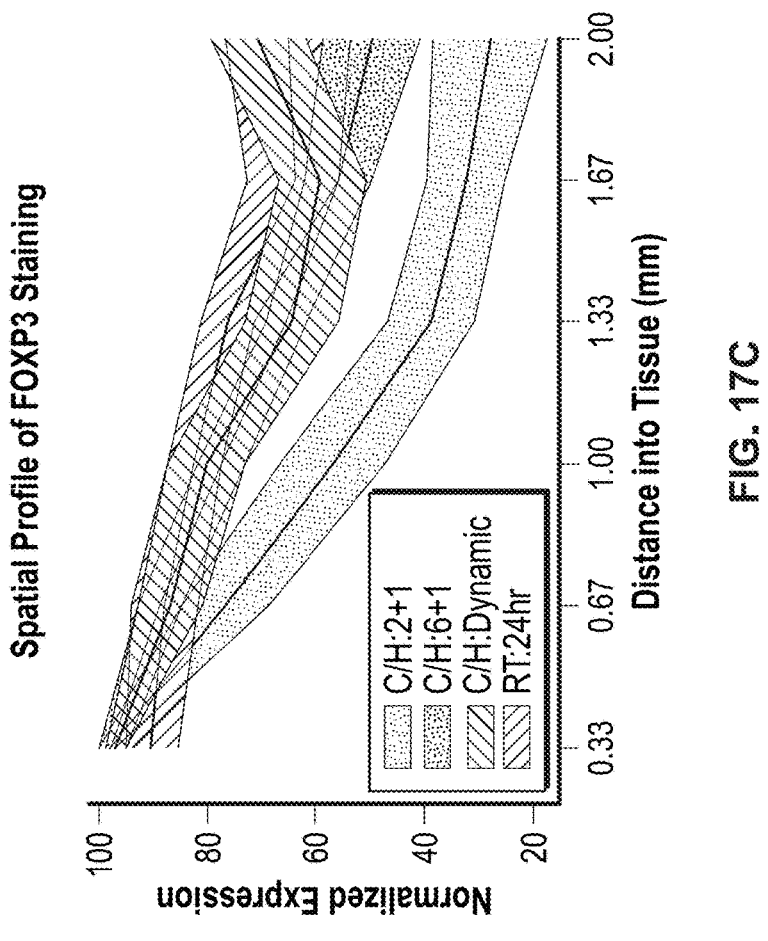
FIG. 17C
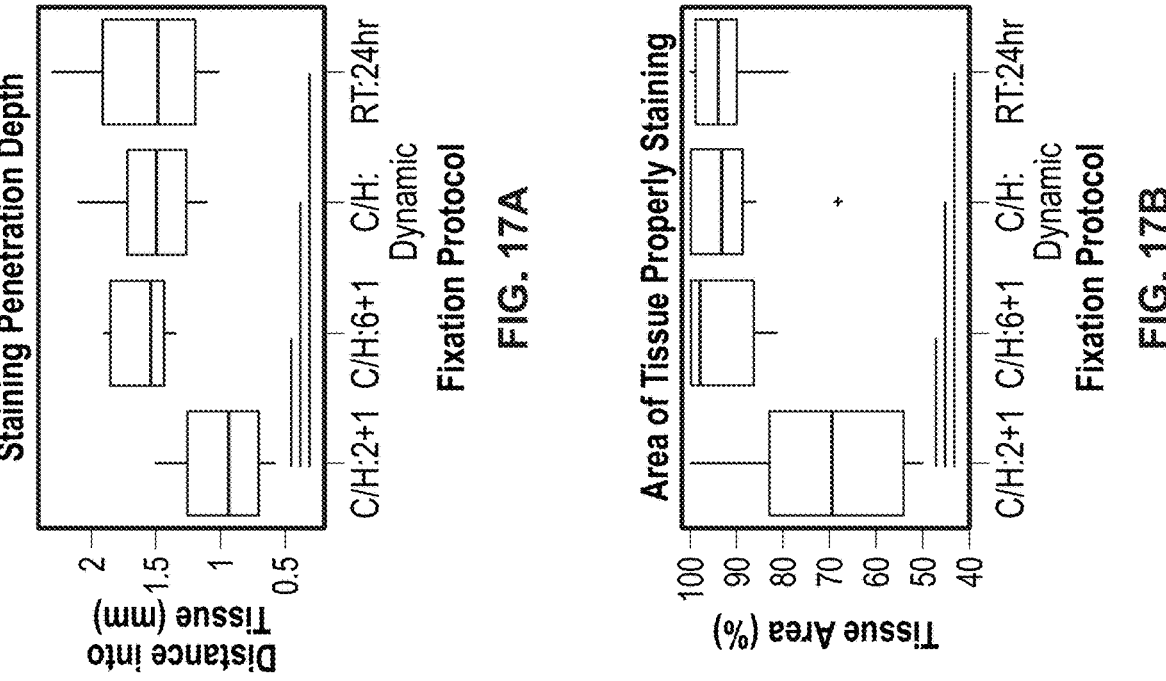
FIG. 17A
FIG. 17B

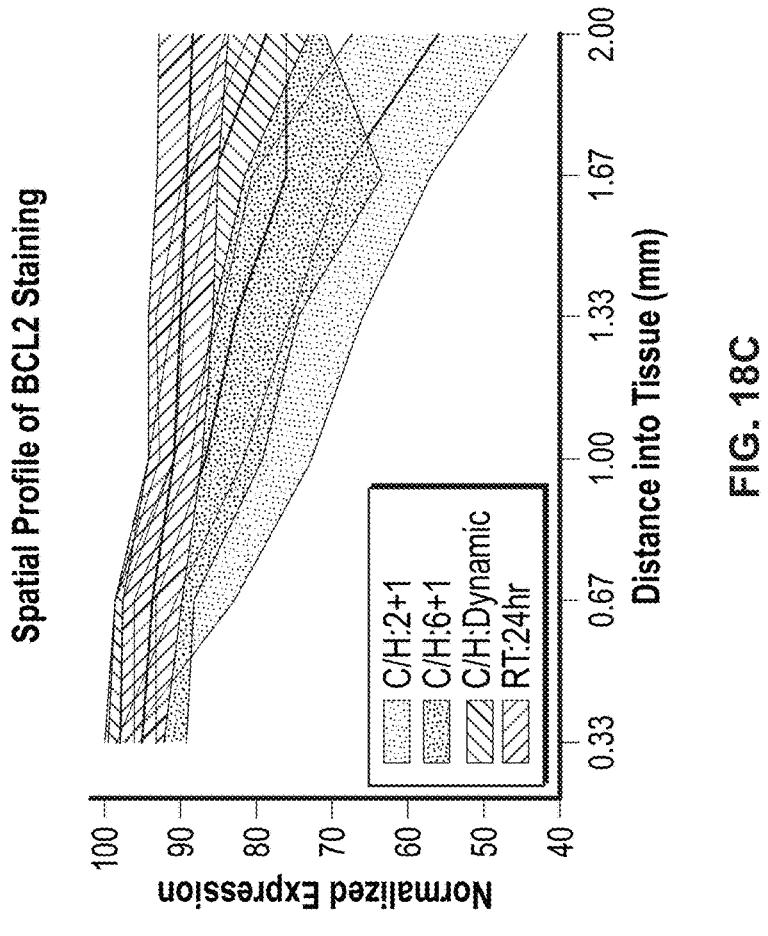
FIG. 18C
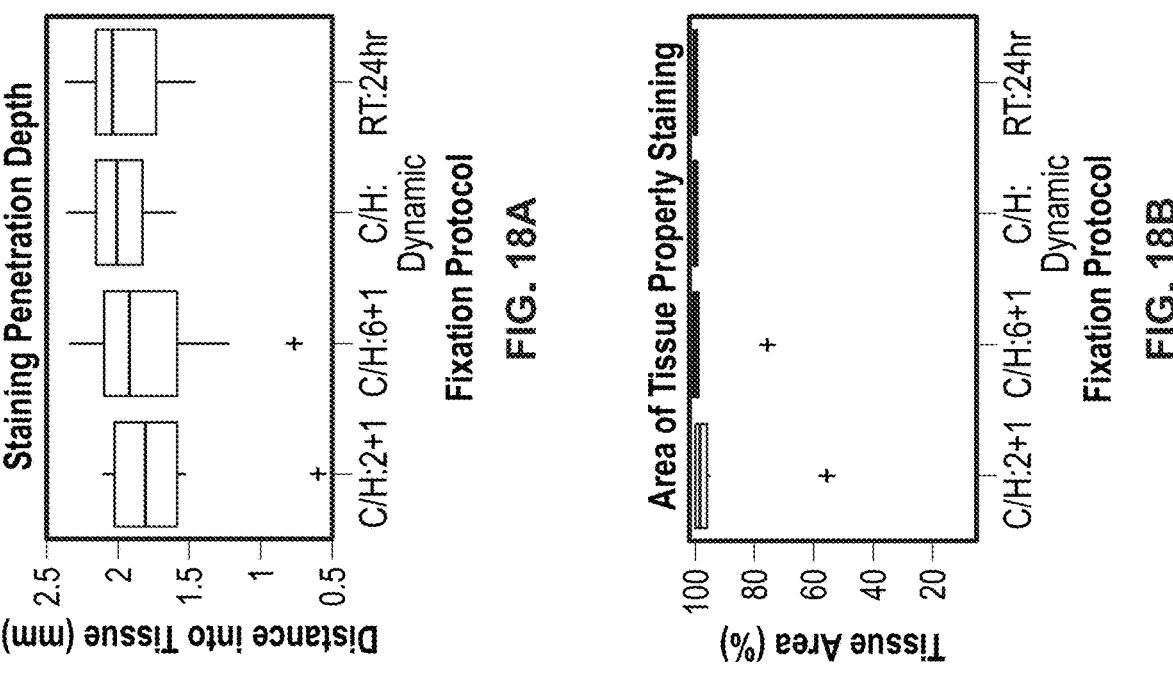
FIG. 18A
FIG. 18B

Past Algorithm Flowchart

REAL-TIME PREDICTION OF TISSUE FIXATION TIME

CROSS REFERENCE TO RELATED APPLICATIONS

The present application claims the benefit of the filing date of International Patent Application No. PCT/EP2022/062751 filed on May 11, 2022, which application claims the benefit of the filing date of U.S. Provisional Patent Application No. 63/187,976 filed on May 13, 2021, the disclosure of which is hereby incorporated by reference herein in its entirety.

BACKGROUND OF THE DISCLOSURE

Proper medical diagnosis and patient safety require properly fixing tissue samples prior to staining. Accordingly, guidelines have been established by oncologists and pathologists for proper fixation of tissue samples. For example, according to the American Society of Clinical Oncology (ASCO), the current guideline for fixation duration in neutral buffered formalin solution for HER2 immunohistochemistry analysis is at least 6 hours, preferably more, and up to 72 hours.

Several effects are observed in tissues that are either under exposed or over exposed to formalin. If a tissue sample is not treated with formalin for a sufficiently long period of time, tissue morphology is typically very poor when the tissues are subjected to standard tissue processing. For example, in inadequately fixed tissue, subsequent exposure to ethanol shrinks the cellular structures and condenses nuclei since the tissues will not have the chance to form a proper cross-linked lattice. When under fixed tissue is stained, such as with hematoxylin and eosin (H&E), many white spaces are observed in between the cells and tissue structures, condensed nuclei and loss of cytoplasm, and samples appear pink and unbalanced with the hematoxylin stain. Tissues that have been exposed to a fixative, such as formalin, for too long of a time period typically do not work well for subsequent immunohistochemical processes, presumably because of nucleic acid and/or protein denaturation and degradation. As a result, the optimal antigen retrieval conditions for these tissues do not work properly and therefore the tissue samples appear to be under stained.

Monitoring diffusion of fixatives through a tissue sample is useful for determining whether the fixative has infused the entire tissue sample, thereby minimizing, or limiting under-fixed tissue or over-fixed tissue. If, for example, the tissue is "over-fixed," it may be difficult to diffuse processing liquids through the tissue due to an overly extensive network of cross-linked molecules that limit paths for diffusion. On the other hand, if the tissue is under-fixed, the tissue may be degraded, for example, by autocatalytic destruction, leading to loss of tissue and cellular morphology as well as loss of protein and nucleic acid markers of diagnostic significance. Algorithms have been utilized to determine how diffused with the fixative a biological specimen must be in order to be properly fixed and therefore to ensure proper and ideal staining. For instance, U.S. Pat. No. 10,620,037 (the disclosure of which is hereby incorporated by reference herein in its entirety) describes systems and computer-implemented methods for calculating the diffusivity constant (i.e., diffusivity coefficient) of a sample using acoustic time-of-flight (TOF) based information correlated with a diffusion model to reconstruct a biological specimen's diffusivity coefficient. The '037 patent further describes a method for determining a true diffusivity constant for a biological specimen immersed within a fluid, the method including simulating a spatial dependence of a diffusion into the sample over a plurality of time points and for each of a plurality of candidate diffusivity constants to generate a model TOF, and comparing the model TOF with an experimental TOF to obtain an error function, wherein a minimum of the error function yields the true diffusivity constant.

By way of another example, PCT Publication No. WO/2016/097164 (the disclosure of which is hereby incorporated by reference herein in its entirety) describes a computer-implemented method for accurately calculating the TOF of an acoustic signal traversing through a material (e.g., a biological specimen) including obtaining an error function of a frequency sweep of the acoustic signal, and generating an envelope of the error function, wherein the time-of-flight is based on a minimum of the error function. For instance, the '164 Publication describes computing a TOF of acoustic waves by one of three methods, namely (1) calculating an envelope for an error function enabling a more accurate determination of a minimum of the error function; (2) fitting ultrasound frequency sweep data to a plurality of simulated TOF frequency sweeps, with the TOF being calculated directly from the best fit; and/or (3) performing a linear regression analysis on individual linear parts of the ultrasonic frequency sweep, enabling identification of abnormal sections of the frequency sweep that may represent errors in the TOF calculation.

A rate of diffusion of fixative through a tissue specimen can change significantly throughout an experiment as data points are continually collected. This variability is due partially from the noise inherent in TOF systems but also from the variability inherit to the tissue specimen (e.g., sporadic diffusion, tissue deformation, etc.) which masks the true diffusion signal of the tissue specimens. It would be desirable to have a model which is able to predict in real-time whether a TOF signal is sufficiently valid such the TOF data may be used to determine a time to fixation of a tissue specimen.

BRIEF SUMMARY OF THE DISCLOSURE

Variations in the fixation of a biological specimen, e.g., a tissue sample or a cytological sample, may impact downstream biomarker labeling and/or staining processes, which may result in inconclusive results and/or a misdiagnosis. Therefore, it would be advantageous to have a system and/or method which facilitates the determination of whether a biological specimen has been adequately fixed such that downstream staining and/or labeling processes may be performed on an adequately fixed specimen.

Applicant has developed systems and methods which facilitate the determination of whether a measured TOF signal accurately reflects the actual rate of diffusion of a fluid, reagent, or solution (hereinafter collectively referred to as a "fluid") through a biological specimen. As such, the present disclosure provides systems and methods which facilitate the prediction of an estimated time in which a fluid will be optimally be diffused into a biological specimen, for example, the time it will take for a particular fluid to reach a particular concentration at a particular location in the biological specimen, such as a center region of the biological specimen. In some embodiments, the fluid includes one or more fixatives (including any of those described herein). In other embodiments, the fluid includes dehydrating reagents (such as graded ethanols), clearing agents (such as xylene), and paraffin used for embedding of a biological specimen.

Yet other fluids are described further herein. While certain embodiments of the present disclosure may describe estimating a time in which a biological specimen may be optimally fixed when immersed in one or more fixatives, the present disclosure is applicable to predicting a time in which any fluid (e.g., ethanol, xylene, paraffin) is optimally diffused into a biological specimen.

In some embodiments, the systems and methods analyze components of an obtained TOF signal to determine whether the obtained TOF signal is deemed sufficiently accurate such that a time in which a fluid is optimally diffused into a biological specimen may be predicted. In the context of fixing a biological specimen with one or more fixatives, in some embodiments the systems and methods analyze different components of an obtained TOF signal to determine whether the obtained TOF signal is deemed sufficiently accurate to predict the time at which the biological specimen will be optimally diffused with the one or more fixatives, e.g., a time needed to achieve a certain concentration or amount of the one or more fixatives within or throughout the biological specimen, such as at a center of the biological specimen.

In view of the foregoing, at least some of the embodiments of the present disclosure relate to systems and methods for acquiring TOF data through a biological specimen (such as one included in a container, such as a biopsy capsule or a biopsy cassette) and analyzing the acquired TOF data, such as in real-time. In some embodiments, the acquired TOF data is analyzed to determine whether acquired TOF data at a particular point in time is sufficiently accurate such that the TOF data at that particular point in time may be used to compute a time in which a fluid will optimally be diffused into a biological specimen or a time in which a biological specimen will be optimally fixed (such as with one or more of the fixatives described herein).

In view of the foregoing, one aspect of the present disclosure is a method of estimating a time in which a fluid will ideally be diffused into or throughout a biological specimen immersed in the fluid, comprising: acquiring acoustic data at one or more positions along the biological specimen immersed in the fluid; deriving time-of-flight (TOF) data from the acquired acoustic data, wherein the derived TOF data comprises one or more computed TOF data points, one or more computed TOF curves, and/or one or more computed decay constants; simultaneously computing at least two confidence models based on the derived TOF data (e.g., wherein the at least two confidence models comprise a past confidence model, a present confidence model, and/or a future confidence model); determining a point in time when the computed at least two confidence models each independently meet predetermined threshold criteria; and estimating the time in which the fluid will ideally be diffused into the biological specimen based on TOF data corresponding to the determined point in time when the computed at least two of confidence models each independently met the predetermined threshold criteria.

In some embodiments, the fluid comprises one or more fixatives. In some embodiments, the one or more fixatives are aldehyde-based fixatives. In some embodiments, the fluid is selected from the group consisting of ethanol, xylene, and paraffin.

In some embodiments, the computed at least two confidence models include the past confidence model and the present confidence model. In some embodiments, the computed at least two confidence models include each of the past confidence model, the present confidence model, and the future confidence model.

In some embodiments, the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant. In some embodiments, the determination of whether the predetermined number of retrieved computed candidate decay constants are within the predetermined threshold percentage value of the calculated average decay constant comprises performing convergence testing. In some embodiments, the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value. In some embodiments, the average decay constant is derived by: (i) retrieving a computed a decay constant for each of a predetermined number of TOF data points preceding the candidate TOF data point; and (ii) averaging each of the retrieved computed decay constants. In some embodiments, the predetermined number of TOF data points preceding the candidate TOF data point is at least about 3. In some embodiments, the predetermined threshold percentage value is less than about 5%. In some embodiments, the predetermined threshold percentage value is less than about 2.5%.

In some embodiments, the computed present confidence model meets predetermined present confidence model threshold criteria when a calculated present confidence interval is below a predetermined present confidence model threshold value. In some embodiments, the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

In some embodiments, the computed future confidence model meets predetermined future confidence model threshold criteria when a calculated future confidence interval is below a predetermined future confidence model threshold value. In some embodiments, the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

In some embodiments, the method further comprises staining the biological specimen for the presence of at least one biomarker. In some embodiments, the at least one biomarker is a cancer biomarker.

In some embodiments, the method further comprises scoring the biological specimen stained for the presence of the at least one biomarker.

In some embodiments, the method further comprises staining the biological specimen for the presence of at least two biomarkers. In some embodiments, a single serial section derived from the biological specimen is stained for the presence of the at least two biomarkers.

Another aspect of the present disclosure is a method of predicting a time to fixation completion of a biological specimen immersed in one or more fixatives, comprising: acquiring acoustic data at one or more positions along the biological specimen immersed in the one or more fixatives; deriving time-of-flight (TOF) data from the acquired acoustic data, wherein the derived TOF data comprises one or more computed TOF data points, one or more computed TOF curves, and/or one or more computed decay constants; simultaneously computing at least two confidence models based on the derived TOF data, wherein the at least two confidence models comprise a past confidence model, a present confidence model, and a future confidence model; determine a point in time when the computed at least two confidence models each independently meet predetermined threshold criteria; and predicting the time to fixation completion based on TOF data corresponding to the determined point in time when the computed at least two of confidence models each independently met the predetermined threshold criteria.

In some embodiments, the biological specimen is first immersed in one or more fixatives at a temperature below about 15° C., such as at 14° C. or below, at 13° C. or below, at 12° C. or below, at 11° C. or below, at 10° C. or below, at 9° C. or below, at 8° C. or below, at 7° C. or below, at 6° C. or below, at 5° C. or below, or at 4° C. or below. In some embodiments, the acoustic data is acquired after the one or more fixatives are warmed to (passively or actively) a temperature of greater than about 15° C., such as room temperature. In some embodiments, the acoustic data is acquired after the one or more fixatives are warmed to (passively or actively) a temperature of greater than about 25° C. In some embodiments, the acoustic data is acquired after the one or more fixatives are warmed to (passively or actively) a temperature of greater than about 35° C. In some embodiments, the acoustic data is acquired after the one or more fixatives are warmed to (passively or actively) a temperature of greater than about 45° C. In some embodiments, the acoustic data is acquired after the one or more fixatives are warmed to (passively or actively) a temperature between about 20° C. to about 50° C. In some embodiments, the acoustic data is acquired after the one or more fixatives are warmed to (passively or actively) a temperature between about 20° C. to about 45° C.

In some embodiments, the computed at least two confidence models include the past confidence model and the present confidence model. In some embodiments, the computed at least two confidence models include each of the past confidence model, the present confidence model, and the future confidence model.

In some embodiments, the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant. In some embodiments, the determination of whether the predetermined number of retrieved computed candidate decay constants are within the predetermined threshold percentage value of the calculated average decay constant comprises performing convergence testing. In some embodiments, the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value. In some embodiments, the average decay constant is derived by: (i) retrieving a computed a decay constant for each of a predetermined number of TOF data points preceding the candidate TOF data point; and (ii) averaging each of the retrieved computed decay constants. In some embodiments, the predetermined number of TOF data points preceding the candidate TOF data point is at least 3. In some embodiments, the predetermined threshold percentage value is less than about 5%. In some embodiments, the predetermined threshold percentage value is less than about 2.5%.

In some embodiments, the computed present confidence model meets predetermined present confidence model threshold criteria when a calculated present confidence interval is below a predetermined present confidence model threshold value. In some embodiments, the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

In some embodiments, the computed future confidence model meets predetermined future confidence model threshold criteria when a calculated future confidence interval is below a predetermined future confidence model threshold value. In some embodiments, the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

In some embodiments, the method further comprises staining the biological specimen for the presence of at least one biomarker. In some embodiments, the at least one biomarker is a cancer biomarker.

In some embodiments, the method further comprises scoring the biological specimen stained for the presence of the at least one biomarker, including any of the biomarkers enumerated herein.

In some embodiments, the method further comprises staining the biological specimen for the presence of at least two biomarkers. In some embodiments, a single serial section derived from the biological specimen is stained for the presence of the at least two biomarkers.

Another aspect of the present disclosure is a non-transitory computer-readable medium storing instructions for estimating a time in which a fluid will ideally be diffused into a biological specimen immersed in the fluid comprising: deriving time-of-flight (TOF) data from acquired acoustic data; simultaneously computing at least two confidence models based on the derived TOF data, wherein the at least two confidence models comprise a past confidence model, a present confidence model, and a future confidence model; determining a point in time when the computed at least two confidence models each independently meet predetermined threshold criteria; and estimating the time in which the fluid will ideally be diffused into the biological specimen based on TOF data corresponding to the determined point in time when the computed at least two of confidence models each independently met the predetermined threshold criteria.

In some embodiments, the method further comprises instructions for computing one or more decay constants. In some embodiments, the further comprising instructions for performing convergence testing. In some embodiments, the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value.

Another aspect of the present disclosure is a non-transitory computer-readable medium storing instructions for determining a point in time when at least two confidence models each independently meet predetermined threshold criteria comprising: (a) deriving TOF data from acoustic data acquired of a biological specimen immersed in a fluid; (b) continuously computing a past confidence model, a present confidence model, and a future confidence model until each of the past, present, and future confidence models simultaneously and independently meet predetermined threshold criteria; and (c) identifying the point in time corresponding to the derived TOF data at which the past, present, and future confidence models were simultaneously and independently satisfied. In some embodiments, the models are continuously computed as new data is received or acquired, which may occur between every about 0.2 seconds to about 120 seconds as described herein.

In some embodiments, the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant. In some embodiments, the determination of whether the predetermined number of retrieved computed candidate decay constants are within the predetermined threshold percentage value of the calculated average decay constant comprises performing convergence testing. In some embodiments, the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value. In some embodiments, the average decay constant is derived by: (i) retrieving a computed a decay constant for each of a predetermined number of TOF data points preceding the candidate TOF data point; and (ii) averaging each of the retrieved computed decay constants.

In some embodiments, the computed present confidence model meets predetermined present confidence model threshold criteria when a calculated present confidence interval is below a predetermined present confidence model threshold value. In some embodiments, the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

In some embodiments, the computed future confidence model meets predetermined future confidence model threshold criteria when a calculated future confidence interval is below a predetermined future confidence model threshold value. In some embodiments, the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

In some embodiments, the non-transitory computer readable medium further comprises instructions for estimate a time in which the fluid is ideally diffused into the biological specimen. In some embodiments, the fluid comprises one or more fixatives. In some embodiments, the fluid is selected from the group consisting of ethanol, xylene, and paraffin.

Another aspect of the present disclosure is a system for estimating a time in which a fluid will ideally be diffused into a biological specimen immersed in the fluid, the system comprising: (i) one or more processors, and (ii) one or more memories coupled to the one or more processors, the one or more memories to store computer-executable instructions that, when executed by the one or more processors, cause the system to perform operations comprising: deriving time-of-flight (TOF) data from acoustic data acquired at one or more positions along a biological specimen immersed in a fluid; simultaneously computing at least two confidence models based on the derived TOF data, wherein the at least two confidence models comprise a past confidence model, a present confidence model, and a future confidence model; determining a point in time when the computed at least two confidence models each independently meet predetermined threshold criteria; and estimating the time in which the fluid will ideally be diffused into the biological specimen based on TOF data corresponding to the determined point in time when the computed at least two of confidence models each independently met the predetermined threshold criteria.

In some embodiments, the fluid comprises one or more fixatives. In some embodiments, the fluid is selected from the group consisting of ethanol, xylene, and paraffin.

In some embodiments, the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant. In some embodiments, the determination of whether the predetermined number of retrieved computed candidate decay constants are within the predetermined threshold percentage value of the calculated average decay constant comprises performing convergence testing. In some embodiments, the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value. In some embodiments, the average decay constant is derived by: (i) retrieving a computed a decay constant for each of a predetermined number of TOF data points preceding the candidate TOF data point; and (ii) averaging each of the retrieved computed decay constants. In some embodiments, the predetermined number of TOF data points preceding the candidate TOF data point is at least 3. In some embodiments, the predetermined threshold percentage value is less than about 5%. In some embodiments, the predetermined threshold percentage value is less than about 2.5%.

In some embodiments, the computed present confidence model meets predetermined present confidence model threshold criteria when a calculated present confidence interval is below a predetermined present confidence model threshold value. In some embodiments, the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

In some embodiments, the computed future confidence model meets predetermined future confidence model threshold criteria when a calculated future confidence interval is below a predetermined future confidence model threshold value. In some embodiments, the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

Applicant has surprisingly discovered that the systems and methods of the present disclosure provide for an accurate prediction of a time to fixation of a biological specimen.

BRIEF DESCRIPTION OF THE FIGURES

For a general understanding of the features of the disclosure, reference is made to the drawings. In the drawings, like reference numerals have been used throughout to identify identical elements.

FIGS. 1A and 1B set forth flowcharts providing an overview of the steps of the present disclosed methods of predicting a diffusion time of a fluid (e.g., a fixative) into a biological specimen in accordance with one embodiment of the present disclosure.

FIG. 2 illustrates a representative digital pathology system including a computer system in accordance with some embodiments.

FIG. 3 sets forth various modules that can be utilized in a fluid diffusion and/or fixation prediction system in accordance with some embodiments.

FIG. 4 illustrates a method of calculating the time at which a biological specimen will be optimally fixed in accordance with one embodiment of the present disclosure.

Graph of each individual confidence model for all time points in the experiment with a high value indicating criterion is met and a low value indicating criterion is not met. All three criteria must be simultaneously satisfied for the TOF signal to be deemed representative of the tissue's actual diffusion profile. (Top graph is future confidence model, middle graph is past confidence model, bottom graph is present confidence model).

Figures 10A, 10B:
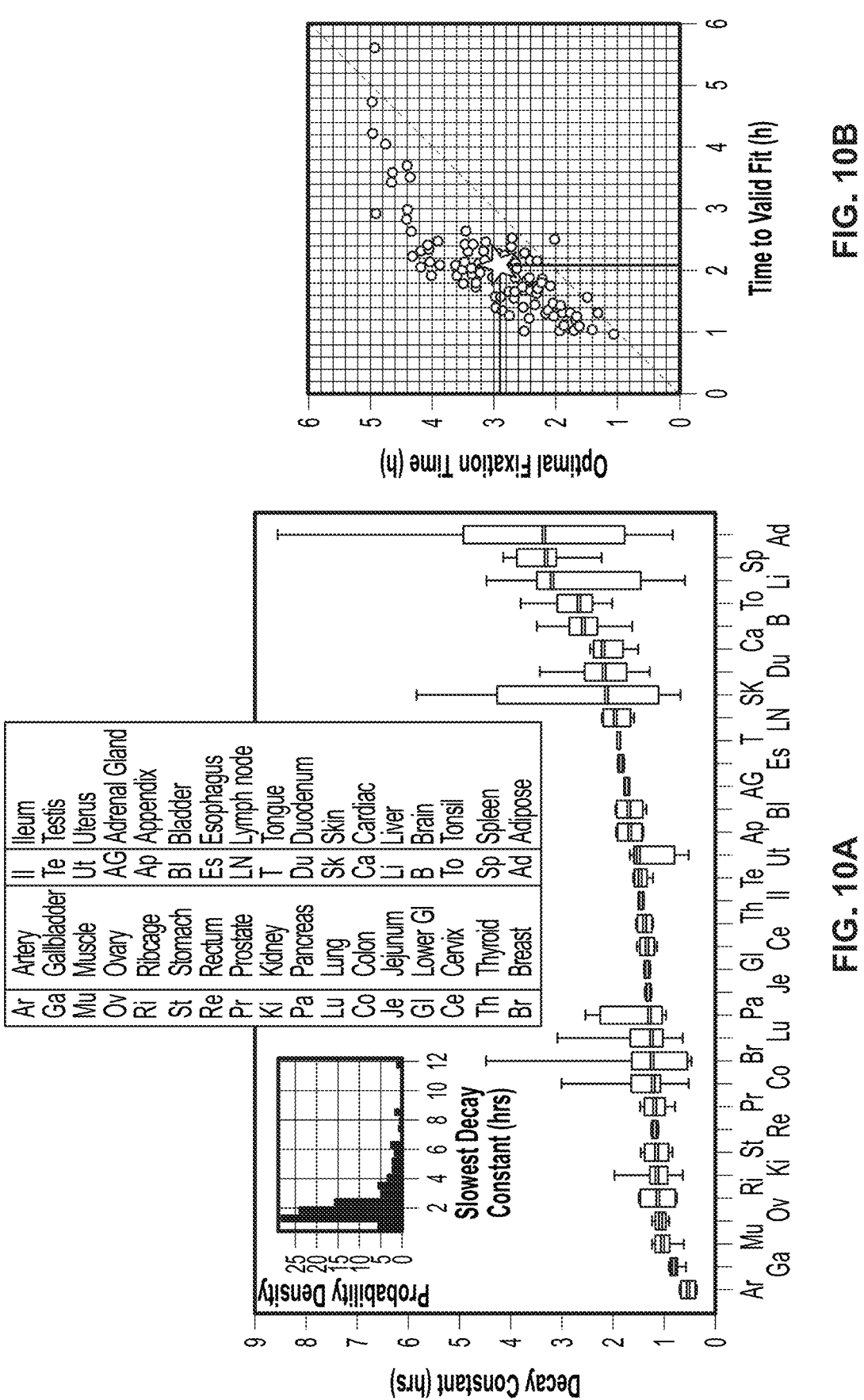

FIGS. 10A and 10B provide results from a TOF analysis. a) Distribution of TOF diffusion data for multiple tissue demonstrating the acoustic technology work across a multitude of tissue types. b) Cumulative results for criterion development in which 105 tissues across multiple types of tissue were analyzed with the presented method of determining when a TOF curve is valid. The time to a valid fit is plotted on the horizontal time versus the calculated optimal fixation time on the vertical axis.

Figure 11B:
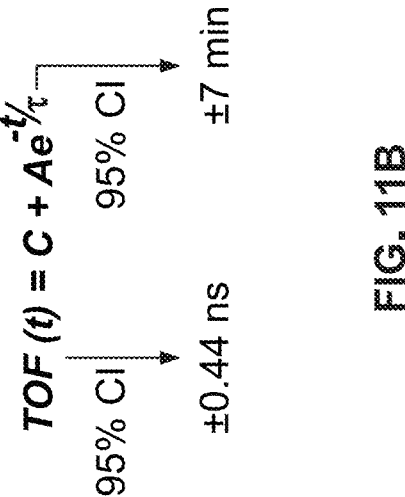
Figure 11A:
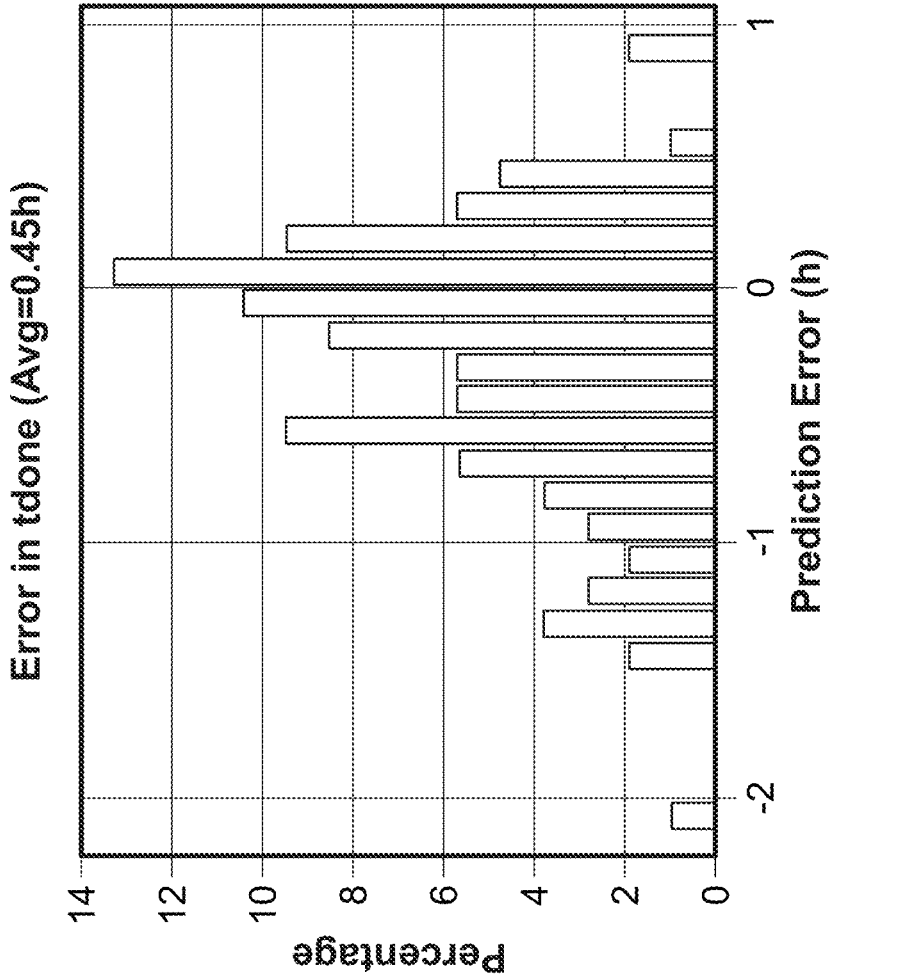

FIGS. 11A and 11B provide an analysis of the accuracy of the disclosed confidence models. a) Distribution of model's prediction error, calculated as the difference between the calculated optimal diffusion time at the time the signal was determined to be valid versus the end of the experiment. b) Average 95% confidence intervals for all 105 tissues in the study for the entire TOF signal as well as the decay constant at the time the signal was deemed valid by the model.

Figures 12A, 12B:
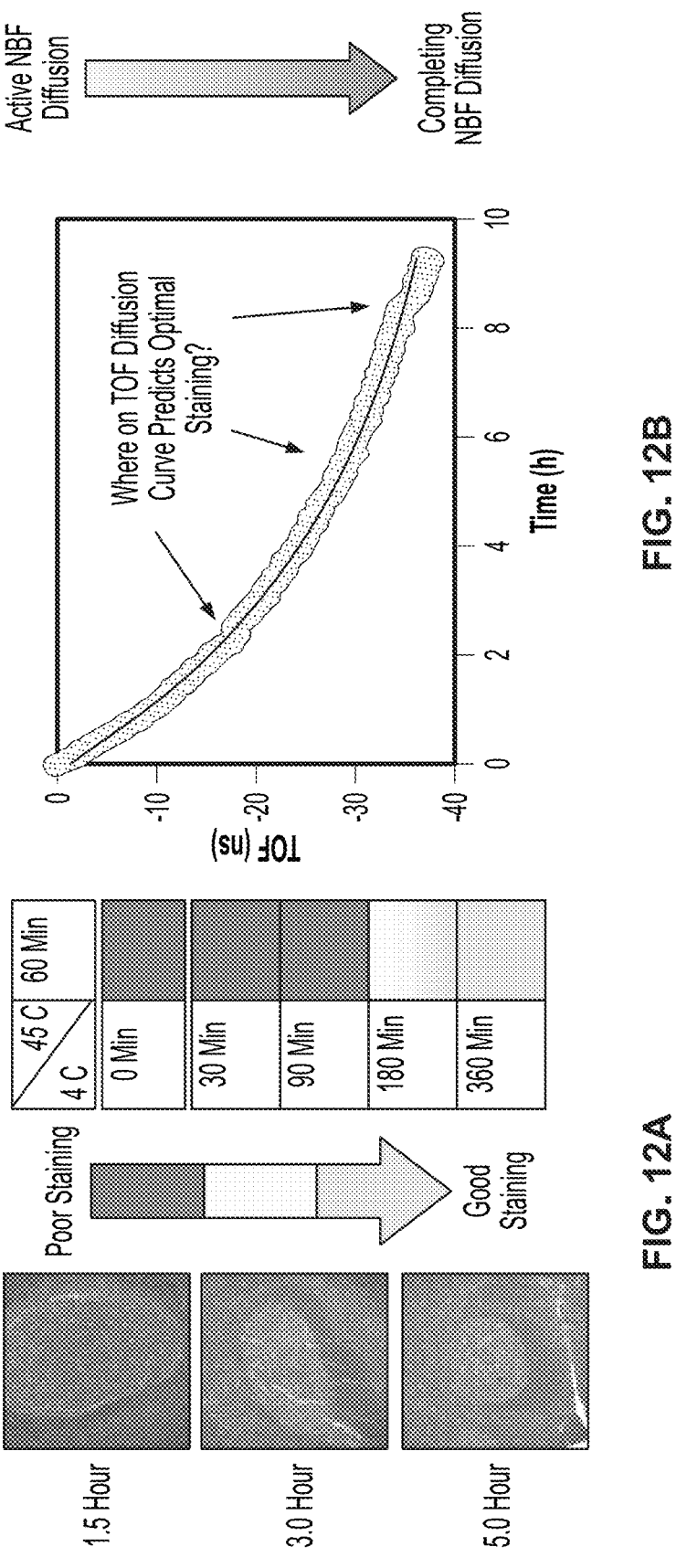

FIGS. 12A and 12B illustrate the correlation of NBF diffusion times with stain quality. a) H&E images acquired with different cold soak times in NBF. Based on H&E based morphology, cold soak times of 1.5 hours, 3 hours, and 5 hours produced severely comprised, borderline, and exemplary staining, respectively. b) Example depiction of TOF diffusion curve with active NBF diffusion immediately after submerging tissue in NBF, manifesting with a rapidly changing TOF signal. Conversely, after several hours the tissue's rate of diffusion had significantly slowed as the tissue and NBF approached osmotic equilibrium.

FIGS. 13A-13E illustrate the tuning rate of diffusion metric to predict stain quality. a) Normalized slope for tonsil tissues at 3 hours and 5 hours in cold NBF when tissues are expected to have borderline and ideal staining, respectively. Different threshold diffusion rates of −7.4%/hr, −8.0%/hr, and −10.4%/hr are indicated with 3, 2, and 1 respectively. b) Average TOF signal from a 6 mm tonsil with the approximate locations of the threshold diffusion rates indicated. c-e) Plots of the projected completion times for each of the three evaluated threshold diffusion rates.

Figure 14B:
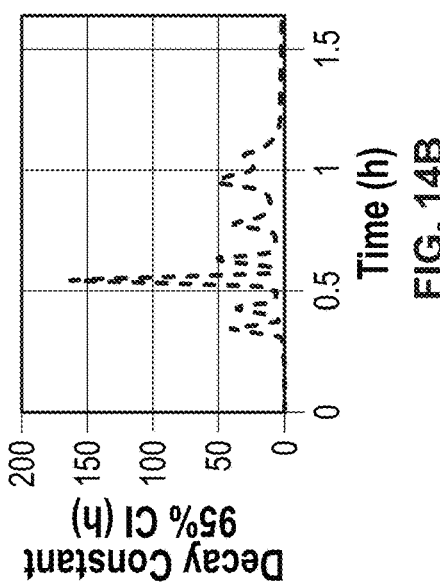
Figure 14A:
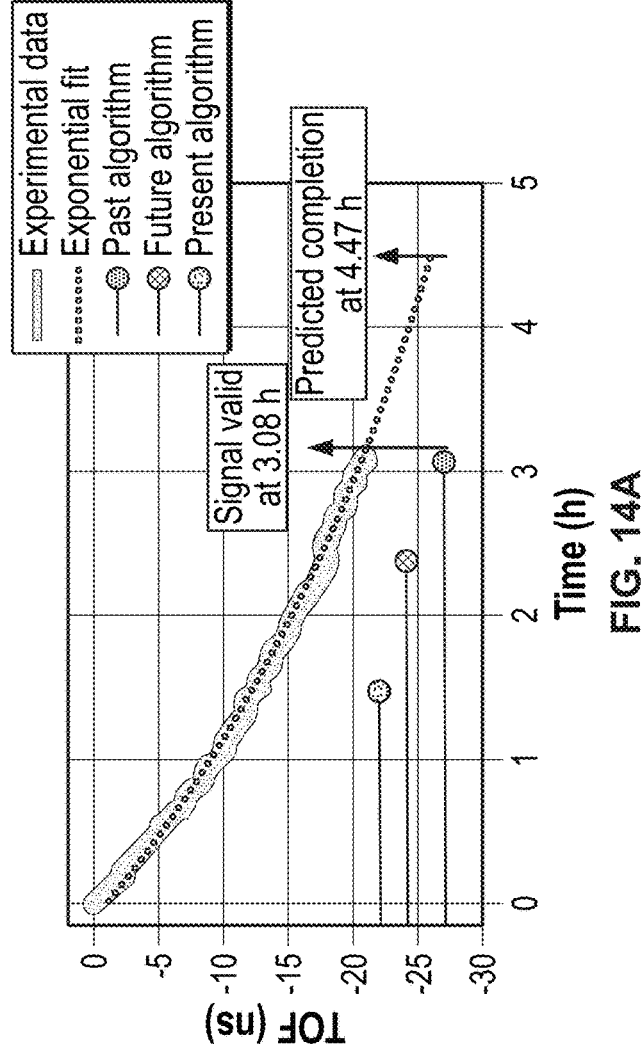
Figure 14E:
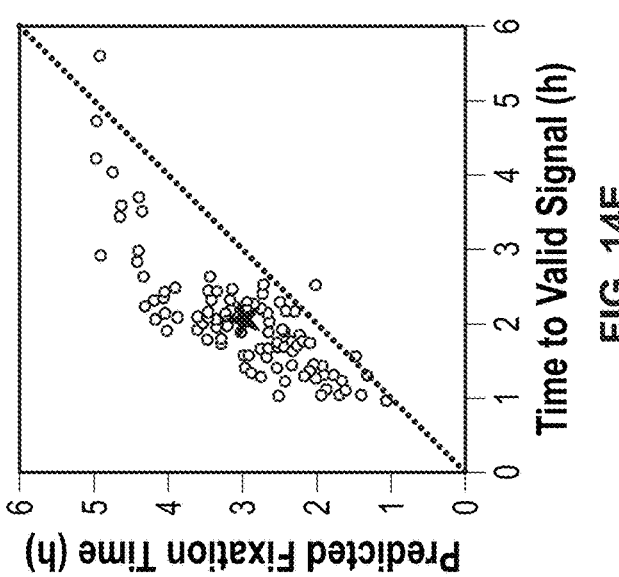
Figure 14D:
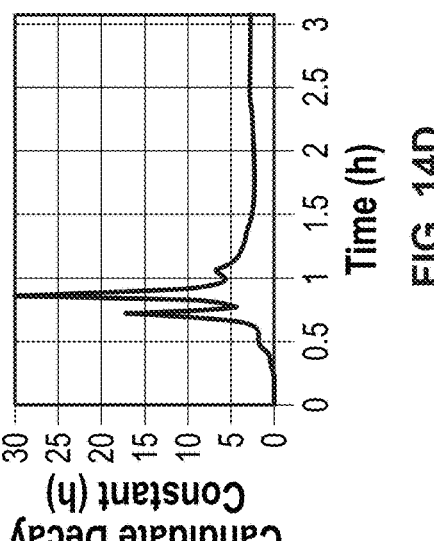
Figure 14C:
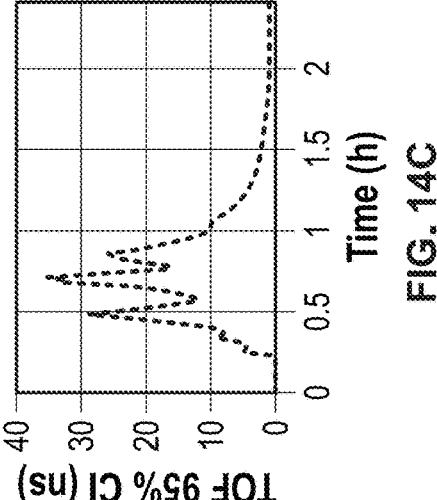

FIGS. 14A-14E set forth an example of a statistical model to validate TOF diffusion signal. a) TOF diffusion curve demonstrating how a validation algorithm works during real-time data acquisition. As data is collected, three statistical algorithms (also referred to herein as "confidence models") continually monitor the fidelity of the signal focusing on past, present, and future aspects of the data (past confidence model, present confidence model, and future confidence model). The time to satisfy each algorithm (confidence models) is labeled on the plot with solid horizontal lines in order of convergence time. Once all three conditions of data fidelity are satisfied, the data is representative of the tissue's actual rate of diffusion and the required diffusion time of the tissue was calculated. Detailed views of the present, future, and past algorithms are shown in FIGS. 14B, 14C, and 14D respectively. e) Plot of time to validate diffusion signal versus predicted fixation times for 105 tissues. On average (star in FIG. 14E), 2.04 hours was required for the detected diffusion profile to converge onto the tissue's actual rate of diffusion and tissues were predicted to need 2.96 hours of diffusion in cold formalin.

Figure 15:
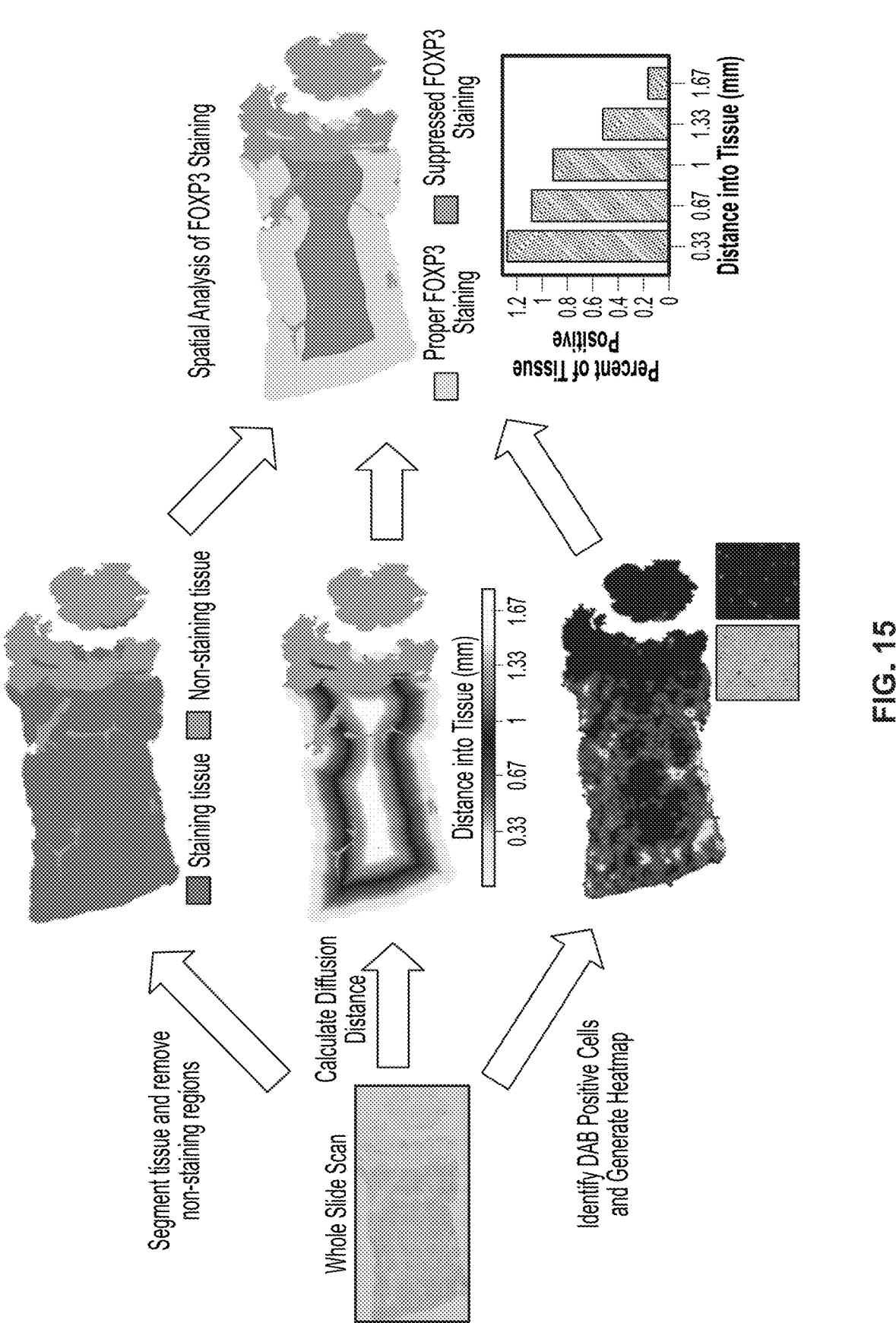

FIG. 15 provides a schematic of radial image analysis workflow used to analyze the impact of formalin diffusion on functional IHC staining to FOXP3.

Figure 16:
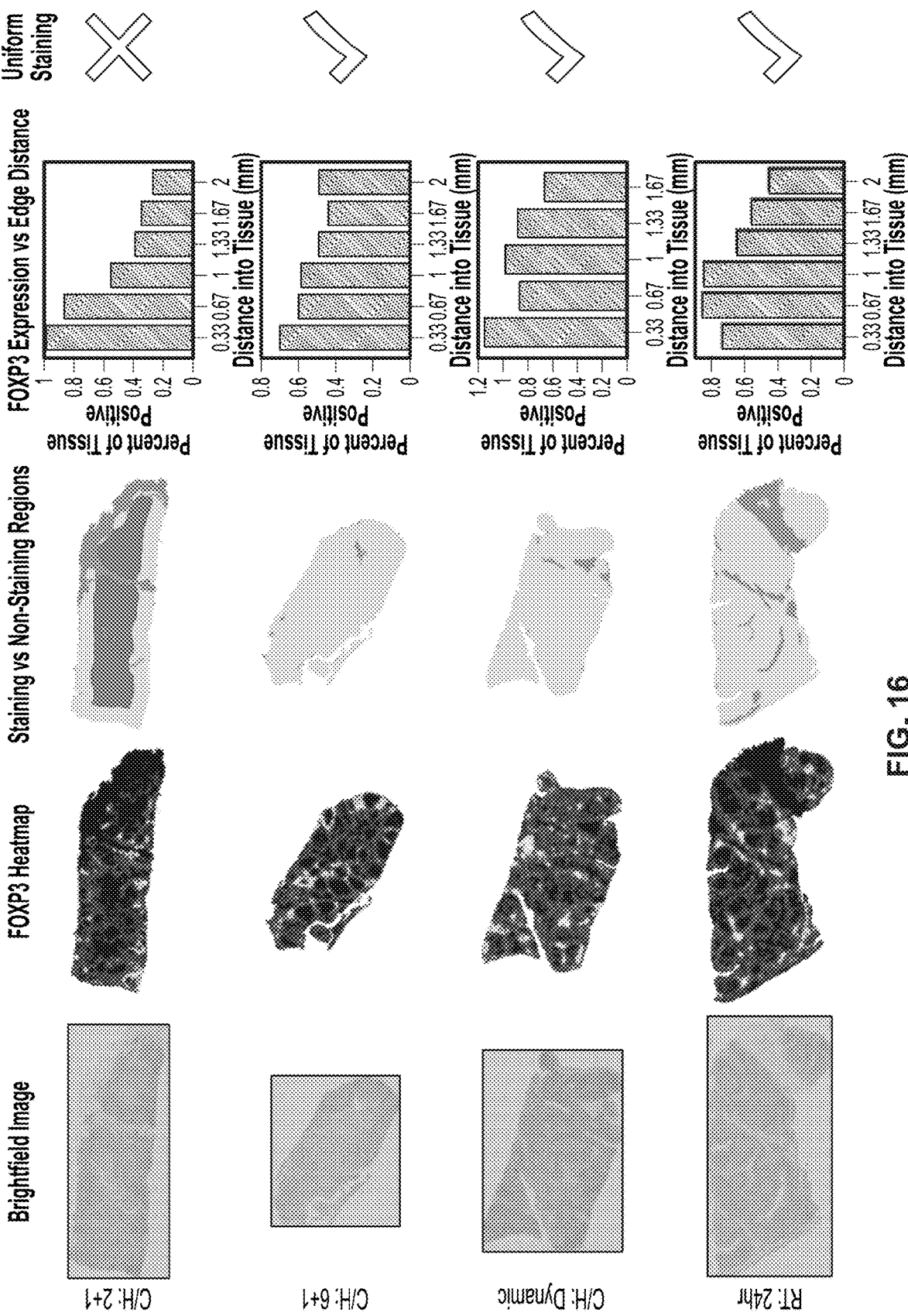

FIG. 16 sets forth a comparative example of staining results for different fixation protocols. Left column) Bright-field whole slide scan of tissue. Middle-left column) Heatmap of FOXP3 positivity for each tissue. Middle-right column) Graphical depiction of radial zones within each tissue indicating regions of deficient and proper staining, as defined by DAB positivity within 50% of the edge value. Right column) Histogram of FOXP3 staining versus distance to the edge of the tissue.

FIGS. 17A-17C illustrate a quantitative analysis of FOXP3 staining for different fixation protocols. a) Penetration depth of proper FOXP3 staining, as defined by distance into tissue where staining drops to half its edge value. b) Percent of tissue displaying proper FOXP3 staining. c) Normalized FOXP3 expression plotted versus distance into tissue. Solid lines indicate p<0.002 according to Welch's 2-sided t-test.

FIGS. 18A-18C depict a quantitative bcl-2 expression for different fixation protocols. a) Penetration depth of proper bcl-2 staining. b) Area of proper bcl-2 staining. c) Normalized bcl-2 expression plotted versus distance into the tissue.

Figure 19B:
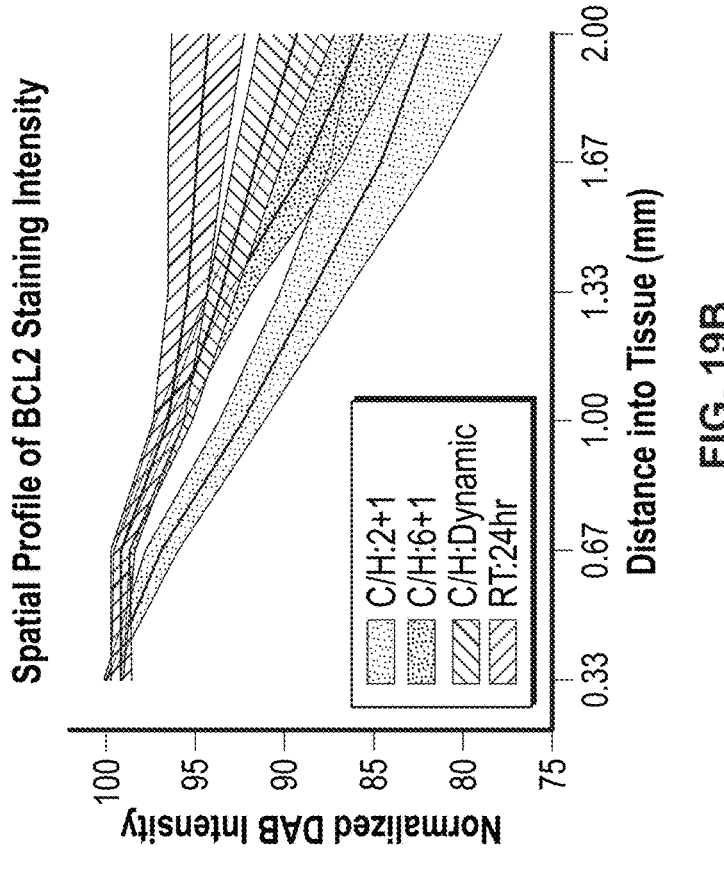
Figure 19A:
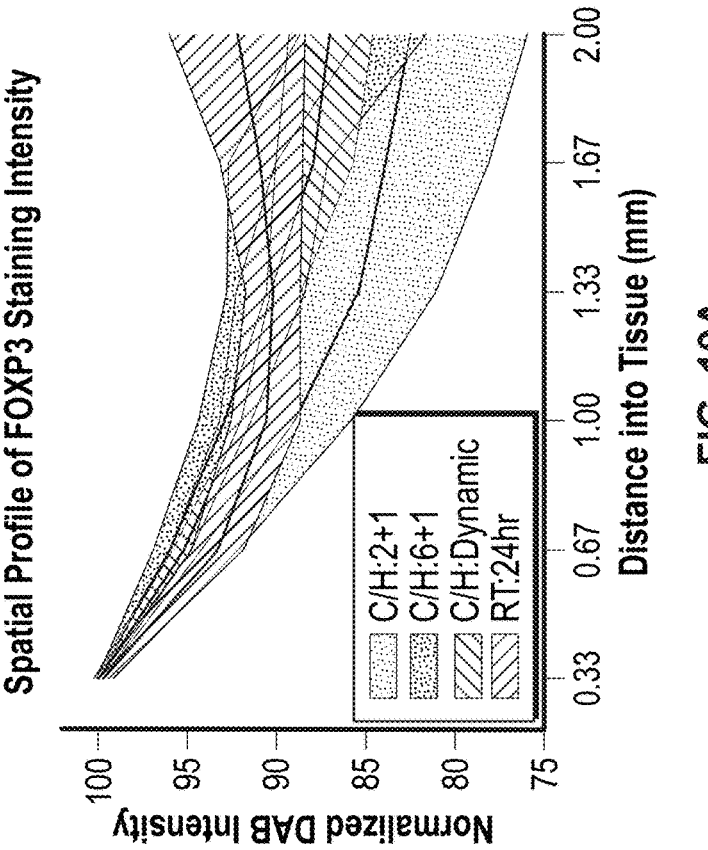

FIGS. 19A-19B provide a quantitative analysis of stain intensity for different fixation protocols. a) Normalized intensity of FOXP3 staining plotted versus distance into the tissue. b) Normalized intensity of bcl-2 staining plotted versus distance into the tissue.

Figure 20:
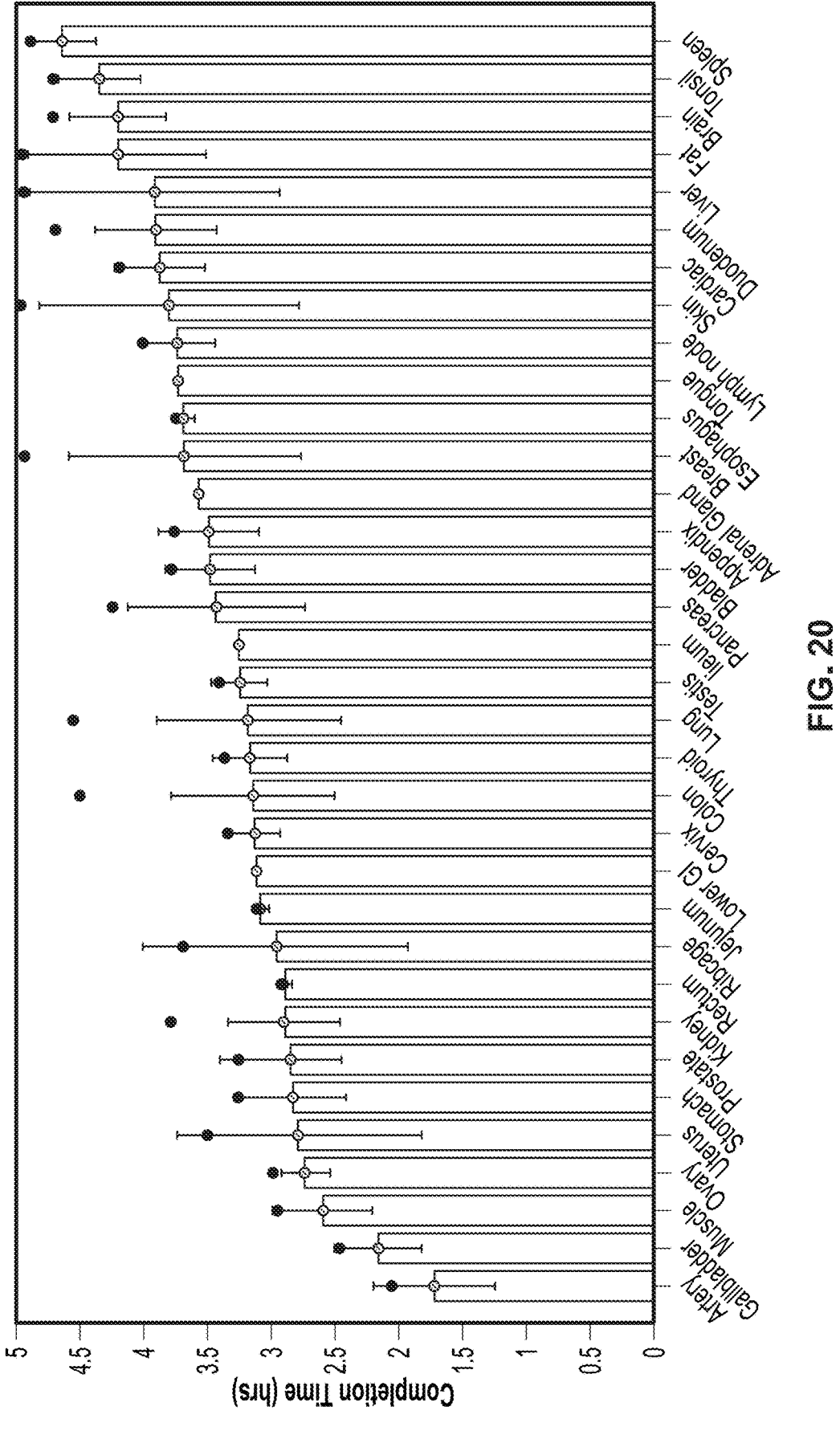

FIG. 20 depicts the projected optimal fixation times for numerous tissue types based on the developed predictive algorithm.

Figure 21:
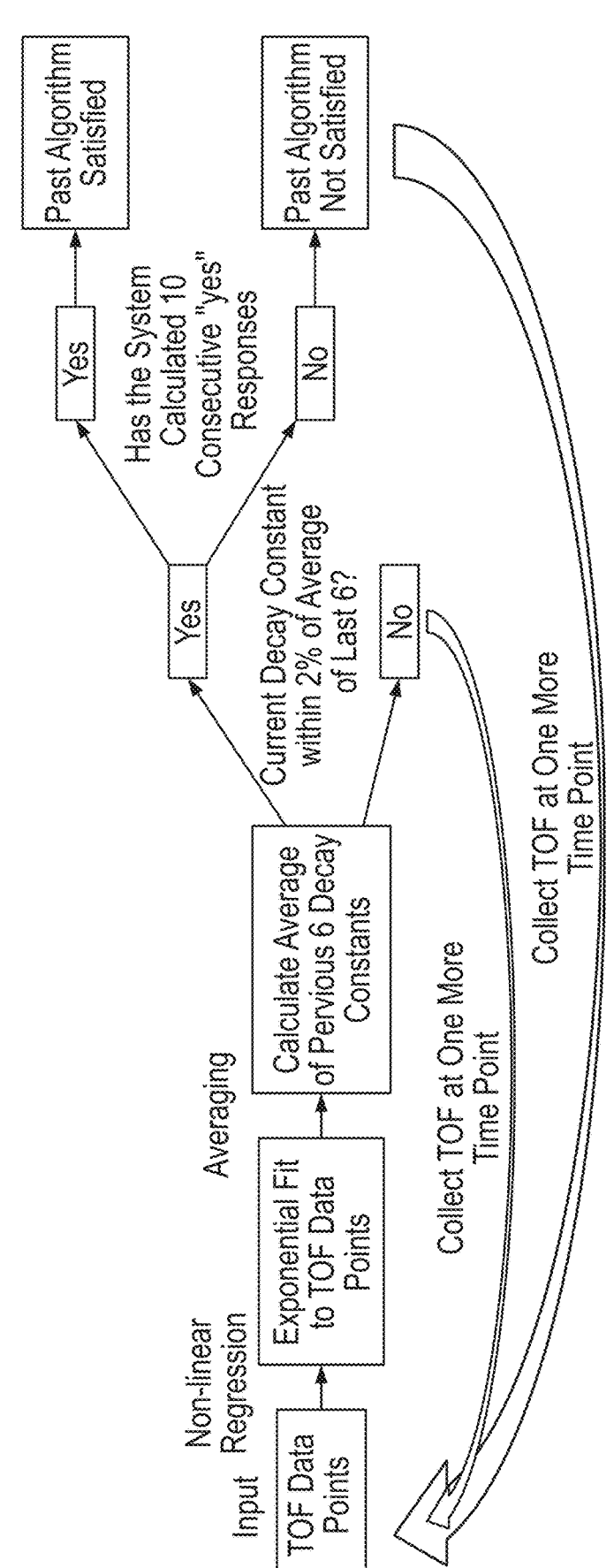

FIG. 21 provides a flowchart illustrating the steps undertaken, in some aspects of the present disclosure, of the past confidence module.

Figure 22:
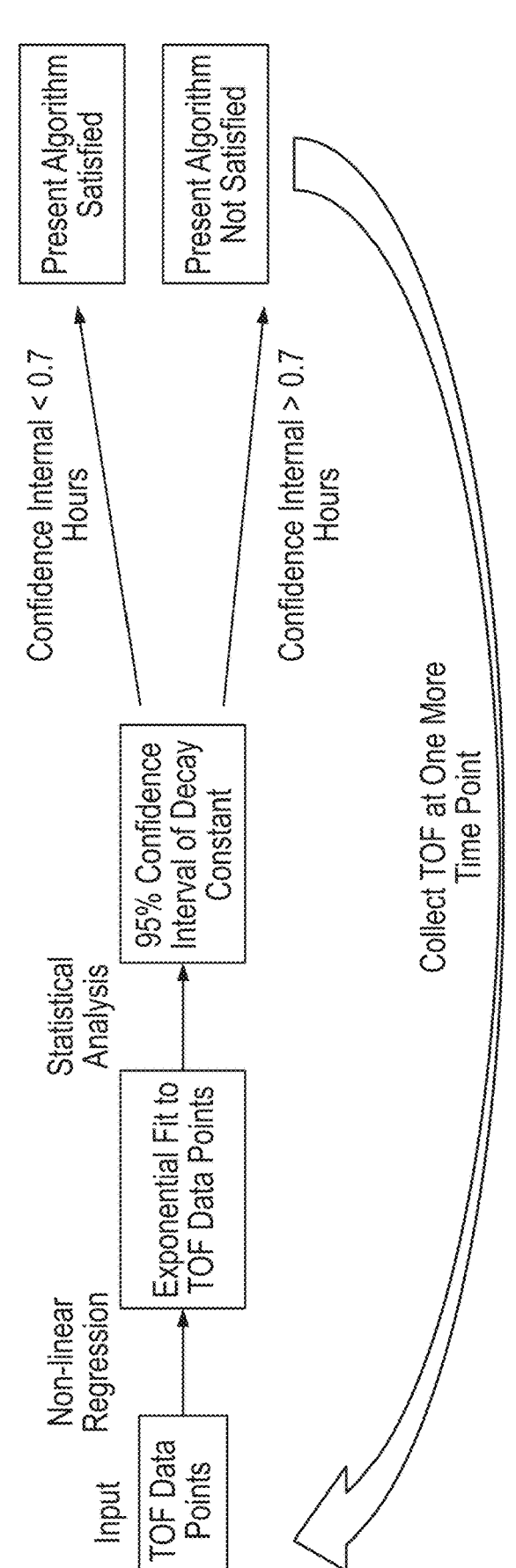

FIG. 22 provides a flowchart illustrating the steps undertaken, in some aspects of the present disclosure, of the present confidence module.

Figure 23:
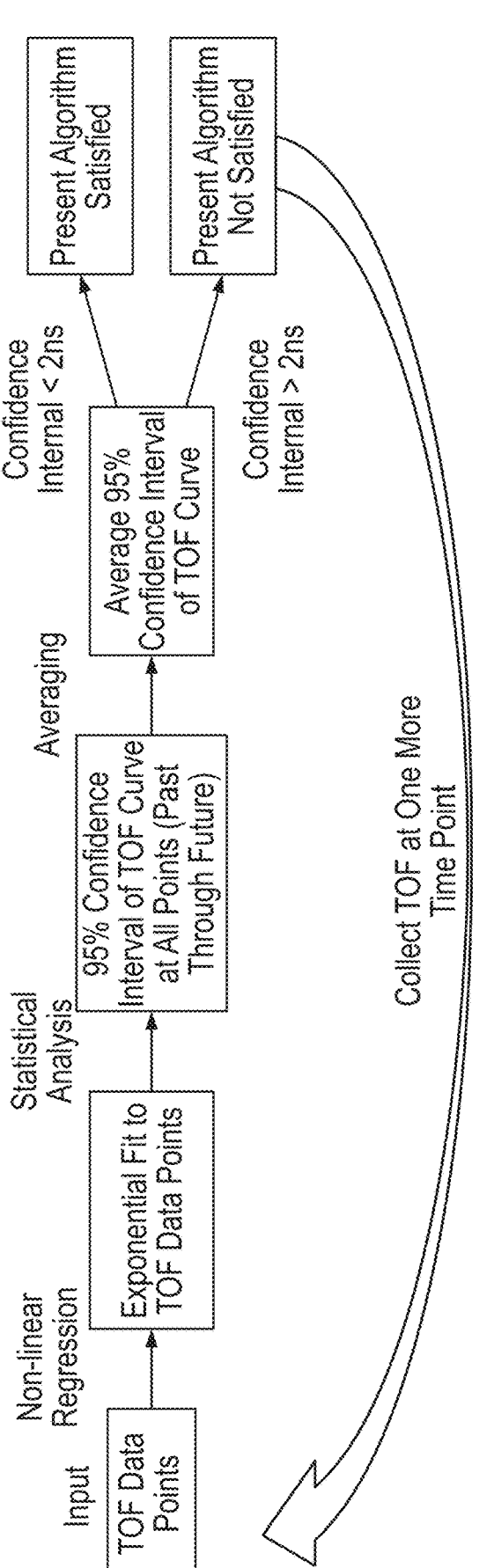

FIG. 23 provides a flowchart illustrating the steps undertaken, in some aspects of the present disclosure, of the future confidence module.

DETAILED DESCRIPTION

It should also be understood that, unless clearly indicated to the contrary, in any methods claimed herein that include more than one step or act, the order of the steps or acts of the method is not necessarily limited to the order in which the steps or acts of the method are recited.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g., "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b, and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the terms "biological specimen," "tissue specimen," "tissue sample" and the like refer to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats, and primates), insects, annelids, arachnids, marsupials, reptiles, amphibians, bacteria, and fungi. Biological specimens include tissue samples (such as tissue sections and needle biopsies of tissue), cell samples (such as cytological smears such as Pap smears or blood smears or samples of cells obtained by microdissection), or cell fractions, fragments, or organelles (such as obtained by lysing cells and separating their components by centrifugation or otherwise). Other examples of biological specimens include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological specimen. In certain embodiments, the term "biological specimen" as used herein refers to a sample (such as a homogenized or liquefied sample) prepared from a tumor or a portion thereof obtained from a subject.

As used herein, the terms "biomarker" or "marker" refer to a measurable indicator of some biological state or condition. In particular, a biomarker may be a protein or peptide, e.g., a surface protein, that can be specifically stained, and which is indicative of a biological feature of the cell, e.g., the cell type or the physiological state of the cell. An immune cell marker is a biomarker that is selectively indicative of a feature that relates to an immune response of a mammal. A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "cell," refers to a prokaryotic cell or a eukaryotic cell. The cell may be an adherent or a non-adherent cell, such as an adherent prokaryotic cell, adherent eukaryotic cell, non-adherent prokaryotic cell, or non-adherent eukaryotic cell. A cell may be a yeast cell, a bacterial cell, an algae cell, a fungal cell, or any combination thereof. A cell may be a mammalian cell. A cell may be a primary cell obtained from a subject. A cell may be a cell line or an immortalized cell. A cell may be obtained from a mammal, such as a human or a rodent. A cell may be a cancer or tumor cell. A cell may be an epithelial cell. A cell may be a red blood cell or a white blood cell. A cell may be an immune cell such as a T cell, a B cell, a natural killer (NK) cell, a macrophage, a dendritic cell, or others. A cell may be a neuronal cell, a glial cell, an astrocyte, a neuronal support cell, a Schwann cell, or others. A cell may be an endothelial cell. A cell may be a fibroblast or a keratinocyte. A cell may be a pericyte, hepatocyte, a stem cell, a progenitor cell, or others. A cell may be a circulating cancer or tumor cell or a metastatic cell. A cell may be a marker specific cell such as a CD8+ T cell or a CD4+ T cell. A cell may be a neuron. A neuron may be a central neuron, a peripheral neuron, a sensory neuron, an interneuron, a intraneuronal, a motor neuron, a multipolar neuron, a bipolar neuron, or a pseudo-unipolar neuron. A cell may be a neuron supporting cell, such as a Schwann cell. A cell may be one of the cells of a blood-brain barrier system. A cell may be a cell line, such as a neuronal cell line. A cell may be a primary cell, such as cells obtained from a brain of a subject. A cell may be a population of cells that may be isolated from a subject, such as a tissue biopsy, a cytology specimen, a blood sample, a fine needle aspirate (FNA) sample, or any combination thereof. A cell may be obtained from a bodily fluid such as urine, milk, sweat, lymph, blood, sputum, amniotic fluid, aqueous humor, vitreous humor, bile, cerebrospinal fluid, chyle, chyme, exudates, endolymph, perilymph, gastric acid, mucus, pericardial fluid, peritoneal fluid, pleural fluid, pus, rheum, saliva, sebum, serous fluid, smegma, sputum, tears, vomit, or other bodily fluid. A cell may comprise cancerous cells, non-cancerous cells, tumor cells, non-tumor cells, healthy cells, or any combination thereof.

A used herein, the terms "diffusion coefficient" or "diffusivity constant" refer to a proportionality constant between the molar flux due to molecular diffusion and the gradient in the concentration of the object whose diffusion is observed (or the driving force for diffusion). Diffusivity is encountered e.g., in Fick's law and numerous other equations of physical chemistry. The higher the diffusivity (of one substance with respect to another), the faster they diffuse into each other. Typically, a compound's diffusivity constant is about 10,000 times as great in air as in water. For example, carbon dioxide in air has a diffusivity constant of 16 mm2/s, and in water its diffusivity constant is 0.0016 mm2/s.

As used herein, the term "fluid" refers to one or more liquids or liquid compositions, including reagents, solvents, solutions (e.g., polar solvents, non-polar solvents), mixtures, etc. The fluid may be aqueous or non-aqueous. Non-limiting examples of fluids include solvents and/or solutions for deparaffinizing paraffin-embedded biological specimens or hydrocarbons (e.g., alkanes, isoalkanes and aromatic compounds such as xylene). Still further examples of fluids include solvents (and mixtures thereof) used to dehydrate or rehydrate biological specimens. In some embodiments, fluids include one or more glycol ethers, such as one or more propylene-based glycol ethers (e.g., propylene glycol ethers, di(propylene glycol) ethers, and tri(propylene glycol) ethers, ethylene-based glycol ethers (e.g., ethylene glycol ethers, di(ethylene glycol) ethers, and tri(ethylene glycol) ethers), and functional analogs thereof. Yet other solutions are described in United States Patent Application Publication No. 2016/0282374, the disclosure of which is hereby incorporated by reference herein in its entirety.

As used herein, the term "fixation" refers to a process by which molecular and/or morphological details of a cellular sample are preserved. There are generally three kinds of fixation processes: (1) heat fixation, (2) perfusion; and (3) immersion. With heat fixation, samples are exposed to a heat source for a sufficient period of time to heat kill and adhere the sample to the slide. Perfusion involves use of the vascular system to distribute a chemical fixative throughout a whole organ or a whole organism. Immersion involves immersing a sample in a volume of a chemical fixative and allowing the fixative to diffuse throughout the sample. Chemical fixation involves diffusion or perfusion of a chemical throughout the cellular samples, where the fixative reagent causes a reaction that preserves structures (both chemically and structurally) as close to that of living cellular sample as possible.

Fixatives (or "fixative solutions") can be classified into two broad classes based on mode of action: cross-linking fixatives and non-cross-linking fixatives. Cross-linking fixatives—typically aldehydes—create covalent chemical bonds between endogenous biological molecules, such as proteins and nucleic acids, present in the tissue sample. In some embodiments, the fixative is an aldehyde-based cross-linking fixative, such as glutaraldehyde- and/or formalin-based solutions. Examples of aldehydes frequently used for immersion fixation include: formaldehyde (standard working concentration of about 5 to about 10% formalin for most tissues, although concentrations as high as about 20% formalin have been used for certain tissues); glyoxal (standard working concentration 17 to 86 mM); glutaraldehyde (standard working concentration of 200 mM).

In some embodiments, aldehydes are often used in combination with one another. Standard aldehyde combinations include 10% formalin+1% (w/v) Glutaraldehyde. Atypical aldehydes have been used in certain specialized fixation applications, including: fumaraldehyde, 12.5% hydroxyadipaldehyde (pH 7.5), 10% crotonaldehyde (pH 7.4), 5% pyruvic aldehyde (pH 5.5), 10% acetaldehyde (pH 7.5), 10% acrolein (pH 7.6), and 5% methacrolein (pH 7.6). Other specific examples of aldehyde-based fixative solutions used for immunohistochemistry are set forth in Table 1:

TABLE 1

| Solution | Standard Composition |
|---|---|
| Neutral Buffered Formalin | 5-20% formalin + phosphate buffer (pH ~6.8) |
| Formal Calcium | 10% formalin + 10 g/L calcium chloride |
| Formal Saline | 10% formalin + 9 g/L sodium chloride |
| Zinc Formalin | 10% formalin + 1 g/L zinc sulphate |
| Helly's Fixative | 50 mL 100% formalin + 1 L aqueous solution containing 25 g/L potassium dichromate + 10 g/L sodium sulfate + 50 g/L mercuric chloride |
| B-5 Fixative | 2 mL 100% formalin + 20 mL aqueous solution containing 6 g/L mercuric chloride + 12.5 g/L sodium acetate (anhydrous) |
| Hollande's Solution | 100 mL 100% formalin + 15 mL Acetic acid + 1 L aqueous solution comprising 25 g copper acetate and 40 g picric acid |
| Bouin's Solution | 250 mL 100% formalin + 750 mL saturated aqueous picric acid + 50 mL glacial acetic acid |

Formaldehyde is the most commonly used cross-linking fixative in histology. Formaldehyde may be used in various concentrations for fixation, but it primarily is used as 10% neutral buffered formalin (NBF), which is about 3.7% formaldehyde in an aqueous phosphate buffered saline solution. Paraformaldehyde is a polymerized form of formaldehyde, which depolymerizes to provide formalin when heated. Glutaraldehyde operates in similar manner as formaldehyde, but is a larger molecule having a slower rate of diffusion across membranes. Glutaraldehyde fixation provides a more rigid or tightly linked fixed product, causes rapid and irreversible changes, fixes quickly and well at 4° C., provides good overall cytoplasmic and nuclear detail, but is not ideal for immunohistochemistry staining. Some fixation protocols use a combination of formaldehyde and glutaraldehyde. Glyoxal and acrolein are less commonly used aldehydes. Denaturation fixatives—typically alcohols or acetone—act by displacing water in the cellular sample, which destabilizes hydrophobic and hydrogen bonding within proteins. This causes otherwise water-soluble proteins to become water insoluble and precipitate, which is largely irreversible.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a planar surface, e.g., a microscope slide.

As used herein, the term "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection). In some instances, indirect detection can include tertiary or higher antibodies that serve to further enhance the detectability of the antigen. Examples of detectable labels include enzymes, fluorophores and haptens, which in the case of enzymes, can be employed along with chromogenic or fluorogenic substrates.

As used herein, the term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1 inch microscope slide or a standard 75 mm by 25 mm microscope slide. Examples of biological specimens that can be placed on a slide include, without limitation, a cytological smear, a thin tissue section (such as from a biopsy), and an array of biological specimens, for example a tissue array, a cellular array, a DNA array, an RNA array, a protein array, or any combination thereof. Thus, in one embodiment, tissue sections, DNA samples, RNA samples, and/or proteins are placed on a slide at particular locations. In some embodiments, the term slide may refer to SELDI and MALDI chips, and silicon wafers.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^3$ M$^{-1}$ greater, 104 M$^{-1}$ greater or $10^5$ M$^{-1}$ greater than a binding constant for either of the two members of the binding pair with other molecules in a biological specimen). Examples of specific binding moieties include specific binding proteins (for example, antibodies, lectins, avidins such as streptavidins, and protein A). Specific binding moieties can also include the molecules (or portions thereof) that are specifically bound by such specific binding proteins. Specific binding entities include primary antibodies, described above, or nucleic acid probes.

As used herein, the terms "stain," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide a contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the term "substantially" means the qualitative condition of exhibiting total or near-total extent or degree of a characteristic or property of interest. In some embodiments, "substantially" means within about 20%. In some embodiments, "substantially" means within about 15%. In some embodiments, "substantially" means within about 10%. In some embodiments, "substantially" means within about 5%. In some embodiments, "substantially" means within about 2.5%. In some embodiments, "substantially" means within about 2%. In some embodiments, "substantially" means within about 1.5%. In some embodiments, "substantially" means within about 1%.

As used herein, the term "target" refers to any molecule for which the presence, location and/or concentration is or can be determined. Examples of target molecules include proteins, epitopes, nucleic acid sequences, and haptens, such as haptens covalently bonded to proteins. Target molecules are typically detected using one or more conjugates of a specific binding molecule and a detectable label.

As used herein, the term "time-of-flight" ("TOF") refers to the time that it takes for an object, particle, or a wave (e.g., an acoustic wave, electromagnetic wave, etc.) to travel a distance through a medium. The TOF may be measured empirically, e.g., by determining a phase differential between the phases of an acoustic signal emitted by a transmitter ("transmitted signal") and an acoustic signal received by a receiver ("received signal"). TOF information can then be used to learn about the properties of a material (e.g., a biological specimen) disposed in the medium (such as the material's composition). For instance, TOF may be used to determine the diffusion of a fixative (e.g., formalin) into a biological specimen (e.g., a tissue sample). Formalin diffuses into a tissue section and cross-links proteins and nucleic acids, thereby halting metabolism, preserving biomolecules, and readying the tissue for paraffin wax infiltration. In some embodiments, algorithms may then be utilized to determine how diffused with the fixative a biological specimen must be in order to be optimally fixed and therefore to ensure proper and ideal staining.

Overview

The present disclosure provides systems and methods which facilitate the prediction of an estimated time in which a fluid will be optimally diffused into a biological specimen, e.g., an estimated time it will take for a fluid to reach a particular concentration at a particular location in the tissue sample, such as a center region of the biological specimen.

In some embodiments, the fluid includes one or more fixatives (including any of those described herein). In other embodiments, the fluid includes dehydrating reagents (such as graded ethanols), clearing agents (such as xylene), and paraffin used for embedding of a biological specimen.

In some embodiments, the fluid includes 10% NBF. In some embodiments, the fluid includes about 70% ethanol. In some embodiments, the fluid includes about 80% ethanol. In some embodiments, the fluid includes about 90% ethanol. In some embodiments, the fluid includes about 100% ethanol. In some embodiments, the fluid includes xylene. In some embodiments, the fluid includes paraffin.

It is believed that the extent of diffusion of a fluid into a biological specimen may have an impact on downstream processing and analytical methods. For example, and in the context of a fixation quality of a biological specimen, under current clinical practice it is important to control the fixation duration to achieve a compromise between the preservation of tissue morphology and the loss of antigenicity. Indeed, a fixation duration that is too short or too long may negatively impact downstream sample processing. Thus, there remains a need for the accurate prediction of a time at which a biological specimen will be optimally fixed prior to downstream processing, e.g., prior to contacting the biological specimen with one or more specific binding entities. Applicant has surprisingly discovered that the systems and methods of the present disclosure provide for an accurate prediction of a time in which a fluid (e.g., one or more fixatives) is optimally diffused into a biological specimen, e.g., a tissue specimen or a cytological specimen.

In view of the foregoing, and in the context of fixing a biological specimen, the present disclosure provides systems and methods which facilitate the prediction of an estimated time at which a biological specimen, e.g., a tissue sample derived from a human subject, will optimally be fixed (also referred to herein as the "time to fixation" or the "time to fixation completion"). In some embodiments, the prediction of the time at which the biological specimen will be optimally fixed is based on TOF data acquired at a particular point in time during the fixation process (e.g., a single temperature fixation process or a two-temperature fixation process) that has been deemed sufficiently accurate (i.e., the TOF data at a particular time point meets predetermined criteria indicative of it being valid and suitable for downstream processing) such that a time needed to achieve a certain concentration or amount of the fixative within the biological specimen may be predicted. The determination of a "time to fixation completion" (such as using a prediction module 204) and the determination of what TOF data is "deemed sufficiently accurate" (such as using a signal modeling module 203) in order to make the prediction is described further herein.

Figure 1A:
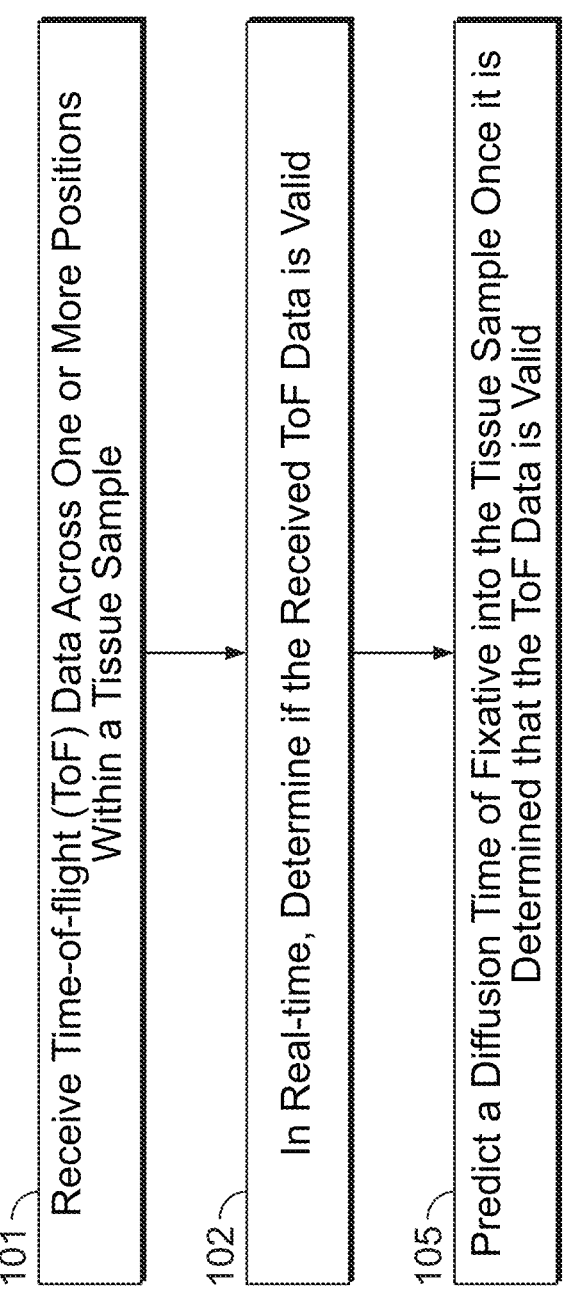
Figure 5B:
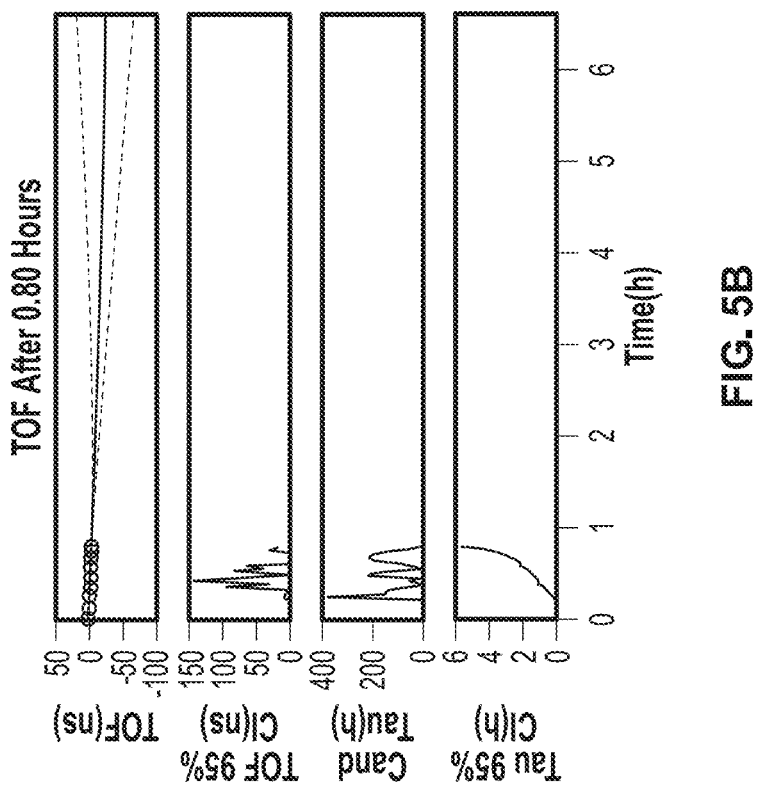
FIGS. 5A-5F provide time courses showing how criteria are calculated while scanning a tonsil tissue for a) 0.4 hours, b) 0.8 hours, c) 1.2 hours, d) 2.2 hours, e) 2.83 hours, and 4.84 hours. Top plot: TOF curve with black circles representing single TOF data points, the best-fit curve is depicted with a solid black line; the 95% confident interval is depicted with the dashed or dotted lines. Top-middle plot: The width of the 95% confident interval for the TOF curve. Bottom-middle plot: Candidate decay constant calculated using the most recent data point acquired. Bottom plot: 95% confidence interval of the decay constant.
Figure 5A:
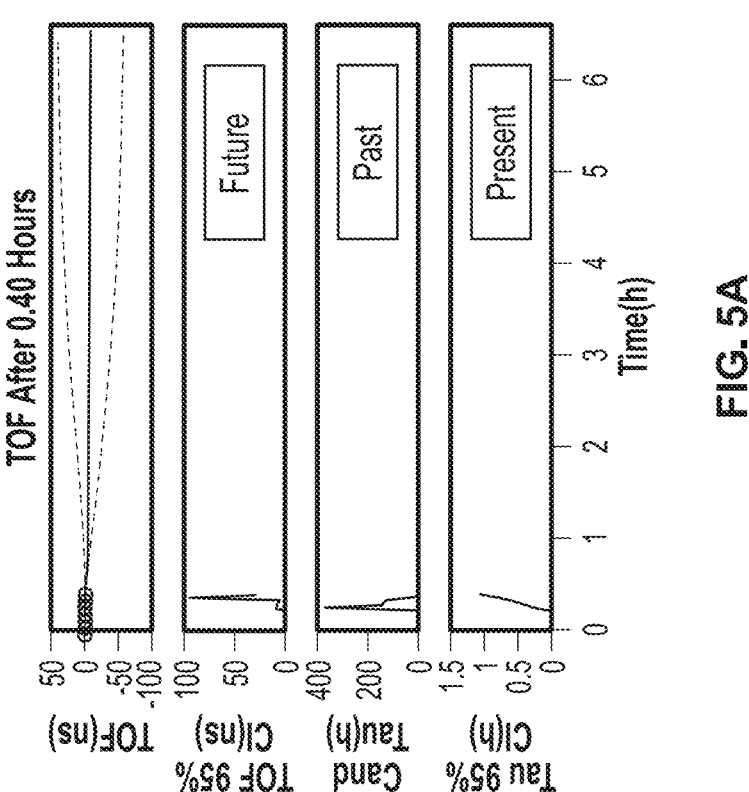
Figure 5D:
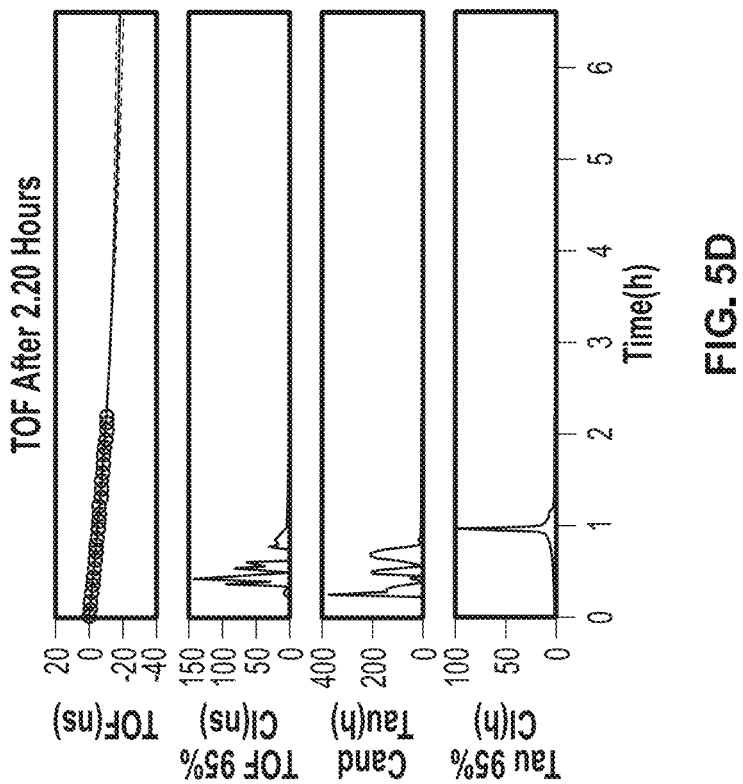
Figure 5C:
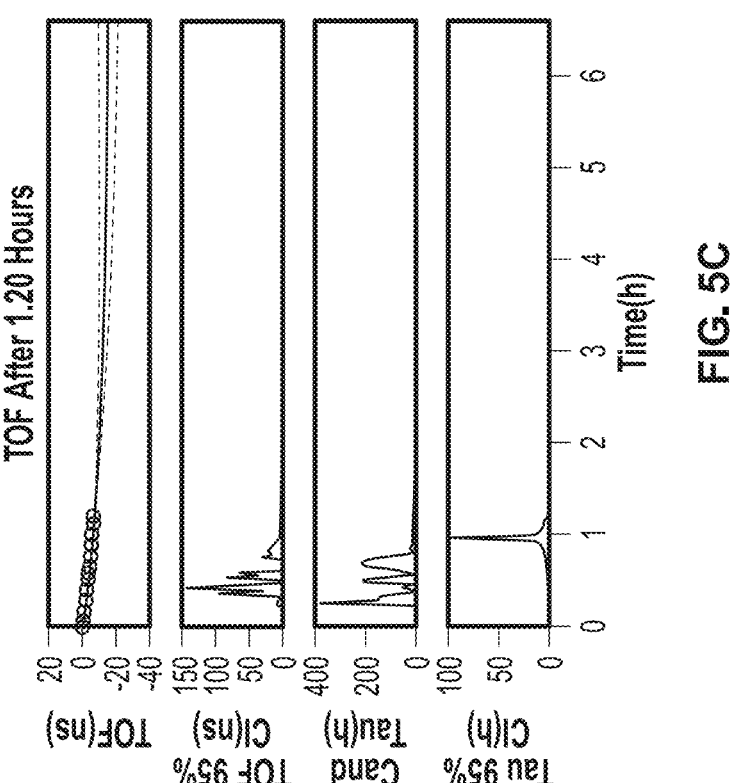
Figure 5F:
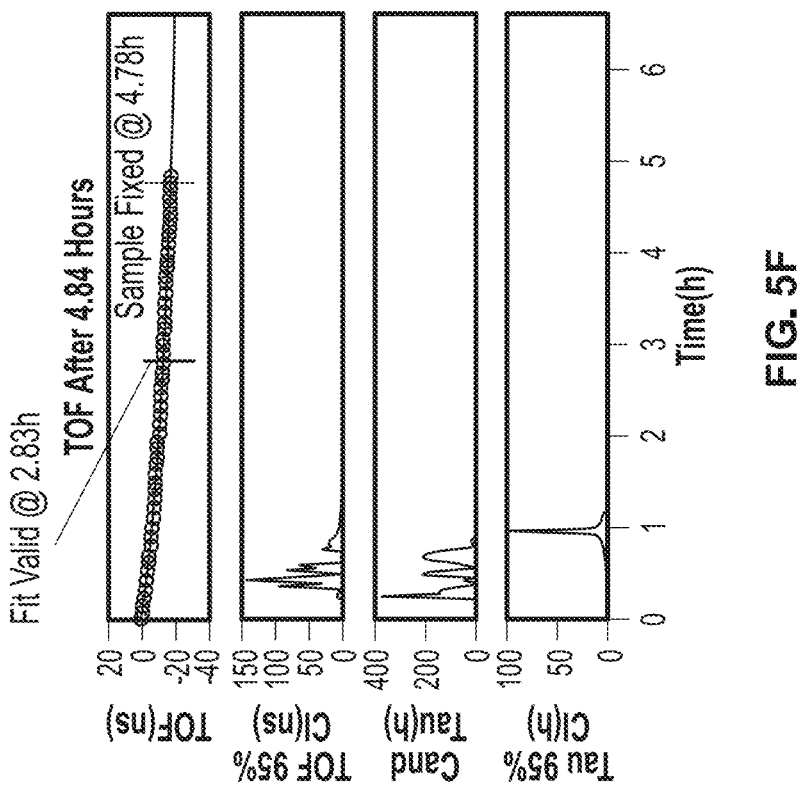
Figure 5E:
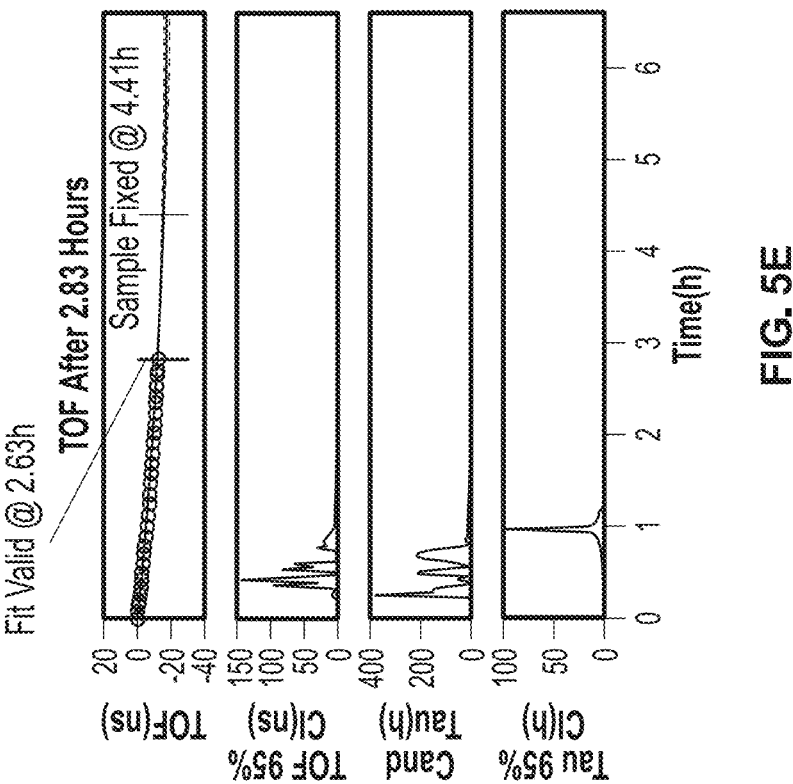

With reference to FIGS. 1A and 1B, at least some embodiments of the present disclosure relate to systems and methods for (i) acquiring TOF data (step 101) through a biological specimen, such as at a plurality of positions across the biological specimen; and (ii) analyzing the acquired TOF data, such as in real-time, while the biological specimen is immersed in a fluid e.g., one or more fixatives. In some embodiments, the fluid comprises one or more fixatives and the biological specimen is immersed in the one or more fixatives while acoustic data is collected, such as continuously collected (e.g., continuously collected between every about 0.2 seconds to about 120 seconds). In some embodiments, the acquired TOF data is analyzed in real-time to determine whether acquired TOF data at a particular point in time is deemed sufficiently accurate (step 102) such that the TOF data at that particular point in time may be used to estimate a time in which the fluid is optimally diffused into a biological specimen, e.g., when the fluid comprises one or more fixatives to estimate a time in which a biological specimen will be optimally fixed (step 105).

In some embodiments, the determination of whether acquired TOF data at a particular point in time is deemed sufficiently accurate such that the TOF data at that particular point in time may be used to estimate a time in which a fluid is optimally diffused into a biological specimen or a time in which the biological specimen will be optimally fixed comprises computing at least two different confidence models, e.g., past and present confidence models. In some embodiments, three different confidence models are computed (see steps 103A, 103B, and 103C). In some embodiments, the at least two confidence models are re-calculated every time new TOF data is collected. When at least two of the confidence models are satisfied (step 104) (e.g., simultaneously satisfied by determining whether the received data independently meets predetermined threshold criteria for each of models), the signal is deemed accurate and the time at which the fluid is optimally diffused into the biological specimen or the time at which the biological specimen will be optimally fixed may be estimated (step 105).

In some embodiments, when at least two of the confidence models are satisfied, the systems and methods described herein facilitate the determination of a moment in time that TOF signal from the biological specimen is truly representative of the actual rate of diffusion (current and future) and predicts at what time the fluid will optimally be diffused into the biological specimen, or the time in which the biological specimen will be properly fixed. In some embodiments, if the time point at which the TOF data is deemed sufficiently accurate is in the future as compared with the time point at which the TOF data is deemed sufficiently accurate, then the biological specimen is left in the fluid, such as one or more fixative solutions. In other embodiments, if the time point at which the TOF data is deemed sufficiently accurate is in the past as compared with the time point at which the TOF data is deemed sufficiently accurate, then the biological specimen is removed from the fluid, such as one or more fixative solutions. In some embodiments, accuracy of the prediction can then be determined by comparing the model's determination of ground truth to the experimentally valid ground truth, i.e., how much did the fit change after the model predicted it was stable.

With reference to FIGS. 2 and 3, the system 200 includes a signal acquisition module 201 including one or more transmitters and/or one or more receivers (described further herein). In some embodiments, the signal acquisition module 201 is communicatively coupled to a computer 100. The computer system 100 can include a desktop computer, a laptop computer, a tablet, or the like, digital electronic circuitry, firmware, hardware, one or more memories 205, a computer storage medium (e.g., a storage module 240), a computer program or set of instructions (e.g., where the program is stored within the memory or storage medium), one or more processors 206 (including a programmed processor), and any other hardware, software, or firmware modules or combinations thereof (such as described further herein). In some embodiments, the signal acquisition module 201 may be coupled to the computer 100 either locally or via a network 120.

In some embodiments, the system 200 described herein may be communicatively coupled to additional components, e.g., servers, databases, microscopes, imaging devices, scanner, other imaging systems, automated slide preparation equipment, etc. These additional components are described herein. For example, the system 200 may be coupled to automated slide preparation equipment such that an optimally fixed biological specimen (determined according to the methods of the present disclosure) may be stained, such as immunoenzymatically, for the presence of one or more biomarkers (non-limiting examples of suitable biomarkers are described herein).

By way of another example, the system 200 may further include an imaging apparatus (e.g., to acquire images of biological specimens that have been immunoenzymatically stained for the presence of one or more biomarkers after the biological specimen has been optimally fixed) and images captured from the imaging device may be stored in binary form for further processing and/or analysis, such as locally or on a server. In some embodiments, the imaging apparatus (or other image source including pre-scanned images stored in a memory) can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the specimen. In some embodiments, the imaging apparatus is a brightfield imaging system, a multispectral imaging (MSI) system or a fluorescent microscopy system. In some embodiments, image data may be generated, for example, by an image scanning system, such as a VEN-TANA DP200 scanner by VENTANA MEDICAL SYS-TEMS, Inc. (Tucson, Arizona) or other suitable imaging equipment. Additional imaging devices and systems are described further herein. The skilled artisan will appreciate that the digital color image acquired by the imaging apparatus is conventionally composed of elementary color pixels. Each colored pixel can be coded over three digital components, each comprising the same number of bits, each component corresponding to a primary color, generally red, green, or blue, also denoted by the term "RGB" components.

FIG. 3 provides an overview of the system 200 of the present disclosure and the various modules utilized within system 200. In some embodiments, the system 200 employs a computer device or computer-implemented method having one or more processors 206 and one or more memories 205, the one or more memories 205 storing non-transitory computer-readable instructions for execution by the one or more processors to cause the one or more processors to execute certain instructions as described herein. As noted above, systems 200 of the present disclosure may be utilized to predict the fixation time of a biological specimen, i.e., the time at which the biological specimen is optimally fixed. Likewise, the systems 200 of the present disclosure may be utilized to predict a time in which a fluid is optimally diffused into a biological specimen, e.g., a tissue sample.

With reference to FIGS. 3 and 4, in some embodiments, the system 200 includes a signal acquisition module 201 which is adapted to acquire an acoustic data set (step 401). In some embodiments, the system 200 of the present disclosure further includes a signal processing module 202 which receives acoustic data from the signal acquisition module 201 (or from a memory 205 or storage subsystem 240 in communication therewith) and processes the received acoustic data (e.g., the signal processing module 202 may process the acoustic data set to generate TOF data, including one or more TOF data points, one or more TOF curves, one or more decay constants, etc.) (step 402). In some embodiments, the TOF data (e.g., output of the signal processing module 202 in the form of TOF data and/or TOF curves) is stored in a memory 205 or a storage subsystem 240 such that it may be retrieved as input by either the signal modeling module 203 or the prediction module 204.

In some embodiments, the system 200 further includes a signal modeling module 203 to assess whether acquired TOF data (including, in some embodiments, one or more TOF curves) accurately reflects the actual rate of diffusion of a fluid (e.g., one or more fixatives) through a biological specimen. In some embodiments, the signal modeling module 203 receives TOF data points (e.g., a predetermined number of TOF data points), one or more derived TOF curves, and/or one or more computed decay constants from the signal processing module 202 (or a memory 205 or storage subsystem 240 in communication therewith) and computes at least two different confidence models (step 403).

In some embodiments, the signal modeling module 203 computes at least two different confidence models or computes all three different confidence models. In some embodiments, the at least two different confidence models are continuously recomputed (e.g., every 0.2 seconds, every 0.5 seconds, every 1 second, every 5 seconds, every 10 seconds, every 20 seconds, every 30 seconds, every 60 seconds, etc.) based on newly received TOF data, e.g., newly generated TOF data acquired over time or newly generated TOF curves including newly acquired TOF data points. In some embodiments, the signal modeling module 203 continuously assesses the at least two computed confidence models to identify when at least two of the confidence models independently meet predetermined threshold criteria (step 404). As noted herein, the signaling modeling module 203 is used to determine, in real time (such as during diffusion of a fluid into the biological specimen or during fixation of the biological specimen), if the TOF data is valid and meets pre-determined threshold criteria.

In some embodiments, the system 200 further includes a prediction module 204 which is adapted to predict an estimated time in which a fluid is optimally diffused into a biological specimen or to predict an estimated time to fixation based on data received from the signal modeling module 203 (step 405). Subsequently, further downstream processing steps may be applied to the biological specimen. Each of these modules and the steps of determining a diffusion time of fixative into the biological specimen such that the biological specimen becomes optimally fixed are described further herein.

Signal Acquisition Module

In some embodiments, the system 200 includes a signal acquisition module 201. In some embodiments, the signal acquisition module 201 is adapted to generate acoustic data or sets of acoustic data, such as after a biological specimen has been immersed within a fluid, e.g., one or more fixative solutions. In some embodiments, the acoustic data is generated by (i) transmitting an acoustic signal such that the acoustic signal encounters a biological specimen immersed in a fluid (such as any of the fixatives described herein or those described in U.S. Publication No. 2017/0336363, the disclosure of which is incorporated by reference herein in its entirety), and (ii) detecting the acoustic signal after the acoustic signal has encountered the biological specimen. In some embodiments, acoustic data is repeatedly and/or continuously acquired and/or generated (e.g., every 0.2 seconds, every 0.5 seconds, every 1 second, every 5 seconds, every 10 seconds, every 20 seconds, every 30 seconds, every 60 seconds, etc.). In some embodiments, the acoustic data is repeatedly and/or continuously acquired and/or generated at a single point within the biological specimen. In other embodiments, the acoustic data is repeatedly and/or continuously acquired and/or generated along a plurality of points within or along the biological specimen, e.g., 2 or more points, 3 or more points, 4 or more points, 5 or more points, 6 or more points, 10 or more points, etc.

In some embodiments, the signal acquisition module 201 generates acoustic data through a frequency sweep. As used herein, the term "frequency sweep" refers to a series of acoustic waves transmitted at fixed intervals of frequencies through a medium (e.g., a medium comprising one or more fixatives), such that a first set of acoustic waves is emitted through the medium at a fixed frequency for a first fixed duration of time, and subsequent sets of acoustic waves are emitted at fixed frequency intervals for subsequent durations. In some embodiments, the durations are equal durations.

In some embodiments, the signal acquisition module 201 comprises one or more transmitters and receivers, wherein the one or more transmitters and receivers are arranged such that acoustic signals generated by the transmitter are received by the receiver and transformed into a computer-readable signal. In some embodiments, the signal acquisition module 201 comprises an ultrasonic transmitter and an ultrasonic receiver. As used herein, a "transmitter" is a device capable of converting an electrical signal to acoustic energy, and an "ultrasonic transmitter" is a device capable of converting an electrical signal to ultrasonic acoustic energy. As used herein, a "receiver" is a device capable of converting an acoustic wave to an electrical signal, and an "ultrasonic receiver" is a device capable of converting ultrasonic acoustic energy to an electrical signal."

Certain materials useful for generating acoustic energy from electrical signals are also useful for generating electrical signals from acoustic energy. Thus, the transmitter and receiver do not necessarily need to be separate components, although they can be. In some embodiments, the transmitter and receiver are arranged such that the receiver detects acoustic waves generated by the transmitter after the transmitted waves have encountered a material of interest, e.g., a biological specimen. In some embodiments, the receiver is arranged to detect acoustic waves that have been reflected by the material of interest, e.g., the biological specimen. In other embodiments, the receiver is arranged to detect acoustic waves that have been transmitted through the material of interest, e.g., the biological specimen. In some embodiments, at least two sets of transmitters and receivers are provided, wherein at least one set of the at least two sets is positioned to transmit an acoustic signal through the fluid (e.g., fixative solution) and the biological specimen, and at least a second positioned to transmit an acoustic signal through the fluid (e.g., fixative solution), but not through the biological specimen. In this embodiment, the first set is used to measure TOF changes in the biological specimen, and the second set is used to detect changes in TOF through the fluid (e.g., fixation solution) (for example, changes resulting from environmental fluctuations, such as temperature).

In some embodiments, the transmitter comprises a waveform generator operably linked to a transducer, the waveform generator for generating an electrical signal that is communicated to the transducer, the transducer for converting the electrical signal to an acoustic signal. In certain embodiments, the waveform generator is programmable, such that a user may modify certain parameters of the frequency sweep, including for example: starting and/or ending frequency, the step size between frequencies of the frequency sweep, the number of frequency steps, and/or the duration for which each frequency is transmitted. In other embodiments, the waveform generator is pre-programmed to generate one or more pre-determined frequency sweep patterns. In other embodiments, the waveform generator may be adapted to transmit both pre-programmed frequency sweeps and customized frequency sweeps. In some embodiments, the transmitter may also contain a focusing element, which allows the acoustic energy generated by the transducer to be predictably focused and directed to a specific area.

In operation, the transmitter transmits a frequency sweep through the medium, which is then detected by the receiver and transformed into the acoustic data set to be stored in a non-transitory computer readable storage medium and/or transmitted to the signal analyzer for analysis. Where the acoustic data set (e.g., physical acoustic waves) includes data representative of a phase difference between the transmitted acoustic waves and the received acoustic waves, the acoustic monitoring system may also include a phase comparator, which generates an electrical signal that corresponds to the phase difference between transmitted and received acoustic waves. In some embodiments, the acoustic monitoring system comprises a phase comparator communicatively linked to a transmitter and receiver. In those embodiments where the output of the phase comparator is an analog signal, the signal acquisition module 201 may also include an analog to digital converter for converting the analog output of the phase comparator to a digital signal. In some embodiments, digital signal may then be recorded, for example, on a non-transitory computer readable medium (memory 201 or storage subsystem 240) or may be communicated directly to the signal processing module 202 for analysis.

In some embodiments, the acoustic data is representative of at least a portion of a frequency sweep that is detected after the frequency sweep encounters the biological specimen. In some embodiments, the portion of the frequency sweep that is detected constitutes acoustic waves that are reflected by the biological specimen. In other embodiments, the portion of the frequency sweep that is detected constitutes acoustic waves that have passed through the biological specimen.

In some embodiments, acoustic data may be acquired by the signal acquisition module 201 at a single point in the biological specimen (for example, at or near the geometric center of the tissue sample). In other embodiments, the acoustic data may be captured at a plurality of positions within the biological specimen (e.g., equally spaced position intervals). In embodiments in which acoustic data is collected form a plurality of positions within the tissue sample, an apparatus may be provided for translating the tissue sample relative to the transmitter and receiver or translating the transmitter and receiver relative to the tissue sample, such that the common foci of the transmitter and receiver moves to different positions on the biological specimen. In some embodiments, the signal acquisition module 201 may be fitted with a plurality of transmitters and receivers, each of the plurality having a different common foci, such that each set captures acoustic data at a different location within the biological specimen.

United States Patent Publication No. 2017/0284859 further describes methods of capturing acoustic data across a plurality of different positions and, additionally, describes movable cassette holders to acquire such acoustic data. For example, the "different positions" may be a position within or on the surface of the tissue sample. According to some embodiments, the sample may be positioned at different "sample positions" by a relative movement of biopsy capsule and acoustic beam path. The relative movement may comprise moving the receiver and/or the transducer for "scanning" over the sample in a stepwise or continuous manner. Alternatively, the cassette may be repositioned by means of a movable cassette holder. For example, to image all the tissue in the cassette, the cassette holder may be sequentially raised ≈1 mm vertically and TOF values acquired at each new position. A "cassette" as used herein refers to, for example, a container for a biopsy capsule or a tissue sample not contained within a biopsy capsule. Preferentially, the cassette is designed and shaped such that it can automatically be selected and moved, e.g., raised and lowered, relative to the beam path of an ultrasonic transmitter-receiver pair, and further has openings that permit movement of a liquid reagent into and out of the cassette and thus further into and out of a tissue sample held within. The movement may be performed for example by a robotic arm or another automated movable component of a device onto which the cassette is loaded. In other embodiments, a cassette alone is use for containing a tissue sample and the shape of the cassette can, at least in part, determine the shape of the tissue sample. For example, placing a rectangular tissue block that is slightly thicker that the depth of a cassette into a cassette and closing the cassette lid can cause the tissue sample to be compressed and spread to fill a greater portion of the inner space of the cassette, and thus be transformed into a thinner piece having a greater height and width, but having a thickness corresponding roughly to the depth of the cassette. The disclosures of United States Patent Publication No. 2017/0284859 are hereby incorporated by reference herein in their entireties.

Yet other vessels for holding biological specimens during diffusion of a fluid or during fixation are described in PCT Publication No. WO/2011/071727, the disclosure of which is hereby incorporated by reference herein in its entirety. In some embodiments, the biological specimen is provided within a biopsy capsule. A "biopsy capsule" as used herein is, for example, a container for a biopsy tissue sample. Typically, a biopsy capsule comprises a mesh for holding the sample and letting a liquid reagent, e.g., a buffer, a fixation solution or a staining solution surround and diffuse into a tissue sample. A biopsy capsule can maintain the sample in a particular shape, which shape can advantageously provide the sample with a shape that is computationally easier to model according to the disclosed method and thus be more suitable for use in a disclosed system.

In some embodiments, a fixative solution may be held at a specific temperature or within a specific range of temperatures during at least a portion of the diffusion process (such as during a two-temperature fixation process as discussed in more detail below). In some embodiments, the apparatus for holding the volume of fixative may be adapted to maintain the fixative solution at the specific temperature or within the specific temperature range. In some embodiments, the apparatus may be insulated to substantially reduce heat transfer between the fixative solution and the surrounding environment. In some embodiments, the apparatus may be configured with a heating or cooling device designed to hold the fixative solution in which the tissue sample is immersed at the specific temperature or within the specific temperature range.

In some embodiments, the systems and methods incorporate a two-temperature immersion fixation method on a biological specimen. As used herein, a "two-temperature fixation method" is a fixation method in which tissue is first immersed in cold fixative solution for a first period of time, followed by heating (passively or actively) the biological specimen for the second period of time. The "cold" diffusion step permits the fixative solution to diffuse throughout the tissue without substantially causing cross-linking. In some embodiments, the temperature of the fixative solution is held at the cold temperature at least long enough to ensure that the fixative has diffused throughout the tissue sample. In some embodiments, the minimum amount of time to allow diffusion can be determined empirically using various time and temperature combinations in cold fixatives and evaluating the resulting tissue samples looking at factors, such as preservation of tissue architecture and loss of for preservation of a target analyte by immunohistochemistry (if the analyte is a protein or phosphorylated protein, for example) or in situ hybridization (if the target analyte is a nucleic acid, such as miRNA or mRNA). Alternatively, the minimum amount of time of time to allow for diffusion can be determined by monitoring diffusion using, for example, a method as outlined in Bauer et al., Dynamic Subnanosecond Time-of-Flight Detection for Ultra-precise Diffusion Monitoring and Optimization of Biomarker Preservation, Proceedings of SPIE, Vol. 9040, 90400B-1 (2014 Mar. 20).

In some embodiments, the systems and methods described herein may be utilized to estimate a time to which the cold fixative is optimally diffused into a biological specimen (such as the center of a biological specimen) (and prior to fixation at a comparatively higher temperature, such as at least at room temperature). Then, once the tissue has adequately diffused throughout the tissue, the heating (or allowing the biological specimen and/or fluid to warm to room temperature) step leads to cross-linking by the fixative. In some embodiments, the systems and methods described herein may be utilized to determine a time to fixation during this second step of a two-temperature immersion fixation method.

The combination of a cold diffusion followed by a heating step (passive or active heating) leads to a tissue sample that is more completely fixed than by using standard methods. Thus, in an embodiment, a tissue sample is fixed by: (1) immersing an unfixed tissue sample in a cold fixative solution and monitoring diffusion of the fixative into the tissue sample by monitoring TOF in the tissue sample using the systems and methods as disclosed herein (diffusion step); and (2) allowing the temperature of the tissue sample to raise after a threshold TOF has been measured (fixation step). In some embodiments, the diffusion step is performed in a fixative solution that is below about 20° C., below about 15° C., below about 12° C., below about 10° C., below about 8° C., below about 6° C., below about 4° C., in the range of about 0° C. to about 10° C., in the range of about 0° C. to about 12° C., in the range of about 0° C. to about 15° C., in the range of about 2° C. to about 10° C., in the range of about 2° C. to about 12° C., in the range of about 2° C. to about 15° C., in the range of about 5° C. to about 10° C., in the range of about 5° C. to about 12° C., in the range of about 5° C. to about 15° C. In some embodiments, a diffusion step may be performed at any of the above temperatures, and the sample may be stored in the fixative for a time period between up to about 72 hours at a temperature below about 20° C., such as below about 15° C., or such as below about 10° C. In other embodiments, the temperature of the fixative solution surrounding the tissue sample is allowed to rise within the range of about 20° C. to about 55° C., such as within the range of about 20° C. to about 50° C., such as within the range of about 20° C. to about 45° C., such as within the range of about 20° C. to about 40° C., such as within the range of about 250° C. to about 55° C., such as within the range of about 25° C. to about 50° C., such as within the range of about 25° C. to about 45° C., or such as within the range of about 25° C. to about 50° C. during the fixation step. Methods for the fixation of a biological specimen, including methods incorporate a two-temperature fixation protocol, are further described in United States Patent Publication No. 2012/0214195, the disclosure is incorporated by reference herein in its entirety.

In some embodiments, two-temperature fixation processes are especially useful for methods of detecting certain labile biomarkers in tissue samples, including, for example, phosphorylated proteins, DNA, and RNA molecules (such as miRNA and mRNA). See PCT/EP2012/052800 (incorporated herein by reference). Thus, in certain embodiments, the fixed tissue samples obtained using these methods can be analyzed for the presence of such labile markers. In some embodiments, a method of detecting a labile marker is a sample is provided, the method comprising fixing the tissue according to a two-temperature fixation as disclosed herein and contacting the fixed tissue sample with an analyte binding entity capable of binding specifically to the labile marker, such as FOXP3. Examples of analyte-binding entities include: antibodies and antibody fragments (including single chain antibodies), which bind to target antigens; t-cell receptors (including single chain receptors), which bind to MHC:antigen complexes; MHC: peptide multimers (which bind to specific T-cell receptors); aptamers, which bind to specific nucleic acid or peptide targets; zinc fingers, which bind to specific nucleic acids, peptides, and other molecules; receptor complexes (including single chain receptors and chimeric receptors), which bind to receptor ligands; receptor ligands, which bind to receptor complexes; and nucleic acid probes, which hybridize to specific nucleic acids. For example, an immunohistochemical method of detecting a phosphorylated protein in a tissue sample is provided, the method comprising contacting the fixed tissue obtained according to the foregoing two-temperature fixation method with an antibody specific for the phosphorylated protein and detecting binding of the antibody to the phosphorylated protein. In some embodiments, an in situ hybridization method of detecting a nucleic acid molecule is provided, the method comprising contacting the fixed tissue obtained according to the foregoing two-temperature fixation method with a nucleic acid probe specific for the nucleic acid of interest and detecting binding of the probe to the nucleic acid of interest.

Signal Processing Module

The system 200 of the present disclosure further includes a signal processing module 202. In some embodiments, the signal processing module 202 is part of the signal acquisition module 201. In other embodiments, the signal processing module 202 is separate from the signal acquisition module 201.

In either embodiment, the signal processing module 202 receives acoustic data from the signal acquisition module 201 (or from a memory 201 or storage subsystem 240 in communication therewith) and processes that received acoustic data to generate one TOF data points, one or more TOF curves, and/or one or more decay constants (collectively referred to herein as "TOF data"). In some embodiments, acoustic data is continuously generated (such as predetermined intervals of time) and the signal processing module 202 processes the acoustic data as it is received, thereby providing TOF data as acoustic data is continuously acquired. In some embodiments, the signal processing module 202 processes the acoustic data in real-time as it is received from the signal acquisition module 201.

In some embodiments, the signal processing module 202 utilizes the retrieved acoustic data as input to compute one or more TOF data points. In some embodiments, a "TOF data point" is the TOF differential between the bulk fluid and a biological specimen at one time point. In some embodiments, each collected TOF data point is representative of a computed differential in transit time of acoustic waves between (i) a calculated absolute transit time for acoustic waves to travel through a fluid; and (ii) a calculated absolute transit time for acoustic waves to travel through both a fluid and a biological specimen, as described further herein below.

In other embodiments, the signal processing module 202 utilizes the retrieved acoustic data and/or computed TOF data points as input to compute a "TOF curve," which includes a vector of "TOF data points" collected over time. In some embodiments, the TOF curve describes the diffusion of the exogenous fluid into the biological specimen over a course of time and up to a specific point in time (namely, the point in time in which the last TOF data point was collected). As more TOF data points are collected over time, new TOF curves may be computed, including the "new" TOF data points. In some embodiments, the signal processing module 202 includes instructions to fit a derived TOF curve to a single exponential curve.

In yet other embodiments, the signal processing module 202 includes instructions to compute a decay constant or an average decay constant ($\tau_{avg}$) based on the received acoustic data and/or TOF data points. The operations performed by the signal processing module 202 are described further herein.

In some embodiments, the one or more TOF data points, the one or more TOF curves, and/or the one or more computed decay constants are provided as output to the signal modeling module 203 and/or the prediction module 204. In some embodiments, the one or more TOF data points, the one or more TOF curves, and/or the one or more computed decay constants are stored in a memory 201 or a storage subsystem 240 such that they may be retrieved as input by either the signal modeling module 203 or the prediction module 204.

Received Acoustic Data

In some embodiments, the signal processing module 202 utilizes retrieved acoustic data to calculate an absolute amount of time acoustic waves take to travel between transducers ("absolute transit time") within the signal acquisition module 201. In some embodiments, the absolute transit time is an absolute transit time for acoustic waves to travel through a fluid as measured between a transmitter and a receiver. In other embodiments, the absolute transit time is an absolute transit time for acoustic waves to travel through a fluid and a biological specimen (e.g., a biological specimen disposed within a histological cassette) as measured between a transmitter and a receiver.

In some embodiments, the signal processing module 202 further utilizes the calculated absolute transit times to calculate how much faster the acoustic waves travel through the fluid alone as opposed to traveling through the fluid and the biological specimen. In these embodiments, the differential in transit time is computed between (i) a calculated absolute transit time for acoustic waves to travel through a fluid, and (ii) a calculated absolute transit time for acoustic waves to travel through a fluid and a biological specimen. In some embodiments, this process is repeated over time. In other embodiments, this process is continuously repeated as new data is acquired by the signal acquisition module 201, such that the signal processing module 202 computes in real-time data received from the signal acquisition module 201. In some embodiments, new data is received from the signal acquisition module 201 at least once every 0.5 seconds. In some embodiments, new data is received from the signal acquisition module 201 at least once every 1 second. In some embodiments, new data is received from the signal acquisition module 201 at least once every 1.5 seconds. In some embodiments, new data is received from the signal acquisition module 201 at least once every 2 seconds. In some embodiments, new data is received from the signal acquisition module 201 at least once every 5 seconds. In some embodiments, new data is received from the signal acquisition module 201 at least once every 10 seconds. In some embodiments, new data is received from the signal acquisition module 201 at least once every 15 seconds. In some embodiments, new data is received from the signal acquisition module 201 at least once every 20 seconds. In some embodiments, new data is received from the signal acquisition module 201 at least once every 30 seconds. In some embodiments, new data is received from the signal acquisition module 201 at least once every 40 seconds. In some embodiments, new data is received from the signal acquisition module 201 at least once every 50 seconds. In some embodiments, new data is received from the signal acquisition module 201 at least once every 60 seconds.

In some embodiments, the differentials computed over time represent a change in TOF. In some embodiments, changes in the biological specimen (e.g., the state of fixation of the biological specimen as that biological specimen becomes fixed given exposure to a solution including one or more fixatives) over time may alter the computed differential. For instance, the acoustic waves may travel faster through the biological specimen over time as it is fixed within a fluid including one or more fixatives. Based on this, and in some embodiments, the differential computed over time may help predict the fixation status of the biological specimen, the change in fixation status over time, or may be used to predict an amount of time in which fixation must continue before the biological specimen is adequately fixed.

TOF Data Point Computation

In some embodiments, the signal processing module 202 is used to compute one or more TOF data points. In some embodiments, TOF is estimated by the signal processing module 202 by comparing the phase of transmitted and received acoustic waves. In some embodiments, an experimental frequency sweep is transmitted by a transmitter through the medium and detected by a receiver. In some embodiments, the phase of the transmitted and received waves is compared and transformed to a temporal phase shift. In some embodiments, a simulation is then run to model candidate temporal phase shifts at a variety of candidate TOFs, and an error between the candidate and experimental temporal phase shifts is generated and plotted as an error function. In some embodiments, the TOF resulting in the minimum of the error function is selected as the "observed" TOF. In some embodiments, TOF is calculated by recording a transmitted phase shift between a transmitted and received ultrasound signal and by fitting the recorded phase shift to a plurality of simulated phase shifts at different candidate TOFs.

In some embodiments, TOF is calculated using (i) an envelope method of TOF calculation; (ii) linear regression method of calculating TOF; or (iii) a curve fitting method of TOF calculation. Each of the envelope method of TOF calculation; the linear regression method of calculating TOF; and the curve fitting method of TOF calculation are described below and further described in PCT Publication No. WO/2016/097164, the disclosure of which is hereby incorporated by reference herein in its entirety.

Envelope Method of TOF Calculation

In an envelope method of TOF calculation, TOF is based on an envelope of a minimum of a calculated error function. To calculate the envelope, an error function must first be generated. Error function generation generally requires comparison between: (1) a temporal phase shift generated from a recorded frequency sweep; and (2) a plurality of candidate temporal phase shifts simulated based on a plurality of candidate TOFs. This is repeated for each frequency of the frequency sweep. An error between the observed temporal phase shifts and each of the candidate temporal phase shifts is calculated and plotted as the error function. An envelope function is then applied to the error function. The minimum of the envelope function is selected as the observed TOF.

Linear Regression Method of Calculating TOF

A linear regression method of calculating TOF calculates the TOF signal seeking out the individual linear sections of an ultrasound frequency sweep, performing a linear regression to each region, and averaging the slopes of each region to determine the true TOF. This may be contrasted with the previous embodiment in which the ideal phase of the frequency sweep was determined to find the ideal frequency, with the slope of that frequency being reconstructed and equated to the TOF, whereas in this embodiment, the slopes of the phase frequency sweep are directly computed.

Curve Fitting Method of TOF Calculation

The "curve fitting method" of calculating TOF exploits the linearity of the accumulated phase comparison through a frequency sweep. The TOF between two ultrasound transducers can be calculated by the slope of a phase-frequency curve obtained for the frequency sweep. However, as a full cycle is accumulated the phase returns to 0 so the phase versus ultrasound frequency looks like a triangle wave. This algorithm produces a candidate triangle wave with a given amplitude, frequency, and phase. The candidate triangle wave's amplitude, frequency and phase are varied and compared against the experimentally detected triangle from the frequency sweep. The closest match between candidate and experimental waves is then used to directly calculate the observed TOF using the known relationship between a triangle wave's frequency and the absolute value of its slope. The slope is then used to calculate TOF.

As an example of TOF calculation, Applicant has developed a method capable of robustly detecting sub-nanosecond TOF values in tissue samples immersed in a fluid, e.g., one or more fixatives. In some embodiments, a transmitting transducer programmed with a programmable waveform generator transmits a 3.7 MHz sinusoidal signal for 600 μs. In some embodiments, that pulse train is detected by a receiving transducer after traversing the fluid and tissue, and the received and transmitted ultrasound sinusoids are then compared electronically with a digital phase comparator. In some embodiments, the output of the phase comparator is queried with an analog to digital converter and the average recorded. In some embodiments, the process is repeated at multiple acoustic frequencies (v). In some embodiments, given the central frequency (about 4.0 MHz) and fractional bandwidth (about 60%) of the transducers, a typical sweep ranges from about 3.7 to about 4.3 MHz with the phase comparator queried every about 600 Hz. In some embodiments, the voltage from the phase comparator is converted to a temporal phase shift, referred to as the experimentally determined phase ($\varphi_{exp}$). Next, a brute force simulation is used to calculate what the observed phase frequency sweep would look like for different TOF values. In some embodiments, candidate temporal phase values, as a function of input sinusoid frequency, are calculated according to Equation 1:

$$\varphi_{cand}(TOF_{cand}, v) = \left| TOF_{cand} - rnd\left(\frac{TOF_{cand}}{T(v)}\right)T(v) \right|, \tag{1}$$

where $TOF_{cand}$ is a candidate TOF value in nanoseconds, T is the period of the input sinusoid in nanoseconds, rnd represents the round to the nearest integer function, and | . . . | is the absolute value symbol. In some embodiments, for a given candidate TOF and frequency value (i.e., period), the term on the right represents how long it takes for the nearest number of cycles to occur. In some embodiments, this value is subtracted from $TOF_{cand}$ to calculate the temporal phase, into or up to, the next complete cycle. In some embodiments, phase values are thus computed for multiple candidate TOF values initially ranging from 10-30 μs with 200 μs spacing. In some embodiments, the error between experimental and candidate frequency sweeps is calculated in a least-squares sense for individual candidate TOF values by Equation 2:

$$\text{Error}(TOF_{cand}) = \sum_{v=1}^{N} (\varphi_{cand}(TOF_{cand}, v) - \varphi_{exp}(v)), \tag{2}$$

where N is the total number of frequencies in the sweep. In some embodiments, the normalized error function, as a function of candidate TOF, resembles an optical interferogram. For example, each feature has a width of one acoustic period (T=¼ MHz=250 ns). Maximum error function indicates the candidate phase frequency sweep has equal wavelength but is out of phase with the experimental phase frequency sweep. Conversely, when error is minimized the two are completely harmonized and thus the reconstructed TOF is registered as the global minimum of the error function according to Equation 3:

$$TOF_{recon} = \underset{TOF_{cond}}{\arg\min}(\text{Error}). \tag{3}$$

In some embodiments, this technique of digitally comparing acoustic waves results in high precision due to the sharpness of the center trough, and results in exceptionally well-matched candidate and experimental phase frequency sweeps.

In some embodiments, TOF data points are continuously computed as new acoustic data is received and processed by the signal processing module 202 (e.g., every 0.2 seconds, every 0.5 seconds, every 1 second, every 5 seconds, every 10 seconds, every 20 seconds, every 30 seconds, every 60 seconds, etc.). In some embodiments, the TOF data points are stored in a memory 201 and/or in a storage subsystem 240 in communication with the signal processing module 202. In some embodiments, the TOF data points, or TOF curves, are provided as input to the signal modeling module 203 and/or the prediction module 204.

Rate of Diffusion and Decay Constant Computation

In some embodiments, the signal processing module 202 is adapted to compute a rate of diffusion and/or a decay constant. In some embodiments, the computed decay constant is provided as input to the signal modeling module 203 and/or the prediction module 204. In some embodiments, in order to calculate the rate of diffusion, a TOF curve is fit to a single exponential curve to derive a TOF decay amplitude (A) and decay constant (τ). In some embodiments, the single exponential curve is of the form according to Equation (4):

$$TOF(t,r)=C(r)+Ae^{-t/\tau(r)} \tag{4},$$

wherein C is a constant offset, A is the amplitude of the decay (i.e., the TOF value difference between the undiffused and fully diffused tissue sample), τ is the decay constant, t is the diffusion time, and r is the spatial dependence (which is explicitly stated). In some embodiments, the constant offset C represents the TOF difference between the tissue sample and a bulk solution (e.g., a tissue fluid or a sample buffer). In some embodiments, the constant C may be set to zero for visualization.

In embodiments where acoustic data is collected at a plurality of spatial locations within or along the biological specimen, it may be desirable to calculate a spatially averaged TOF curve (i.e., a single curve representing TOF at a plurality of spatial locations within the sample) and to obtain an average TOF amplitude ($A_{avg}$) and an average decay constant ($\tau_{avg}$) by fitting the spatially averaged TOF curve to a single exponential curve. In some embodiments, the spatially averaged TOF curve is fit to a single exponential curve of the form according to Equation (5):

$$TOF_{avg}(t) = \sum_{r=1}^{N} TOF(t, r) = C_{avg} + A_{avg}e^{-t/\tau_{avg}}, \tag{5}$$

wherein $TOF_{avg}$ is the spatially-averaged TOF curve, N is the number of spatial locations at which a TOF curve was acquired, $C_{avg}$ is the average constant offset, $A_{avg}$ is the average amplitude of the decay (i.e., the average TOF value difference between the undiffused and fully diffused tissue sample), and $\tau_{avg}$ is the average decay constant. In this context means, "average" means a "spatial average" having been derived from data values obtained for a particular, shared time point at different points in the sample.

In some embodiments, the rate of diffusion at time t is calculated as a derivative of the single exponential curve at time t. In some embodiments, the rate of diffusion for a non-spatially averaged TOF curve is calculated according to the Equation (6):

$$\frac{dTOF(t)}{dt(t = t_o)} = \frac{-A}{\tau}e^{-t_o/\tau} \tag{6}$$

wherein A is the amplitude of the decay (i.e., the TOF value difference between the undiffused and fully diffused tissue sample), τ is the decay constant, and $t_0$ is the diffusion time. In some embodiments, the rate of diffusion for a spatially averaged TOF curve is calculated according to Equation (7):

$$\frac{dTOF(t)}{dt(t = t_o)} = \frac{-A_{avg}}{\tau_{avg}} e^{-t_o/\tau_{avg}} \qquad (7)$$

wherein $A_{avg}$ is the average amplitude of the decay (i.e., the spatial average of the TOF difference between undiffused and fully diffused tissue sample), $\tau_{avg}$ is the average decay constant, and $t_0$ is the diffusion time. In some embodiments, the rate of diffusion calculated as an amplitude-normalized rate of diffusion by dividing the derivative of the curve by the sample's amplitude (A or $A_{avg}$) at time $t_0$. In some embodiments, the amplitude-normalized rate of diffusion is calculated for a non-spatially averaged TOF curve according to Equation (8):

$$\dot{m}(t = t_o) = 100\left(\frac{-1}{\tau} e^{-t_o/\tau}\right), \left[\frac{\%}{\text{time}}\right], \qquad (8)$$

wherein $\tau$ is the decay constant, $t_0$ is the diffusion time, and the brackets indicate the units for rate of diffusion, wherein time is the units of time according to $\tau$. In some embodiments, the amplitude-normalized rate of diffusion is calculated for a spatially averaged TOF curve according to Equation (9):

$$\dot{m}(t = t_o) = 100\left(\frac{-1}{\tau_{avg}} e^{-t_o/\tau_{avg}}\right), \left[\frac{\%}{\text{time}}\right], \qquad (9)$$

wherein $\tau_{avg}$ is the average decay constant, $t_0$ is the diffusion time, and the brackets indicate the units for rate of diffusion, wherein time is the units of time according to $\tau_{avg}$.

In some embodiments, decay constants are continuously computed as new acoustic data is received and processed by the signal processing module 202 (e.g., every 0.2 seconds, every 0.5 seconds, every 1 second, every 5 seconds, every 10 seconds, every 20 seconds, every 30 seconds, every 60 seconds, etc.). In some embodiments, the computed decay constants are stored in a memory 205 and/or in a storage subsystem 240 in communication with the signal processing module 202. In some embodiments, the computed decay constants, or averages thereof, are provided as input to the signal modeling module 203 and/or the prediction module 204.

Additional methods of deriving TOF data are described in U.S. Publication Nos. 2017/0284920, 2017/0284859, and 2017/0284969, the disclosures of which are hereby incorporated by reference herein in their entireties.

Signal Modeling Module

The system 200 also includes a signal modeling module 203 to assess whether a measured TOF signal accurately reflects the actual rate of diffusion of a fluid (e.g., one or more fixatives) through a biological specimen. In some embodiments, the signal modeling module 203 receives TOF data (e.g., a predetermined number of TOF data points, derived TOF curves, and/or computed decay constants) from the signal processing module 202 or a memory 205 or storage subsystem 240 in communication therewith and computes at least two different confidence models (step 403). In some embodiments, the computed at least two different confidence models are a past confidence model and a present confidence model, as described herein. In other embodiments, the computed at least two different confidence models are the past confidence model and the future confidence model. In other embodiments, the computed at least two different confidence models are the present confidence model and the future confidence model. In other embodiments, the signal modeling module 203 computes three different confidence models (step 403). In some embodiments, the three computed different confidence models include a past confidence model, a present confidence model, and a future confidence model, as described herein.

In some embodiments, once the at least two confidence models are computed (step 403), each of the at least two confidence models are independently compared with predetermined threshold criteria to determine whether the confidence models are each independently "satisfied" (step 404). In some embodiments, once the at least two confidence models are computed and once the at least two confidence models are independently and/or simultaneously satisfied (step 404), a time in which a fluid is optimally diffused through a biological specimen or a time to fixation (step 405) is estimated using the prediction module 204. In some embodiments, the time in which a fluid is optimally diffused through a biological specimen or the time to fixation is estimated using TOF data corresponding to the point in time in which the at least two confidence models were independently and/or simultaneously were satisfied.

In other embodiments, three confidence models are computed (step 403) and once the at least two confidence models of the three computed confidence models are satisfied (step 404), a time in which a fluid is optimally diffused through a biological specimen or a time to fixation is estimated using the prediction module 204. In some embodiments, the time in which a fluid is optimally diffused through a biological specimen or the time to fixation is estimated using TOF data corresponding to the point in time in which the at least two confidence models (of the three computed confidence models) were independently and/or simultaneously were satisfied.

In yet other embodiments, three confidence models are computed (step 403) and once all three confidence models independently and/or simultaneously satisfied (step 404), a time in which a fluid is optimally diffused through a biological specimen or a time to fixation is estimated (step 405) using the prediction module 204. In some embodiments, the time in which a fluid is optimally diffused through a biological specimen or the time to fixation is estimated using TOF data corresponding to the point in time in which the three confidence models were independently and/or simultaneously were satisfied.

Each of the different confidence models and examples of predetermined threshold criteria to independently "satisfy" the different confidence models are described further herein. Example time courses illustrating the past, present, and future confidence models and their predictive power are described in Example 1 and illustrated in FIGS. 5-9.

In some embodiments, after each new successive TOF data point is derived by the signal processing module 202 and received by the signal modeling module 203, each of the confidence models are updated (recomputed) based on the newly received TOF data point. In some embodiments, at least two confidence models are continuously recomputed as new TOF data is received as input (e.g., every 0.2 seconds, every 0.5 seconds, every 1 second, every 5 seconds, every 10 seconds, every 20 seconds, every 30 seconds, every 60 seconds, etc.). In other embodiments, each of three confidence models are continuously recomputed as new TOF data is received as input (e.g., every 0.2 seconds, every 0.5 seconds, every 1 second, every 5 seconds, every 10 seconds, every 20 seconds, every 30 seconds, every 60 seconds, etc.).

In some embodiments, new TOF data is received at least once every 0.2 seconds and each of the confidence models are then recomputed with the newly received TOF data (e.g., with a newly received TOF data point). In some embodiments, new TOF data is received at least once every 0.5 seconds and each of the confidence models are then recomputed with the newly received TOF data. In some embodiments, new TOF data is received at least once every 0.7 seconds and each of the confidence models are then recomputed with the newly received TOF data. In some embodiments, new TOF data is received at least once every 1 second and each of the confidence models are then recomputed with the newly received TOF data. In some embodiments, new TOF data is received at least once every 1.5 seconds and each of the confidence models are then recomputed with the newly received TOF data. In some embodiments, new TOF data is received at least once every 2 seconds and each of the confidence models are then recomputed with the newly received TOF data. In some embodiments, new TOF data is received at least once every 3 seconds and each of the confidence models are then recomputed with the newly received TOF data. In some embodiments, new TOF data is received at least once every 4 seconds and each of the confidence models are then recomputed with the newly received TOF data. In some embodiments, new TOF data is received at least once every 5 seconds and each of the confidence models are then recomputed with the newly received TOF data. In some embodiments, new TOF data is received at least once every 10 seconds and each of the confidence models are then recomputed with the newly received TOF data.

In some embodiments, new TOF data is received at least once every 15 seconds and each of the confidence models are then recomputed with the newly received TOF data. In some embodiments, new TOF data is received at least once every 20 seconds and each of the confidence models are then recomputed with the newly received TOF data. In some embodiments, new TOF data is received at least once every 25 seconds and each of the confidence models are then recomputed with the newly received TOF data. In some embodiments, new TOF data is received at least once every 30 seconds and each of the confidence models are then recomputed with the newly received TOF data. In some embodiments, new TOF data is received at least once every 35 seconds and each of the confidence models are then recomputed with the newly received TOF data. In some embodiments, new TOF data is received at least once every 40 seconds and each of the confidence models are then recomputed with the newly received TOF data. In some embodiments, new TOF data is received at least once every 45 seconds and each of the confidence models are then recomputed with the newly received TOF data. In some embodiments, new TOF data is received at least once every 50 seconds and each of the confidence models are then recomputed with the newly received TOF data. In some embodiments, new TOF data is received at least once every 55 seconds and each of the confidence models are then recomputed with the newly received TOF data. In some embodiments, new TOF data is received at least once every 60 seconds and each of the confidence models are then recomputed with the newly received TOF data. In some embodiments, new TOF data is received at least once every 65 seconds and each of the confidence models are then recomputed with the newly received TOF data.

In some embodiments, new TOF data is received at least once every 70 seconds and each of the confidence models are then recomputed with the newly received TOF data. In some embodiments, new TOF data is received at least once every 80 seconds and each of the confidence models are then recomputed with the newly received TOF data. In some embodiments, new TOF data is received at least once every 90 seconds and each of the confidence models are then recomputed with the newly received TOF data. In some embodiments, new TOF data is received at least once every 100 seconds and each of the confidence models are then recomputed with the newly received TOF data. In some embodiments, new TOF data is received at least once every 110 seconds and each of the confidence models are then recomputed with the newly received TOF data. In some embodiments, new TOF data is received at least once every 120 seconds and each of the confidence models are then recomputed with the newly received TOF data.

Past Confidence Model

The past confidence model determines whether a measured rate of diffusion of one or more fluids (including one or more fixatives) through a biological specimen has been consistently resolved by the TOF system. Said another way, the past confidence model is used to establish that a candidate TOF data point is consistent with one or more previously collected TOF data points. For example, the past confidence model may be used to establish that a candidate TOF data point recorded at, for instance, time interval 12, is consistent with collected TOF data points recorded at each of the time intervals 11, 10, 9, 8, 7, and 6.

Based on Fick's first law, it is expected that diffusion of a fluid (including one or more fixatives) through a biological specimen may be described by a single parameter, namely the diffusivity constant. In some embodiments, a biological specimen's diffusion can be characterized by a single exponential decay as governed by a computed decay constant (see, e.g., the decay constant computed using the signal processing module 202). In some embodiments, if the computed decay constant varies significantly over time (e.g., for successively received TOF data points received over time), it is indicative that the diffusion profile cannot converge to the "true" profile. Said another way, and in the context of the fixation of a biological specimen, wide variations in successive computed decay constants calculated over time (e.g. over a predetermined number of successively received TOF data points) is indicative that a calculated rate of diffusion does not yet represent a true rate of diffusion of fixative through a biological specimen; while a relatively consistent decay constant over time (e.g. over a predetermined number of successively received TOF data points) is indicative that a computed rate of diffusion is representative of a true rate of diffusion of fixative through the biological specimen.

In some embodiments, the past confidence model retrieves as input one or more derived TOF data points and/or one or more decay constants from the signal processing module 202 or a memory 201 or a storage subsystem 240 in communication therewith and determines whether the measured rate of diffusion has been consistently resolved within some predetermined threshold margin over a predetermined number of consecutively derived TOF data points. In some embodiments, a measured rate of diffusion must be consistently resolved within a predetermined threshold margin for 3 consecutively derived TOF data points. In other embodiments, a measured rate of diffusion must be consistently resolved within a predetermined threshold margin for 4 consecutively derived TOF data points. In yet other embodiments, a measured rate of diffusion must be consistently resolved within a predetermined threshold margin for 5 consecutively derived TOF data points. In further embodiments, a measured rate of diffusion must be consistently resolved within a predetermined threshold margin for 6 consecutively derived TOF data points. In yet further embodiments, a measured rate of diffusion must be consistently resolved within a predetermined threshold margin for 7 consecutively derived TOF data points. In even further embodiments, a measured rate of diffusion must be consistently resolved within a predetermined threshold margin for 8 consecutively derived TOF data points. In yet even further embodiments, a measured rate of diffusion must be consistently resolved within a predetermined threshold margin for 9 consecutively derived TOF data points. In other embodiments, a measured rate of diffusion must be consistently resolved within a predetermined threshold margin for 10 consecutively derived TOF data points. In yet other embodiments, a measured rate of diffusion must be consistently resolved within a predetermined threshold margin for 12 consecutively derived TOF data points. In further embodiments, a measured rate of diffusion must be consistently resolved within a predetermined threshold margin for 15 consecutively derived TOF data points. In yet further embodiments, a measured rate of diffusion must be consistently resolved within a predetermined threshold margin for 18 consecutively derived TOF data points. In even further embodiments, a measured rate of diffusion must be consistently resolved within a predetermined threshold margin for 21 consecutively derived TOF data points. In yet even further embodiments, a measured rate of diffusion must be consistently resolved within a predetermined threshold margin for 24 consecutively derived TOF data points.

In some embodiments, the computed past confidence model is satisfied (i.e., meets predetermined past confidence model threshold criteria) when a predetermined number of retrieved computed candidate decay constants corresponding to a plurality of consecutively derived TOF data points are each determined to be within a predetermined threshold percentage value of a calculated average decay constant. In some embodiments, one or more convergence testing algorithms are used to determine whether the computed candidate decay constants fall within or meet the predetermined past confidence model threshold criteria. In some embodiments, the convergence testing algorithms are selected from an absolute convergence, an alternative series test, a direct comparison test, an integral test, a limit comparison test, a p-series convergence, a ratio test, a root test, a Cauchy condensation test, Abel's test, a Dirichlet's test, a Raabe-Duhamel's test, a Bertrand's test, and a Gauss's test.

In some embodiments, the convergence testing comprises (i) computing a candidate decay constant of a candidate TOF data point to provide a "theoretical value;" (ii) calculating an average decay constant based on a predetermined number of computed decay constants corresponding to a predetermined number of TOF data points computed over time and preceding the candidate TOF data point to provide an "experimental value"; (iii) determining an actual percent error based on the computed theoretical value and the calculated experimental value; and (iv) comparing the determined percent error to a predetermined threshold percentage value. In some embodiments, the actual percent error is calculated by Equation (10):

$$\% \text{ Error} = ((\text{Calculated Theoretical Value} - \text{Computed Experimental Value})/\text{Calculated Theoretical Value}) \times 100 \quad (10)$$

In some embodiments, the average decay constant is derived by: (i) retrieving from a memory 202 or a storage subsystem 240, a computed a decay constant for each of a predetermined number of consecutively derived TOF data points preceding the candidate TOF data point; and (ii) averaging each of the retrieved computed decay constants. In some embodiments, the candidate TOF data point is a most recently received derived TOF data point; and the average decay constant is based on computed decay constants for a predetermined number of consecutively derived TOF data points preceding the candidate TOF data point. For instance, the candidate TOF data point may be at a time interval of 10, while the average decay constant is computed based on TOF data points acquired at time intervals 9, 8, 7, 6, and 5.

In some embodiments, the average decay constant is computed based on at least 2 TOF data points preceding the candidate TOF data point. In other embodiments, the average decay constant is computed based on at least 3 TOF data points preceding the candidate TOF data point. In other embodiments, the average decay constant is computed based on at least 4 TOF data points preceding the candidate TOF data point. In other embodiments, the average decay constant is computed based on at least 5 TOF data points preceding the candidate TOF data point. In other embodiments, the average decay constant is computed based on at least 6 TOF data points preceding the candidate TOF data point. In other embodiments, the average decay constant is computed based on at least 7 TOF data points preceding the candidate TOF data point. In other embodiments, the average decay constant is computed based on at least 8 TOF data points preceding the candidate TOF data point. In other embodiments, the average decay constant is computed based on at least 9 TOF data points preceding the candidate TOF data point. In other embodiments, the average decay constant is computed based on at least 10 TOF data points preceding the candidate TOF data point.

In some embodiments, the predetermined threshold percentage value is less than about 5%. In other embodiments, the predetermined threshold percentage value is less than about 4%. In yet other embodiments, the predetermined threshold percentage value is less than about 3%. In some embodiments, the predetermined threshold percentage value is between about 1% and about 3%. In other embodiments, the predetermined threshold percentage value is between about 1.5% and about 3%. In yet other embodiments, the predetermined threshold percentage value is between about 1.75% and about 2.5%. In further embodiments, the predetermined threshold percentage value is between about 1.75% and about 2.25%. In some embodiments, the predetermined threshold percentage value is about 2%.

In some embodiments, the past confidence model is satisfied when at least 5 computed candidate decay constants corresponding to at least 5 consecutively derived TOF data points are each within a predetermined threshold percentage value of a calculated average decay constant. In other embodiments, the past confidence model is satisfied when at least 6 computed candidate decay constants corresponding to at least 6 consecutively derived TOF data points are each within a predetermined threshold percentage value of a calculated average decay constant. In other embodiments, the past confidence model is satisfied when at least 7 computed candidate decay constants corresponding to at least 7 consecutively derived TOF data points are each within a predetermined threshold percentage value of a calculated average decay constant. In other embodiments, the past confidence model is satisfied when at least 8 computed candidate decay constants corresponding to at least 8 consecutively derived TOF data points are each within a predetermined threshold percentage value of a calculated average decay constant. In other embodiments, the past confidence model is satisfied when at least 9 computed candidate decay constants corresponding to at least 9 consecutively derived TOF data points are each within a predetermined threshold percentage value of a calculated average decay constant. In other embodiments, the past confidence model is satisfied when at least 10 computed candidate decay constants corresponding to at least 10 consecutively derived TOF data points are each within a predetermined threshold percentage value of a calculated average decay constant.

Present Confidence Model

The present confidence model is used to establish that there is a high statistical confidence to predict future TOF data points. While the past confidence model determines if the rate of diffusion across a predetermined number of consecutively derived TOF data points is consistent, the present confidence model establishes whether the current TOF data point is consistent with at least some of the previously collected TOF data, thus facilitating the elimination of false positives generated by the past confidence model. For instance, if the present confidence model computes the same decay constant repeatedly but with low confidence, the present confidence model would correctly determine that the signal was sufficiently valid to make a prediction on.

In some embodiments, the present confidence model establishes whether the current TOF data point is consistent with at least 20% of the previously collected TOF data. In some embodiments, the present confidence model establishes whether the current TOF data point is consistent with at least 30% of the previously collected TOF data. In some embodiments, the present confidence model establishes whether the current TOF data point is consistent with at least 40% of the previously collected TOF data. In some embodiments, the present confidence model establishes whether the current TOF data point is consistent with at least 50% of the previously collected TOF data. In some embodiments, the present confidence model establishes whether the current TOF data point is consistent with at least 60% of the previously collected TOF data. In some embodiments, the present confidence model establishes whether the current TOF data point is consistent with at least 70% of the previously collected TOF data. In some embodiments, the present confidence model establishes whether the current TOF data point is consistent with at least 80% of the previously collected TOF data. In some embodiments, the present confidence model establishes whether the current TOF data point is consistent with at least 90% of the previously collected TOF data. In some embodiments, the present confidence model establishes whether the current TOF data point is consistent with at least 95% of the previously collected TOF data. In some embodiments, the present confidence model establishes whether the current TOF data point is consistent with at least 98% of the previously collected TOF data. In some embodiments, the present confidence model establishes whether the current TOF data point is consistent with at least 99% of the previously collected TOF data. In some embodiments, the present confidence model establishes whether the current TOF data point is consistent with all of the previously collected TOF data.

In some embodiments, the present confidence model (i) retrieves as input a derived TOF curve (which includes some or all TOF data points up to the time in which the present confidence model is being computed) and/or one or more derived decay constants from the signal processing module 202 or a memory 201 or a storage subsystem 240 in communication therewith, (ii) computes a confidence interval based on the retrieved derived TOF curve and/or decay constants, and (iii) assesses whether a computed confidence interval is below a predetermined threshold value. For example, the present confidence model may compute a 95% confidence interval based on derived decay constants corresponding to all TOF data points within the obtained TOF curve and assess whether the computed confidence internal is below a predetermined present confidence model threshold value.

In some embodiments, a confidence interval of the present confidence model is computed by: (a) performing a non-linear regression fit of a TOF curve using some or all of the acquired TOF data points of the TOF curve; and (b) calculating the confidence interval of a retrieved computed decay constant based on the performed non-linear regression fitting. In some embodiments, all of the computed TOF data points are used to calculate the present confidence model. Said another way, all of the TOF data points computed up to the point in time when the confidence interval is being computed are used in the non-linear regression fitting of the computed TOF curve; and the confidence interval of the decay constant is calculated from the fit. In some embodiments, non-linear fitting and confidence interval calculations may be determined using the procedures described at: https://www.astro.rug.nl/software/kapteyn/kmpfittutorial.html.

In other embodiments, the "nlpredci.m" algorithm ("Non-linear regression prediction confidence intervals") in matlab is trained using the covariance matrix and mean square error calculation.

In some embodiments, the present confidence model is continuously computed after each new TOF data is derived, e.g., after each new TOF data point, TOF curve, and/or decay constant is derived. When new TOF data is derived, the fitting and statistical analysis noted above is repeated.

As noted above, the computed confidence interval is then compared to a present confidence model threshold value to determine if the condition is satisfied. In some embodiments, the present confidence model threshold value ranges from between about 0.1 hours to about 2 hours. In some embodiments, the present confidence model threshold value ranges from between about 0.1 hours to about 1.8 hours. In some embodiments, the present confidence model threshold value ranges from between about 0.1 hours to about 1.6 hours. In some embodiments, the present confidence model threshold value ranges from between about 0.2 hours to about 1.4 hours. In other embodiments, the present confidence model threshold value ranges from between about 0.3 hours to about 1.3 hours. In other embodiments, the present confidence model threshold value ranges from between about 0.4 hours to about 1.1 hours. In other embodiments, the present confidence model threshold value ranges from between about 0.5 hours to about 0.9 hours. In other embodiments, the present confidence model threshold value ranges from between about 0.6 hours to about 0.8 hours. In yet other embodiments, the present confidence model threshold value is about 0.7 hours.

A non-linear regression is a regression in which the dependent or criterion variables are modeled as a non-linear function of model parameters and one or more independent variables. In some embodiments, the non-linear regression analysis models the trend as a non-linear function, which may be, as non-limiting examples, an exponential function, a logarithmic function, a trigonometric function, a power series function, or a combination of one or more of these functions. The specific parameters of the non-linear function may be determined by "fitting" the function to plot, such as by applying a curve fitting technique (a least squares technique, as a non-limiting example) to minimize the residuals between the plot and the non-linear function. In some embodiments, the non-linear regression is selected from an Asymptotic Regression/Growth Model, a Logistic Population Growth Module, or an Asymptotic Regression/Decay Model.

Future Confidence Model

The future confidence model calculates the confidence in the signal across the entire experiment, including signal retrieved in the past, in the present, and in the future. In this regard, the future confidence model analyzes how consistent received TOF data points and/or a TOF fit are with the overall diffusion profile of the TOF signal. The future confidence model is unique from the past confidence model and the present confidence model because it takes into account the amplitude of the diffusion as well as the future predictive power. The past and present confidence models are both adapted to look at the temporal profile of the TOF curve as defined by the decay constant. The decay constant (i.e., rate of diffusion) is independent of the amplitude or total amount of fluid exchange. The future model looks at how confident the model is in predicting new TOF data points, but in terms of diffusion rate and magnitude of the diffusion.

Because it is believed that the confidence of already collected data tends to be high, the future confidence model is believed to be difficult to meet at the beginning of the experiment and tends to improve as the experiment proceeds in time, i.e., as diffusion continues in time. It thus provides a quality check against determining if a TOF data point is valid too early in the experiment. For instance, it is believed that the future confidence model could be used to stop the system from prematurely calling a received TOF data point as valid in the event the wrong decay rate was continuously resolved. As a result, it is believed that the future confidence model also improves the quality of the system for abnormally large samples that might have significantly more fluid exchange than more standard samples.

In some embodiments, the input to the future confidence model is a TOF curve retrieved from the signal processing module 202 or a memory 201 or a storage subsystem 240 in communication therewith. In some embodiments, the future confidence model computes a confidence interval based on a retrieved TOF curve and assesses whether an average of a computed confidence interval is below a predetermined threshold value. For instance, in some embodiments the confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve. In some embodiments, the future confidence model may compute an average of a 95% confidence interval of the TOF curve across all times for up to a predetermined amount of time, e.g., 4 hours, 5, hours, 6, hours, 7, hours, 8 hours, 9 hours, 10 hours, 11 hours, 12 hours, etc. In some embodiments, non-linear regression fitting (described above) may be utilized to derive the confidence intervals based on the retrieved TOF curves.

In some embodiments, the predetermined future confidence model threshold value is 0.7 ns. In some embodiments, the threshold value is 0.6 ns. In other embodiments, the predetermined future confidence model threshold value is 0.55 ns. In other embodiments, the predetermined future confidence model threshold value is 0.5 ns. In other embodiments, the threshold value is 0.45 ns. In other embodiments, the predetermined future confidence model threshold value is 0.4 ns. In other embodiments, the predetermined future confidence model threshold value is 0.35 ns. In other embodiments, the predetermined future confidence model threshold value is 0.3 ns. In other embodiments, the predetermined future confidence model threshold value is 0.25 ns. In other embodiments, the predetermined future confidence model threshold value is 0.2 ns. In other embodiments, the predetermined future confidence model threshold value is 0.15 ns. In other embodiments, the predetermined future confidence model threshold value is 0.1 ns.

Prediction Module

In some embodiments, the system 200 further includes a prediction module 204 which is adapted to predict an estimated time in which a fluid is optimally diffused through a biological specimen or an estimate time to fixation based on data received from the signal modeling module 203. Following the computation of at least two confidence models (step 403) and the determination that the computed at least two confidence models each independently and/or simultaneously meet predetermined threshold criteria (step 404), an estimated time in which a fluid is optimally diffused through a biological specimen or an estimate time to fixation completion is then calculated (step 405) using the prediction module 204. In some embodiments, the predication module 204 utilizes TOF data at a point in time in which the at least two of the confidence models were independently and/or simultaneously satisfied. For instance, if the at least two confidence models were independently satisfied at a time of 2.5 hours, then the prediction module 204 would utilize TOF data (e.g., TOF data points, TOF curves, and/or decay constants) collected at the time of 2.5 hours as this would be the time that the TOF data would be considered valid. Said another way, and in the context of the fixation of a biological specimen, once at least two of the confidence models independently and/or simultaneously meet predetermined threshold criteria, the system 200 determines at that moment in time that the TOF signal from the biological specimen is truly representative of the actual rate of diffusion and predicts at what time the tissue will be properly fixed.

In some embodiments, the estimation of a time in which a fluid is optimally diffused into a biological specimen or the estimation of a fixation time to completion is calculated using the TOF curves described herein. In some embodiments, the TOF curves are measured at a single location within the biological specimen (see Equation (11). In other embodiments, the TOF curves are measured at multiple locations with the biological specimen (a spatially-averaged TOF curve) (see Equation (12).

In embodiments where a TOF curve is measured at a single location, a time in which a fluid is optimally diffused into a biological specimen or a time to fixation completion is estimated according to Equation (11)):

$$t_{done}(\tilde{m}) = -\tau \ln(|\tilde{m}_{thres} \cdot \tau|) \tag{11}$$

where $t_{done}$ is the estimated time to diffusion or fixation completion, and the |...| symbol indicates the absolute value. In some embodiments, $T_{done}$ represents the predicted time in hours that the tissue will be sufficiently diffused with a fixative.

In embodiments where a spatially-averaged TOF curve is used, the time in which a fluid is optimally diffused into a biological specimen or the time to fixation completion may be calculated according to the Equation (12):

$$t_{done}(\tilde{m}) = -\tau_{avg} \ln(|\tilde{m}_{thres} \cdot \tau_{avg}|) \quad (12)$$

wherein $t_{done}$ is the time to diffusion fixation completion (and represents the time in hours that it is predicted that the tissue will be sufficiently diffused), $\tau_{avg}$ is the spatially averaged decay constant of the tissue; and m is the normalized threshold slope of the TOF curve ("threshold" means when the slope decreases to the "threshold" value the diffusion has slowed down enough that the tissue is properly diffused enough so that our model predicts it will stain properly). In some embodiments the $m_{thres}$ is 0.074.

In some embodiments, and in the context of the fixation of a biological specimen, after the predicted time to fixation is determined, the biological specimen is left immersed within the fixative until the predicted fixation time is reached, assuming, of course, that the predicted time to fixation is in the future. On the other hand, if the predicted time to fixation is in the present or was in the past, then the biological specimen is removed from the fixative solution. The biological specimen, once optimally fixed, may be used in further downstream processes.

Labeling of One or More Biomarkers within a Biological Specimen

Once the biological specimen has been adequately fixed, the biological specimen may be utilized in one or more downstream processes, e.g., antigen retrieval, staining, etc. In some embodiments, the biological specimen may be labeled for the presence of one or more biomarkers and/or may be counterstained once fixation is complete (or estimated to be complete). For instance, the biological specimen may be stained for the presence of the Ki-67 and p16$^{INK4a}$ biomarkers. In some embodiments, the biological specimen stained for the presence of the one or more biomarkers may be imaged and subsequently analyzed using one or more automated image analysis algorithms, including machine learning algorithms and/or "artificial intelligence."

Methods of labeling one or more biomarkers within a biological specimen are known in the art. In some embodiments, detectable moieties (e.g., haptens, chromophores, fluorophores, etc.) are deposited onto or proximal to a target within a biological specimen. In some embodiments, covalent deposition of a chromophore or detectable moiety is accomplished using Tyramide Signal Amplification (TSA), which has also been referred to as catalyzed reporter deposition (CARD). U.S. Pat. No. 5,583,001, the disclosure of which is hereby incorporated by reference herein in its entirety, discloses a method for detecting and/or quantitating an analyte using an analyte-dependent enzyme activation system that relies on catalyzed reporter deposition to amplify the detectable label signal. Catalysis of an enzyme in a CARD or TSA method is enhanced by reacting a labeled phenol molecule with an enzyme. Modern methods utilizing TSA effectively increase the signals obtained from IHC and ISH assays while not producing significant background signal amplification (see, for example, U.S. application publication No. 2012/0171668 which is hereby incorporated by reference in its entirety for disclosure related to tyramide amplification reagents). Reagents for these amplification approaches are being applied to clinically important targets to provide robust diagnostic capabilities previously unattainable (VENTANA OptiView Amplification Kit, Ventana Medical Systems, Tucson AZ, Catalog No. 760-099).

TSA takes advantage of a reaction catalyzed by horseradish peroxidase (HRP) acting on tyramide. In the presence of $H_2O_2$, tyramide is converted to a highly-reactive and short-lived radical intermediate that reacts preferentially with electron-rich amino acid residues on proteins. Covalently-bound detectable moieties can then be detected by variety of chromogenic visualization techniques and/or by fluorescence microscopy. In IHC and ISH, where spatial and morphological context is highly valued, the short lifetime of the radical intermediate results in covalent binding of the tyramide to on the tissue in close proximity to the site of generation, thereby giving discrete and specific signals at the locations of proteins and nucleic acid targets.

In other embodiments, covalent deposition of a chromophore or detectable moiety is performed using quinone methide chemistry. U.S. Pat. No. 10,168,336, the disclosure of which is hereby incorporated by reference herein in its entirety, entitled "Quinone Methide Analog Signal Amplification," granted on Jan. 1, 2019, describes a technique ("QMSA") that, like TSA, may be used to increase signal amplification without significantly increasing background signals. In particular, U.S. Pat. No. 10,168,336 describes novel quinone methide analog precursors and methods of using the quinone methide analog precursors to detect one or more targets in a biological specimen. In a particular embodiment, the method of detection includes contacting the sample with a detection antibody or probe, then contacting the sample with a labeling conjugate that comprises an alkaline phosphatase (AP) enzyme and a binding moiety, where the binding moiety recognizes the antibody or probe (for example, by binding to a hapten or a species specific antibody epitope, or a combination thereof). The alkaline phosphatase enzyme of the labeling conjugate interacts with a quinone methide analog precursor comprising the detectable moiety, thereby forming a reactive quinone methide analog, which binds covalently to the biological specimen proximally to or directly on the target. The detectable label is then detected, such as visually or through imaging techniques. U.S. Pat. No. 10,168,336 is incorporated by reference herein in its entirety.

Another technique for depositing detectable moieties employs "click" chemistry to form a covalent bond between a detectable moiety and a morphological marker or a biomarker in a sample. "Click chemistry" is a chemical philosophy, independently defined by the groups of Sharpless and Meldal, that describes chemistry tailored to generate substances quickly and reliably by joining small units together. "Click chemistry" has been applied to a collection of reliable and self-directed organic reactions (Kolb, H. C.; Finn, M. G.; Sharpless, K. B. Angew. Chem. Int. Ed. 2001, 40, 2004-2021). In the context of covalently depositing detectable labels onto a biological specimen, a click chemistry technique is described in US2019/0204330, which incorporated by reference herein in its entirety. In this technique, either tyramide deposition as described above or quinone methide deposition also described above, is used to covalently anchor a first reactive group capable of participating in a click chemistry reaction to the biological specimen. A second component of the detection system having a corresponding second reactive group capable of participating in a click chemistry reaction is then reacted with the rust reactive group to covalently bind the second component to the biological specimen.

In a particular embodiment, the technique described includes contacting the biological specimen with a first detection probe specific to a first target. The first detection probe may be a primary antibody or a nucleic acid probe.

Subsequently, the sample is contacted with a first labeling conjugate, the first labeling conjugate comprising a first enzyme. In some embodiments, the first labeling conjugate is a secondary antibody specific for either the primary antibody (such as the species from which the antibody was obtained) or to a label (such as a hapten) conjugated to the nucleic acid probe. Next, the biological specimen is contacted with a first member of a pair of click conjugates. The first enzyme cleaves the first member of the pair of click conjugates having a tyramide or quinone methide precursor, thereby converting the first member into a reactive intermediate which covalently binds to the biological specimen proximally to or directly on the first target. Next, a second member of the pair of click conjugates is contacted with the biological specimen, the second member of the pair of click conjugates comprising a first reporter moiety (e.g., a chromophore) and a second reactive functional group, where the second reactive functional group of the second member of the first pair of click conjugates is capable of reacting with the first reactive functional group of the first member of the pair of click conjugates. Finally, signals from the first reporter moiety are detected.

Examples of Biomarkers

As noted herein, the fixation estimation engine is trained using training spectral data sets acquired from a plurality of differentially fixed training biological specimens. In some embodiments, the class labels of known fixation duration are verified through functional IHC testing. Identified below are non-limiting examples of biomarkers whose expression may be determined through functional IHC staining. Certain markers are characteristic of particular cells, while other markers have been identified as being associated with a particular disease or condition. Examples of known prognostic markers include enzymatic markers such as, for example, galactosyl transferase II, neuron specific enolase, proton ATPase-2, and acid phosphatase. Hormone or hormone receptor markers include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, and insulin receptor.

Lymphoid markers include alpha-1-antichymotrypsin, alpha-1-antitrypsin, B cell marker, bcl-2, bcl-6, B lymphocyte antigen 36 kD, BMI (myeloid marker), BM2 (myeloid marker), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage marker, muramidase (lysozyme), p80 anaplastic lymphoma kinase, plasma cell marker, secretory leukocyte protease inhibitor, T cell antigen receptor (JOVI 1), T cell antigen receptor (JOVI 3), terminal deoxynucleotidyl transferase, unclustered B cell marker.

Tumor markers include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumor associated mucin antigen), chromogranin A, clusterin (apolipoprotein J), epithelial membrane antigen, epithelial-related antigen, epithelial specific antigen, epidermal growth factor receptor, estrogen receptor (ER), gross cystic disease fluid protein-15, hepatocyte specific antigen, HER2, heregulin, human gastric mucin, human milk fat globule, MAGE-1, matrix metalloproteinases, melan A, melanoma marker (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma marker), Myf-4 (Rhabdomyosarcoma marker), MyoD1 (Rhabdomyosarcoma marker), myoglobin, nm23 protein, placental alkaline phosphatase, prealbumin, progesterone receptor, prostate specific antigen, prostatic acid phosphatase, prostatic inhibin peptide, PTEN, renal cell carcinoma marker, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, von Willebrand factor, CD34, CD34, Class II, CD51 Ab-1, CD63, CD69, Chk1, Chk2, claspin C-met, COX6C, CREB, Cyclin D1, Cytokeratin, Cytokeratin 8, DAPI, Desmin, DHP (1-6 Diphenyl-1,3,5-Hexatriene), E-Cadherin, EEA1, EGFR, EGFRvIII, EMA (Epithelial Membrane Antigen), ER, ERB3, ERCC1, ERK, E-Selectin, FAK, Fibronectin, FOXP3, Gamma-H2AX, GB3, GFAP, Giantin, GM130, Golgin 97, GRB2, GRP78BiP, GSK3 Beta, HER-2, Histone 3, Histone 3_K14-Ace [Anti-acetyl-Histone H3 (Lys 14)], Histone 3_K18-Ace [Histone H3-Acetyl Lys 18), Histone 3_K27-TriMe, [Histone H3 (trimethyl K27)], Histone 3_K4-diMe [Anti-dimethyl-Histone H3 (Lys 4)], Histone 3_K9-Ace [Acetyl-Histone H3 (Lys 9)], Histone 3_K9-triMe [Histone 3-trimethyl Lys 9], Histone 3_S10-Phos [Anti-Phospho Histone H3 (Ser 10), Mitosis Marker], Histone 4, Histone H2A.X-5139-Phos [Phospho Histone H2A.X (Ser139)antibody], Histone H2B, Histone H3_DiMethyl K4, Histone H4_TriMethyl K20-Chip grad, HSP70, Urokinase, VEGF R1, ICAM-1, IGF-1, IGF-1R, IGF-1 Receptor Beta, IGF-II, IGF-IIR, IKB-Alpha IKKE, IL6, IL8, Integrin alpha V beta 3, Integrin alpha V beta6, Integrin Alpha V/CD51, integrin B5, integrin B6, Integrin B8, Integrin Beta 1(CD 29), Integrin beta 3, Integrin beta 5 integrinB6, IRS-1, Jagged 1, Anti-protein kinase C Beta2, LAMP-1, Light Chain Ab-4 (Cocktail), Lambda Light Chain, kappa light chain, M6P, Mach 2, MAPKAPK-2, MEK 1, MEK 1/2 (Ps222), MEK 2, MEK1/2 (47E6), MEK1/2 Blocking Peptide, MET/HGFR, MGMT, Mitochondrial Antigen, Mitotracker Green F M, MMP-2, MMP9, E-cadherin, mTOR, ATPase, N-Cadherin, Nephrin, NFKB, NFKB p105/p50, NF-KB P65, Notch 1, Notch 2, Notch 3, OxPhos Complex IV, p130Cas, p38 MAPK, p44/42 MAPK antibody, P504S, P53, P70, P70 S6K, Pan Cadherin, Paxillin, P-Cadherin, PDI, pEGFR, Phospho AKT, Phospho CREB, phospho EGF Receptor, Phospho GSK3 Beta, Phospho H3, Phospho HSP-70, Phospho MAPKAPK-2, Phospho MEK1/2, phospho p38 MAP Kinase, Phospho p44/42 MAPK, Phospho p53, Phospho PKC, Phospho S6 Ribosomal Protein, Phospho Src, phospho-Akt, Phospho-Bad, Phospho-IKB-a, phospho-mTOR, Phospho-NF-kappaB p65, Phospho-p38, Phospho-p44/42 MAPK, Phospho-p70 S6 Kinase, Phospho-Rb, phospho-Smad2, PIM1, PIM2, PKC β, Podocalyxin, PR, PTEN, R1, Rb 4H1, R-Cadherin, ribonucleotide Reductase, RRM1, RRM11, SLC7A5, NDRG, HTF9C, HTF9C, CEACAM, p33, S6 Ribosomal Protein, Src, Survivin, Synapopodin, Syndecan 4, Talin, Tensin, Thymidylate Synthase, Tuberlin, VCAM-1, VEGF, Vimentin, Agglutinin, YES, ZAP-70 and ZEB.

Cell cycle associated markers include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mci-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, topoisomerase II beta.

Neural tissue and tumor markers include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma marker, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, ubiquitin.

Cluster differentiation markers include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD 114, CD 115, CD 116, CD 117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other cellular markers include centromere protein-F (CENP-F), giantin, involucrin, lamin A&C [XB 10], LAP-70, mucin, nuclear pore complex proteins, p180 lamellar body protein, ran, r, cathepsin D, Ps2 protein, Her2-neu, P53, S100, epithelial marker antigen (EMA), TdT, MB2, MB3, PCNA, and Ki67.

Yet other suitable markers for detection include those set forth in the following Table 2:

TABLE 2

| MARKER | DESCRIPTION | LOCATION |
| --- | --- | --- |
| AHNAK | AHNAK nucleoprotein | Intracellular |
| AHNAK2 | AHNAK nucleoprotein 2 | Intracellular |
| AIG1 | androgen induced 1 | Intracellular, Membrane |
| AKR1A1 | aldo-keto reductase family 1 member A1 | Intracellular |
| AKR1B1 | aldo-keto reductase family 1 member B | Intracellular |
| ANLN | anillin actin binding protein | Intracellular |
| ANXA1 | annexin A1 | Intracellular, Secreted |
| ARHGAP4 | Rho GTPase activating protein 4 | Intracellular |
| ARL8A | ADP ribosylation factor like GTPase 8A | Intracellular |
| ARMC10 | armadillo repeat containing 10 | Intracellular, Membrane |
| ARRB2 | arrestin beta 2 | Intracellular |
| ASB6 | ankyrin repeat and SOCS box containing 6 | Intracellular |
| ATG4A | autophagy related 4A cysteine peptidase | Intracellular |
| ATP5F1B | ATP synthase F1 subunit beta | Intracellular |
| ATPSCKMT | ATP synthase c subunit lysine N-methyltransferase | Intracellular, Membrane |
| BAIAP2 | BAR/IMD domain containing adaptor protein 2 | Intracellular |
| BCAR3 | BCAR3 adaptor protein, NSP family member | Intracellular |
| BOC | BOC cell adhesion associated; oncogene regulated | Intracellular, Membrane |
| BRMS1L | BRMS1 like transcriptional repressor | Intracellular |
| C8orf88 | chromosome 8 open reading frame 88 | Intracellular |
| CA12 | carbonic anhydrase 12 | Membrane |
| CAMK2N1 | calcium/calmodulin dependent protein kinase II inhibitor 1 | Intracellular |
| CAST | calpastatin | Intracellular |
| CCNA2 | cyclin A2 | Intracellular |
| CCNB2 | cyclin B2 | Intracellular |
| CCPG1 | cell cycle progression 1 | Intracellular, Membrane |
| CD109 | CD109 molecule | Membrane |
| CDCA5 | cell division cycle associated 5 | Intracellular |
| CDK1 | cyclin dependent kinase 1 | Intracellular |
| CDK6 | cyclin dependent kinase 6 | Intracellular |
| CEP55 | centrosomal protein 55 | Intracellular |
| CEP70 | centrosomal protein 70 | Intracellular |
| CGB5 | chorionic gonadotropin subunit beta 5 | Secreted |
| CHEK1 | checkpoint kinase 1 | Intracellular |
| CLK3 | CDC like kinase 3 | Intracellular |
| CMIP | c-Maf inducing protein | Intracellular |
| CNPY3 | canopy FGF signaling regulator 3 | Intracellular |
| COL22A1 | collagen type XXII alpha 1 chain | Intracellular, Secreted |
| COLGALT1 | collagen beta(1-O)galactosyltransferase 1 | Intracellular |
| COMMD2 | COMM domain containing 2 | Intracellular |

TABLE 2-continued

| MARKER | DESCRIPTION | LOCATION |
| --- | --- | --- |
| COPS3 | COP9 signalosome subunit 3 | Intracellular |
| CRACR2B | calcium release activated channel regulator 2B | Intracellular |
| CTTN | cortactin | Intracellular |
| CYTL1 | cytokine like 1 | Secreted |
| DAPK1 | death associated protein kinase 1 | Membrane |
| DCTPP1 | dCTP pyrophosphatase 1 | Intracellular |
| DDX49 | DEAD-box helicase 49 | Intracellular |
| DIPK1B | divergent protein kinase domain 1B | Intracellular, Membrane |
| DKK1 | dickkopf WNT signaling pathway inhibitor 1 | Secreted |
| DNAJC9 | DnaJ heat shock protein family (Hsp40) member C9 | Intracellular |
| DPP7 | dipeptidyl peptidase 7 | Intracellular, Secreted |
| DSC3 | desmocollin 3 | Membrane |
| DTD2 | D-aminoacyl-tRNA deacylase 2 | Intracellular |
| DUSP1 | dual specificity phosphatase 1 | Intracellular |
| DVL3 | dishevelled segment polarity protein 3 | Intracellular |
| EAF2 | ELL associated factor 2 | Intracellular |
| EFNB2 | ephrin B2 | Membrane |
| EGFL7 | EGF like domain multiple 7 | Secreted |
| EHBP1 | EH domain binding protein 1 | Intracellular |
| EMP1 | epithelial membrane protein 1 | Intracellular, Membrane |
| EPS8 | epidermal growth factor receptor pathway substrate 8 | Intracellular |
| EXOC3L4 | exocyst complex component 3 like 4 | Intracellular |
| F8A1 | coagulation factor VIII associated 1 | Intracellular |
| FAM83A | family with sequence similarity 83 member A | Intracellular |
| FBXO45 | F-box protein 45 | Intracellular |
| FKBP10 | FKBP prolyl isomerase 10 | Intracellular |
| FKBP9 | FKBP prolyl isomerase 9 | Intracellular |
| FN1 | fibronectin 1 | Intracellular, Secreted |
| FOXM1 | forkhead box M1 | Intracellular |
| FSTL3 | follistatin like 3 | Intracellular, Secreted |
| FZD6 | frizzled class receptor 6 | Membrane |
| GALNT2 | polypeptide N-acetylgalactosaminyltransferase 2 | Intracellular |
| GAS6 | growth arrest specific 6 | Secreted |
| GJA1 | gap junction protein alpha 1 | Membrane |
| GPR176 | G protein-coupled receptor 176 | Membrane |
| GPRIN1 | G protein regulated inducer of neurite outgrowth 1 | Intracellular |
| HK1 | hexokinase 1 | Intracellular |
| HOOK2 | hook microtubule tethering protein 2 | Intracellular |
| HSH2D | hematopoietic SH2 domain containing | Intracellular |
| HSPA1A | heat shock protein family A (Hsp70) member 1A | Intracellular |
| HSPB6 | heat shock protein family B (small) member 6 | Intracellular |
| HTRA1 | HtrA serine peptidase 1 | Intracellular, Secreted |
| IER5L | immediate early response 5 like | Intracellular |
| INAFM1 | InaF motif containing 1 | Intracellular |
| INSIG2 | insulin induced gene 2 | Membrane |
| ISCU | iron-sulfur cluster assembly enzyme | Intracellular |
| ITGAV | integrin subunit alpha V | Intracellular, Membrane |
| ITGB1 | integrin subunit beta 1 | Intracellular, Membrane |
| JAG1 | jagged canonical Notch ligand 1 | Intracellular, Membrane |
| KARS1 | lysyl-tRNA synthetase 1 | Intracellular |
| KIF11 | kinesin family member 11 | Intracellular |
| KIF20A | kinesin family member 20A | Intracellular |
| KIF22 | kinesin family member 22 | Intracellular |
| KLK5 | kallikrein related peptidase 5 | Secreted |
| KPNA4 | karyopherin subunit alpha 4 | Intracellular |
| L1CAM | L1 cell adhesion molecule | Intracellular, Membrane |
| LAMA3 | laminin subunit alpha 3 | Intracellular, Secreted |
| LAMC2 | laminin subunit gamma 2 | Secreted |
| LDHA | lactate dehydrogenase A | Intracellular |
| LIMA1 | LIM domain and actin binding 1 | Intracellular |
| LIMCH1 | LIM and calponin homology domains 1 | Intracellular |
| LMNB2 | lamin B2 | Intracellular |
| LOXL2 | lysyl oxidase like 2 | Intracellular, Secreted |
| LRCH4 | leucine rich repeats and calponin homology domain containing 4 | Intracellular, Membrane |
| LRP11 | LDL receptor related protein 11 | Intracellular, Membrane |
| LRRC59 | leucine rich repeat containing 59 | Intracellular, Membrane |
| LY6D | lymphocyte antigen 6 family member D | Membrane |
| MAL2 | mal, T cell differentiation protein 2 | Membrane |
| MANF | mesencephalic astrocyte derived neurotrophic factor | Secreted |
| MATN3 | matrilin 3 | Secreted |
| MBD1 | methyl-CpG binding domain protein 1 | Intracellular |
| MCM5 | minichromosome maintenance complex component 5 | Intracellular |
| MEI1 | meiotic double-stranded break formation protein 1 | Intracellular |
| MELK | maternal embryonic leucine zipper kinase | Intracellular, Membrane |
| MET | MET proto-oncogene, receptor tyrosine kinase | Intracellular, Membrane, Secreted |
| MRPL3 | mitochondrial ribosomal protein L3 | Intracellular |

TABLE 2-continued

| MARKER | DESCRIPTION | LOCATION |
| --- | --- | --- |
| MTF2 | metal response element binding transcription factor 2 | Intracellular |
| MYEOV | myeloma overexpressed | Membrane |
| MYO1D | myosin ID | Intracellular |
| MYO1E | myosin IE | Intracellular |
| NCAPH2 | non-SMC condensin II complex subunit H2 | Intracellular |
| NDFIP1 | Nedd4 family interacting protein 1 | Membrane |
| NMRAL1 | NmrA like redox sensor 1 | Intracellular |
| NPDC1 | neural proliferation, differentiation and control 1 | Intracellular, Membrane |
| NRP1 | neuropilin 1 | Intracellular, Membrane, Secreted |
| OPN1SW | opsin 1, short wave sensitive | Membrane |
| PAQR6 | progestin and adipoQ receptor family member 6 | Intracellular, Membrane |
| PCMT1 | protein-L-isoaspartate (D-aspartate) O-methyltransferase | Intracellular, Membrane |
| PCTP | phosphatidylcholine transfer protein | Intracellular |
| PDSS2 | decaprenyl diphosphate synthase subunit 2 | Intracellular |
| PGK1 | phosphoglycerate kinase 1 | Intracellular |
| PGK1 | phosphoglycerate kinase 1 | Intracellular |
| PLA1A | phospholipase A1 member A | Intracellular, Secreted |
| PLCD3 | phospholipase C delta 3 | Intracellular |
| PLD1 | phospholipase D1 | Intracellular |
| PLIN3 | perilipin 3 | Intracellular |
| PLK1 | polo like kinase 1 | Intracellular |
| POFUT2 | protein O-fucosyltransferase 2 | Intracellular |
| PPP1R3B | protein phosphatase 1 regulatory subunit 3B | Intracellular |
| PRR11 | proline rich 11 | Intracellular |
| PRSS36 | serine protease 36 | Secreted |
| PTGES3 | prostaglandin E synthase 3 | Intracellular |
| RAB5B | RAB5B, member RAS oncogene family | Intracellular |
| RAN | RAN, member RAS oncogene family | Intracellular |
| RBM38 | RNA binding motif protein 38 | Intracellular |
| RBM8A | RNA binding motif protein 8A | Intracellular |
| RCN1 | reticulocalbin 1 | Intracellular |
| RHBDD2 | rhomboid domain containing 2 | Membrane |
| RIBC2 | RIB43A domain with coiled-coils 2 | Intracellular |
| RIPK2 | receptor interacting serine/threonine kinase 2 | Intracellular |
| RNF144A | ring finger protein 144A | Intracellular, Membrane |
| RNF152 | ring finger protein 152 | Intracellular, Membrane |
| RNF8 | ring finger protein 8 | Intracellular |
| RPAIN | RPA interacting protein | Intracellular |
| RTL8B | retrotransposon Gag like 8B | Intracellular |
| RTN4IP1 | reticulon 4 interacting protein 1 | Intracellular |
| SEC14L2 | SEC14 like lipid binding 2 | Intracellular |
| SEC61G | SEC61 translocon subunit gamma | Membrane |
| SERPINE1 | serpin family E member 1 | Secreted |
| SH3GLB2 | SH3 domain containing GRB2 like, endophilin B2 | Intracellular |
| SHTN1 | shootin 1 | Intracellular |
| SLC1A6 | solute carrier family 1 member 6 | Intracellular, Membrane |
| SLC25A28 | solute carrier family 25 member 28 | Intracellular |
| SLC2A3 | solute carrier family 2 member 3 | Membrane |
| SLC2A8 | solute carrier family 2 member 8 | Membrane |
| SP6 | Sp6 transcription factor | Intracellular |
| SPAG4 | sperm associated antigen 4 | Intracellular, Membrane |
| SPC24 | SPC24 component of NDC80 kinetochore complex | Intracellular |
| SPDYC | speedy/RINGO cell cycle regulator family member C | Intracellular |
| SPRED1 | sprouty related EVH1 domain containing 1 | Intracellular, Membrane |
| SSBP3 | single stranded DNA binding protein 3 | Intracellular |
| STC2 | stanniocalcin 2 | Intracellular, Secreted |
| STK24 | serine/threonine kinase 24 | Intracellular |
| TAGLN2 | transgelin 2 | Intracellular |
| TCEAL8 | transcription elongation factor A like 8 | Intracellular |
| TEX30 | testis expressed 30 | Intracellular |
| TIMM17A | translocase of inner mitochondrial membrane 17A | Membrane |
| TM4SF1 | transmembrane 4 L six family member 1 | Membrane |
| TMCO1 | transmembrane and coiled-coil domains 1 | Membrane |
| TMED2 | transmembrane p24 trafficking protein 2 | Intracellular, Membrane |
| TNFRSF13C | TNF receptor superfamily member 13C | Membrane |
| TNNT1 | troponin T1, slow skeletal type | Intracellular |
| TOP2A | DNA topoisomerase II alpha | Intracellular |
| TPD52 | tumor protein D52 | Intracellular |
| TPX2 | TPX2 microtubule nucleation factor | Intracellular |
| TRIP13 | thyroid hormone receptor interactor 13 | Intracellular |
| TRMT2B | tRNA methyltransferase 2 homolog B | Intracellular |
| USP53 | ubiquitin specific peptidase 53 | Intracellular |
| WNT7A | Wnt family member 7A | Intracellular, Secreted |
| XRCC4 | X-ray repair cross complementing 4 | Intracellular |
| ZDHHC4 | zinc finger DHHC-type palmitoyltransferase 4 | Membrane |
| ZER1 | zyg-11 related cell cycle regulator | Intracellular |
| ZFP91 | ZFP91 zinc finger protein, atypical E3 ubiquitin ligase | Intracellular |

TABLE 2-continued

| MARKER | DESCRIPTION | LOCATION |
|---|---|---|
| ZNF330 | zinc finger protein 330 | Intracellular |
| ZNF488 | zinc finger protein 488 | Intracellular |
| ZNF587B | zinc finger protein 587B | Intracellular |
| ZNF654 | zinc finger protein 654 | Intracellular |
| ZNF875 | zinc finger protein 875 | Intracellular |

Other Downstream Processing Steps and System Components

The system 200 of the present disclosure may be tied to a biological specimen processing apparatus that can perform one or more preparation processes on the tissue specimen, such as after an estimated time to fixation is determined and/or after the biological specimen has been fixed in accordance with the present disclosure. The preparation process can include, without limitation, deparaffinizing a specimen, conditioning a specimen (e.g., cell conditioning), staining a specimen, performing antigen retrieval, performing immunohistochemistry staining (including labeling) or other reactions, and/or performing in situ hybridization (e.g., SISH, FISH, etc.) staining (including labeling) or other reactions, as well as other processes for preparing specimens for microscopy, microanalyses, mass spectrometric methods, or other analytical methods.

The processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized using appropriate deparaffinizing fluid(s). After the paraffin is removed, any number of substances can be successively applied to the specimen. The substances can be for pretreatment (e.g., to reverse protein-crosslinking, expose cells acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated cells acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes. As used herein, the term "fluid" refers to any liquid or liquid composition, including water, solvents, buffers, solutions (e.g., polar solvents, non-polar solvents), and/or mixtures. The fluid may be aqueous or non-aqueous. Non-limiting examples of fluids include washing solutions, rinsing solutions, acidic solutions, alkaline solutions, transfer solutions, and hydrocarbons (e.g., alkanes, isoalkanes and aromatic compounds such as xylene). In some embodiments, washing solutions include a surfactant to facilitate spreading of the washing liquids over the specimen-bearing surfaces of the slides. In some embodiments, acid solutions include deionized water, an acid (e.g., acetic acid), and a solvent. In some embodiments, alkaline solutions include deionized water, a base, and a solvent. In some embodiments, transfer solutions include one or more glycol ethers, such as one or more propylene-based glycol ethers (e.g., propylene glycol ethers, di(propylene glycol) ethers, and tri(propylene glycol) ethers, ethylene-based glycol ethers (e.g., ethylene glycol ethers, di(ethylene glycol) ethers, and tri(ethylene glycol) ethers), and functional analogs thereof. Non-liming examples of buffers include citric acid, potassium dihydrogen phosphate, boric acid, diethyl barbituric acid, piperazine-N,N'-bis(2-ethanesulfonic acid), dimethylarsinic acid, 2-(N-morpholino)ethanesulfonic acid, tris(hydroxymethyl)methylamine (TRIS), 2-(N-morpholino)ethanesulfonic acid (TAPS), N,N-bis(2-hydroxyethyl)glycine(Bicine), N-tris(hydroxymethyl)methylglycine (Tricine), 4-2-hydroxyethyl-1-piperazineethanesulfonic acid (HEPES), 2-{[tris(hydroxymethyl)methyl]amino}ethanesulfonic acid (TES), and combinations thereof. In some embodiments, the unmasking agent is water. In other embodiments, the buffer may be comprised of tris(hydroxymethyl)methylamine (TRIS), 2-(N-morpholino)ethanesulfonic acid (TAPS), N,N-bis(2-hydroxyethyl)glycine(Bicine),N-tris(hydroxymethyl)methylglycine (Tricine), 4-2-hydroxyethyl-1-piperazineethanesulfonic acid (HEPES), 2-{[tris(hydroxymethyl)methyl]amino}ethanesulfonic acid (TES), or a combination thereof. Additional wash solutions, transfer solutions, acid solutions, and alkaline solutions are described in United States Patent Application Publication No. 2016/0282374, the disclosure of which is hereby incorporated by reference herein in its entirety.

Staining may be performed with a histochemical staining module or separate platform, such as an automated IHC/ISH slide stainer. Automated IHC/ISH slide stainers typically include at least: reservoirs of the various reagents used in the staining protocols, a reagent dispense unit in fluid communication with the reservoirs for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, Overview of Automated Immunohistochemistry, Arch Pathol Lab Med., Vol. 138, pp. 1578-1582 (2014), incorporated herein by reference in its entirety, describes several specific examples of automated IHC/ISH slide stainers and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. As used herein, the term "reagent" refers to solutions or suspensions including one or more agents capable of covalently or non-covalently reacting with, coupling with, interacting with, or hybridizing to another entity. Non-limiting examples of such agents include specific-binding entities, antibodies (primary antibodies, secondary antibodies, or antibody conjugates), nucleic acid probes, oligonucleotide sequences, detection probes, chemical moieties bearing a reactive functional group or a protected functional group, enzymes, solutions or suspensions of dye or stain molecules.

Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform.

Where a morphologically-stained sample is also desired, an automated H&E staining platform may be used. Automated systems for performing H&E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH.

After the specimens are stained, the stained samples can be manually analyzed on a microscope, and/or digital images of the stained samples can be acquired for archiving and/or digital analysis. Digital images can be captured via a scanning platform such as a slide scanner that can scan the stained slides at 20×, 40×, or other magnifications to produce high resolution whole-slide digital images. At a basic level, the typical slide scanner includes at least: (1) a microscope with lens objectives, (2) a light source (such as halogen, light emitting diode, white light, and/or multispectral light sources, depending on the dye), (3) robotics to move glass slides around or to move the optics around the slide or both, (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., Whole slide imaging in pathology: advantages, limitations, and emerging perspectives, Pathology and Laboratory Medicine Int'l, Vol. 7, p. 23-33 (June 2015), the content of which is incorporated by reference in its entirety. Examples of commercially available slide scanners include: 3DHistech PANORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety.

In some embodiments, any imaging may be accomplished using any of the systems disclosed in U.S. Pat. Nos. 10,317,666 and 10,313,606, the disclosures of which are hereby incorporated by reference herein in their entireties. The imaging apparatus may be a brightfield imager such as the iScan Coreo™ brightfield scanner or the DP200 scanner sold by Ventana Medical Systems, Inc.

In some cases, the images may be analyzed on an image analysis system. Image analysis system may include one or more computing devices such as desktop computers, laptop computers, tablets, smartphones, servers, application-specific computing devices, or any other type(s) of electronic device(s) capable of performing the techniques and operations described herein. In some embodiments, image analysis system may be implemented as a single device. In other embodiments, image analysis system may be implemented as a combination of two or more devices together achieving the various functionalities discussed herein. For example, image analysis system may include one or more server computers and a one or more client computers communicatively coupled to each other via one or more local-area networks and/or wide-area networks such as the Internet. The image analysis system typically includes at least a memory, a processor, and a display. Memory may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. It is appreciated that memory can be included in a single device and can also be distributed across two or more devices. Processor may include one or more processors of any type, such as central processing units (CPUs), graphics processing units (GPUs), special-purpose signal or image processors, field-programmable gate arrays (FPGAs), tensor processing units (TPUs), and so forth. It is appreciated that processor can be included in a single device and can also be distributed across two or more devices. Display may be implemented using any suitable technology, such as LCD, LED, OLED, TFT, Plasma, etc. In some implementations, display may be a touch-sensitive display (a touchscreen). Image analysis system also typically includes a software system stored on the memory comprising a set of instructions implementable on the processor, the instructions comprising various image analysis tasks, such as object identification, stain intensity quantification, and the like. Exemplary commercially-available software packages useful in implementing modules as disclosed herein include VENTANA VIRTUOSO; Definiens TISSUE STUDIO, DEVELOPER XD, and IMAGE MINER; and Visopharm BIOTOPIX, ONCOTOPIX, and STEREOTOPIX software packages.

After the specimens are processed, a user can transport specimen-bearing slides to the imaging apparatus. In some embodiments, the imaging apparatus is a brightfield imager slide scanner. One brightfield imager is the iScan Coreo brightfield scanner sold by Ventana Medical Systems, Inc. In automated embodiments, the imaging apparatus is a digital pathology device as disclosed in International Patent Application No.: PCT/US2010/002772 (Patent Publication No.:

WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entities.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, for example, one or more modules of computer program instructions, encoded on computer storage medium for execution by, or to control the operation of, data processing apparatus. Any of the modules described herein may include logic that is executed by the processor(s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks). For example, the network 20 of FIG. 2 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Other Methods of Computing TOF for a Sample Immersed in One or More Fixatives

In some embodiments, the rate of diffusion may be monitored by a system of acoustic probes based on the different acoustic properties of formalin-soaked tissue samples. Such a system for diffusion monitoring and experimental TOF measurement is described in further detail U.S. Patent Publication Nos. 2013/0224791, 2017/0284969, 2017/0336363, 2017/0284920, and 2017/0284859 the disclosures of which are each incorporated by reference herein in their entireties.

Further examples of suitable systems and methods for TOF monitoring are described in PCT Publication No. WO2016/097163 and US Patent Publication No. 2017/0284859, the contents of which are also incorporated by reference herein to the extent they are not inconsistent with the present disclosure. The referenced applications describe solid tissue samples being contacted with a liquid fixative that travels through the tissue samples and diffuses throughout substantially the entire thickness of the tissue samples and being analyzed based on acoustic characteristics that are continuously or periodically monitored to evaluate the state and condition of the tissue sample throughout processing. For example, a fixative such as formalin having a bulk modulus greater than interstitial fluid can significantly alter the TOF as it displaces the interstitial fluid. The acoustic properties of tissue samples may change as liquid reagent (e.g., a liquid fixative) travels through the sample. The sample's acoustic properties can change during, for example, a pre-soak process (e.g., diffusion of cold fixative), a fixation process, a staining process, or the like. In the fixation process (e.g., a cross-linking process), the speed of transmission of acoustic energy can change as the tissue sample becomes more heavily cross-linked. Real-time monitoring can be used to accurately track movement of the fixative through the sample.

EXAMPLES

Example 1—Example Time Courses for Each of the Past, Present, and Future Confidence Models An example time course showing multiple time points of TOF data collection are set forth in FIG. 5. In the series of plots, initially the predictive power of the TOF curve is very poor as indicated by the large dotted line that significantly deviates from the best-fit black line (see the top plot). All three parameters vary considerably as more TOF data is collected (a-d). After about 2.83 hours of active diffusion the model determine the tissue's TOF curve is deemed valid and predicts that after 4.41 hours of diffusion the tissue sample will stain properly. The models continue to collect more data and shifts the estimate slightly longer to 4.7 hours where the sample would be considered well fixed.

Figures 6A, 6B:
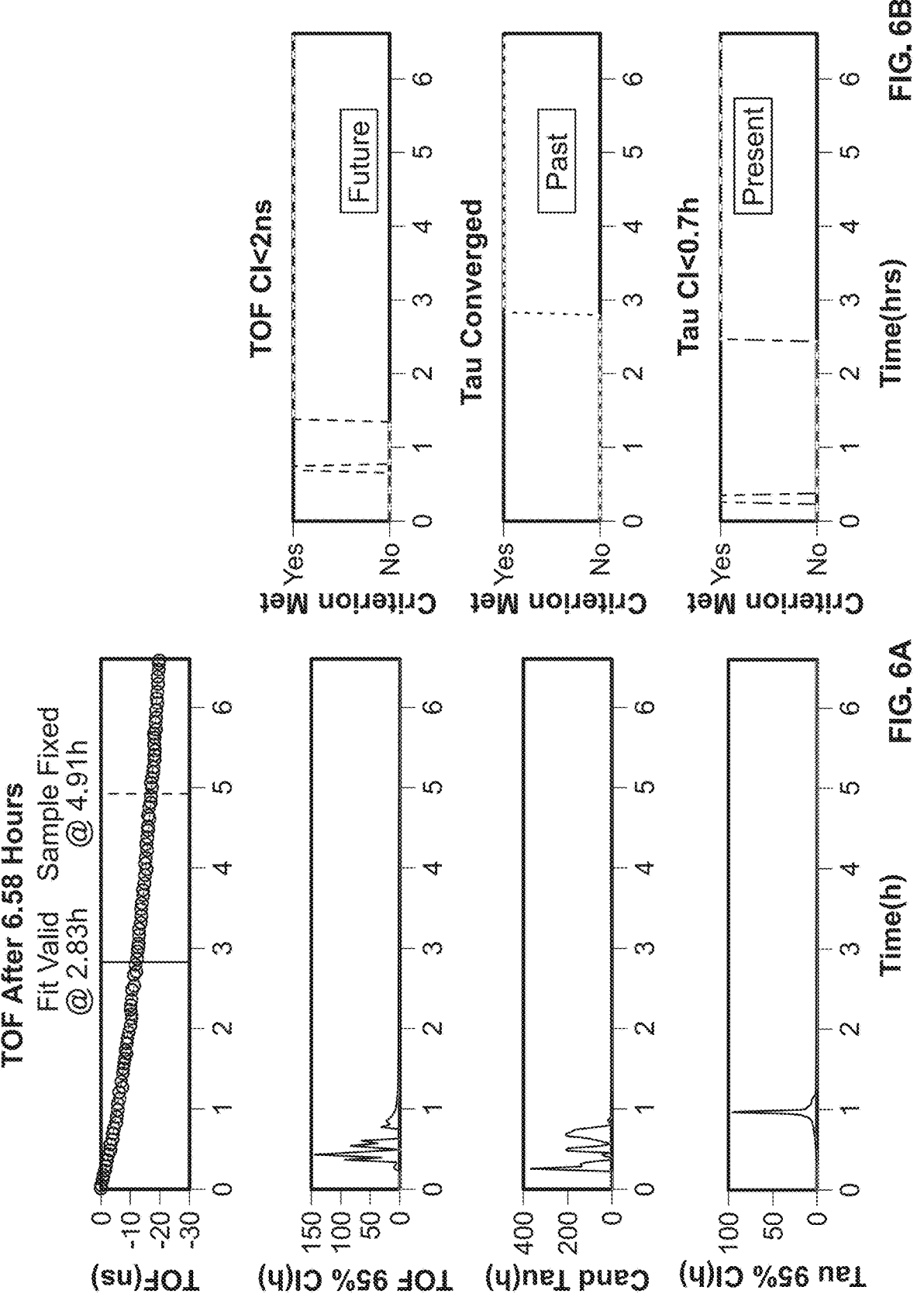
FIGS. 6A-6B illustrate an example of determining if a TOF curve is valid for the same tonsil tissue specimen as depicted in FIG. 5. a) Top plot: TOF curve with black circles representing single TOF data points, the best-fit curve is depicted with a solid black line; the 95% confident interval is depicted with the dashed/dotted lines. Top-middle plot: The width of the 95% confident interval for the TOF curve. Bottom-middle plot: Candidate decay constant calculated using the most recent data point acquired. Bottom plot: 95% confidence interval of the decay constant. b) Graph of each individual confidence model for all time points in the experiment with a high value indicating criterion is met and a low value indicating criterion is not met. In this specific example, all three criteria must be simultaneously satisfied for the TOF signal to be deemed representative of the tissue's actual diffusion profile. (Top graph is future confidence model, middle graph is past confidence model, bottom graph is present confidence model).

A more detailed version of each of the past, present, and future confidence models are presented in FIG. 6, where the criterion for all three confidence models is plotted against time. From the graphs it can observed that initially the future and present confidence models are satisfied but then as more data is collected the criterion is reversed. Thus, the past criterion being unmet in the beginning of the experiment was crucially important to not call the TOF signal valid when it actually was not.

Figures 7A, 7B:
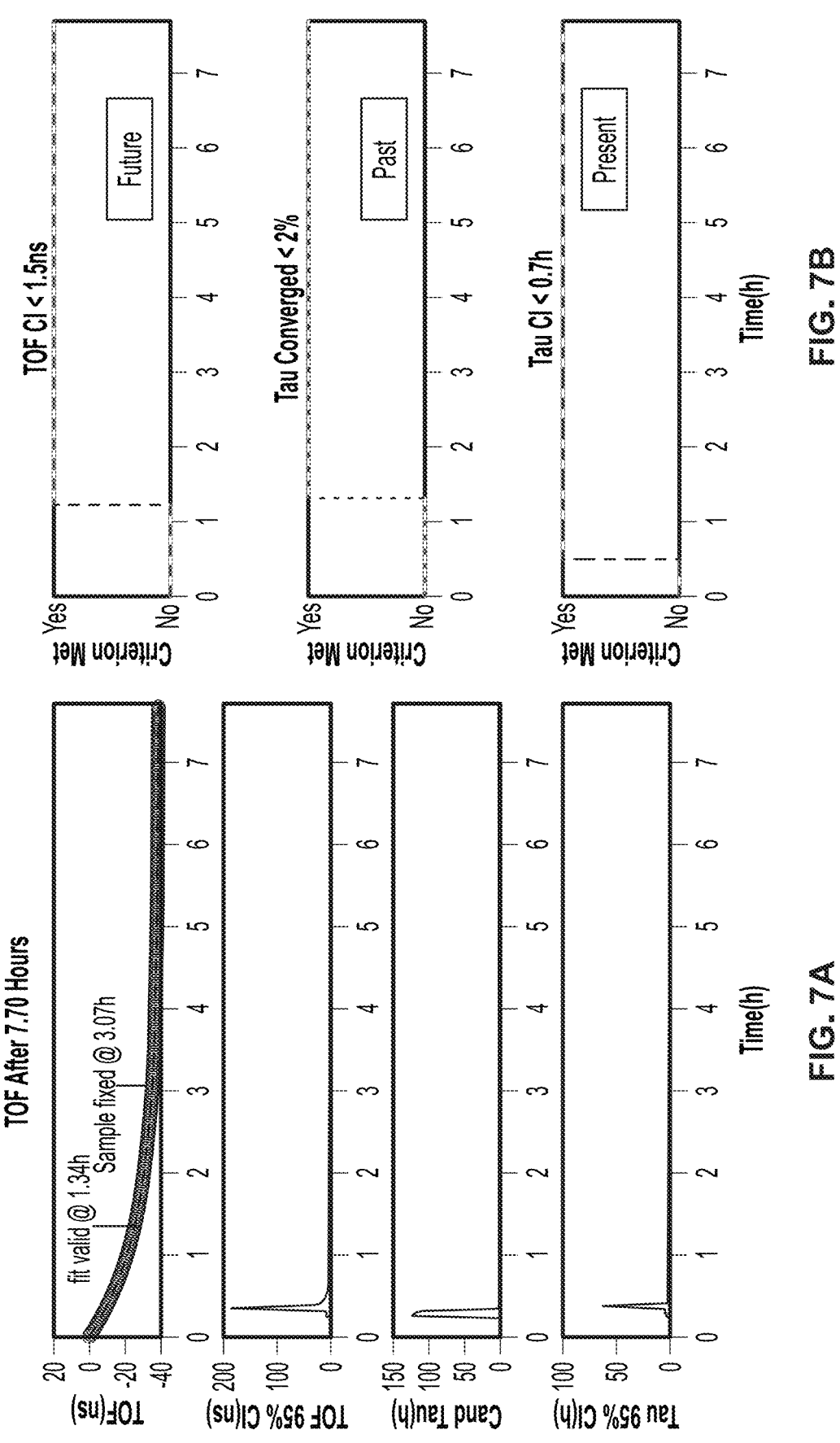
FIGS. 7A and 7B depict an example of determining if a TOF curve is valid in colon tissue. a) Top plot: TOF curve with black circles representing single TOF data points, the best-fit curve is depicted with a solid black line; the 95% confident interval is depicted with the dashed/dotted lines. Top-middle plot: The width of the 95% confident interval for the TOF curve. Bottom-middle plot: Candidate decay constant calculated using the most recent data point acquired. Bottom plot: 95% confidence interval of the decay constant. b) Graph of each individual confidence model for all time points in the experiment with a high value indicating criterion is met and a low value indicating criterion is not met. All three criteria must be simultaneously satisfied for the TOF signal to be deemed representative of the tissue's actual diffusion profile. (Top graph is future confidence model, middle graph is past confidence model, bottom graph is present confidence model).

FIG. 7 presents another example of criterion selection for a colon tissue sample. In this particular example, the future and past confidence models are satisfied earlier and the tissue is not deemed valid because the present confidence model has still not been satisfied.

Figures 8A, 8B:
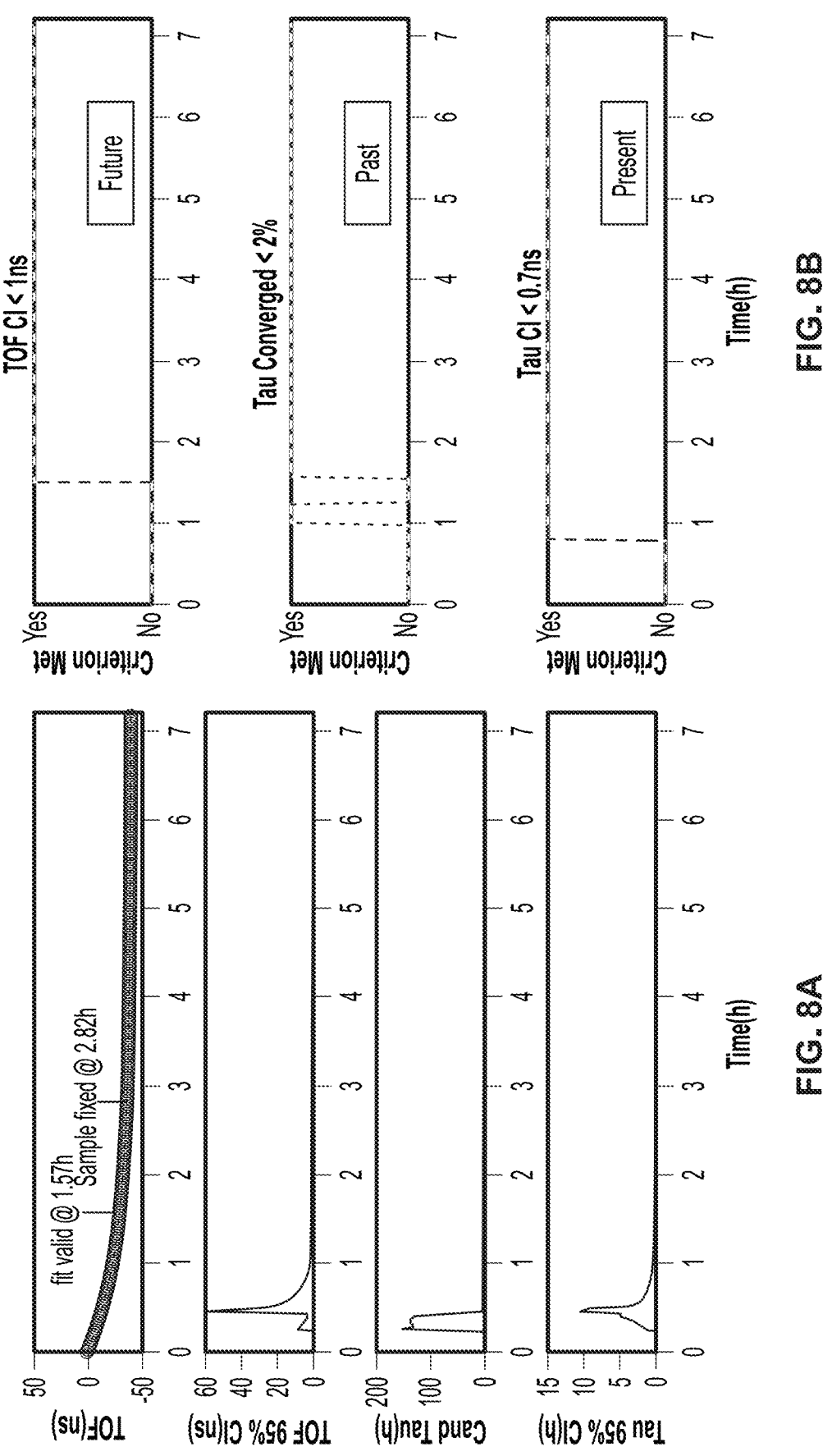
FIGS. 8A and 8B provide an example of determining if a TOF curve is valid in kidney tissue. a) Top plot: TOF curve with black circles representing single TOF data points, the best-fit curve is depicted with a solid black line; the 95% confident interval is depicted with the dashed/dotted lines. Top-middle plot: The width of the 95% confident interval for the TOF curve. Bottom-middle plot: Candidate decay constant calculated using the most recent data point acquired. Bottom plot: 95% confidence interval of the decay constant. b) Graph of each individual confidence model for all time points in the experiment with a high value indicating criterion is met and a low value indicating criterion is not met. In this specific example, all three criteria must be simultaneously satisfied for the TOF signal to be deemed representative of the tissue's actual diffusion profile. (Top graph is future confidence model, middle graph is past confidence model, bottom graph is present confidence model).

FIG. 8 shows a further example of criterion selection for a kidney tissue sample. In this case the future confidence model is the last confidence model to be satisfied whereas the present confidence model is satisfied almost immediately. The past confidence model is initially met but then reverses course. Thus, the future confidence model being unmet prevented the tissue from being called valid at a time point of about 1.5 hours.

Figures 9A, 9B:
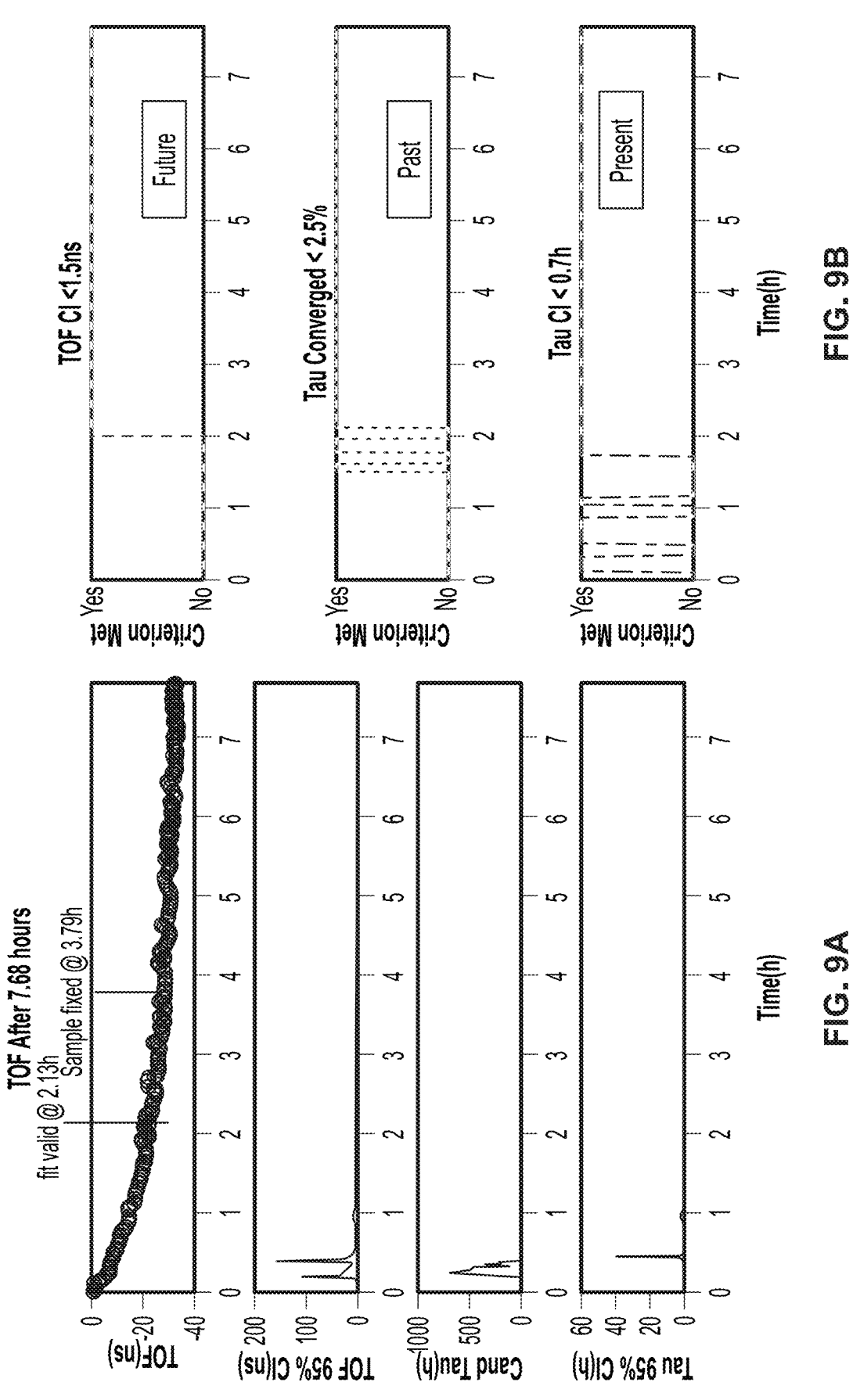
FIGS. 9A-9B show an example of determining if a TOF curve is valid in breast tissue. a) Top plot: TOF curve with black circles representing single TOF data points, the best-fit curve is depicted with a solid black line; the 95% confident interval is depicted with the dashed/dotted lines. Top-middle plot: The width of the 95% confident interval for the TOF curve. Bottom-middle plot: Candidate decay constant calculated using the most recent data point acquired. Bottom plot: 95% confidence interval of the decay constant. b)

FIG. 9 depicts yet another example of criterion selection for a breast tissue sample. In this instance the past and present confidence models "bounce" back and forth but the future confidence model is not met until 2 hours and prevents the signal from being called valid before it actually is.

The above examples illustrate how the three confidence models work together to create a system and/or method in which the TOF signal is not determined to be valid until it actually is. TOF has been used on many different types of tissue, as already disclosed, and demonstrated in (see FIG. 10A). Here, 105 samples from numerous types of tissue were used to evaluate the accuracy of the confidence models and hence the systems and methods described herein. Cumulative results are shown in FIG. 10B in which the time required to receive a valid fit is plotted versus the calculated optimal fixation time. On average, the sample fit converged to a valid fit before the sample was optimally fit in 102 out of 105 samples (97%). On average, at 2.04 hours tissue was determined to have a valid fit and an average fixation time of 2.96 hours was needed. This is an important finding because it indicates that, on average, tissue will be properly 0.92 hours after the TOF signal was proven valid.

Another method to assess the accuracy of the systems and methods which employ the three confidence models described herein is to retroactively compare the predicted optimal fixation time at convergence versus at the end of the experiment. These results are plotted in FIG. 11A. On average the optimal fixation time as converge time was only 0.45 h different than at the end of the experiment, which indicated a high degree of accuracy because there was not a significant different between the two values. Additionally, at the time of convergence, the TOF cure had a 95% confidence interval of only 0.44 ns and the decay constant had a 95% confidence interval of only 7 minutes (see FIG. 11B). Both of these numbers were very low and consistent with a high fidelity fit at the time the TOG signal was deemed valid.

Example 2

Summary

Modern histopathology is built on the cornerstone principle of tissue fixation, which traditionally uses room temperature aqueous formaldehyde (formalin) to preserve tissue in a lifelike state. Despite its paramount importance, there are currently no analytical methods of detecting fixation and as a result, in clinical practice fixation is highly variable and a significant source of error. It has been previously shown that immersion in cold formalin followed by heated formalin is beneficial for preservation of histomorphology because the cold phase enables unimpeded and thorough diffusion of formaldehyde before crosslinking is rapidly initiated in the heated phase. Additionally, a novel two-temperature fixation has been combined with ultra-sensitive acoustic monitoring technology that can actively detect formalin diffusing into a tissue. Here a predictive statistical model to determine when a tissue was properly diffused based on the real-time TOF signal has been developed. The model has been trained based on the morphology and characteristic diffusion curve of 30 tonsil cores. In the test model, a set of 87 different tonsil samples were fixed with four different protocols: dynamic fixation according to the disclosed predictive algorithm (C/H:Dynamic, N=18), gold-standard 24 hour room temperature (RT:24 hr, N=24), 6 hours in cold formalin followed by 1 hour in heated formalin (C/H:6+1, N=21), and 2 hours in cold formalin followed by 1 hour in heated formalin (N=24). For samples fixed using the dynamic fixation protocol, digital pathology analysis revealed that FOXP3 staining was spatially uniform with stain coverage levels statistically equivalent to RT:24 hr and C/H:6+1 fixation protocols. For comparison, the intentionally under fixed C/H:2+1 samples had significantly suppressed FOXP3 staining (p<0.002). Furthermore, the disclosed dynamic fixation protocol produced bcl-2 staining concordant with standard fixation techniques. The dynamically fixed samples were on average only submerged in cold formalin for 4.2 hours, representing a significant workflow improvement. These results establish that the disclosed developed system can correctly predict when a sample is sufficiently fixed and will generate high-quality histochemical staining. Indeed, it has been successfully demonstrated that the disclosed systems and methods allow for the assessment of the quality of fixation in real-time. Ultimately, it is believed that a future histology laboratory could utilize this analytical method to standardize and optimize tissue fixation as part of an expedited and fully documented preanalytical workflow.

Introduction

Clinical tissue processing techniques "fix" tissues with crosslinking agents that shut down metabolism within cells and preserve crisp and clear cellular morphology. The most prevalent fixative is 10% neutral buffered formalin (NBF) which is an aqueous solution of formaldehyde in a buffer and has been used for over a century (Fox et al. 1985). Currently, proper fixation protocols are empirically determined by examining the histologically stained tissue for proper morphological features. The result is a mixed bag of adequate and poor morphology depending on the operator, institution, tissue type, and biomarker of interest. Furthermore, by the time the morphology is interrogated, it is too late to improve the quality of the tissue so proper fixation the first time is critically important.

Tissue fixation is a time consuming process usually taking several hours to days depending on the type and size of the tissue. As pressures mount to decrease the turnaround time for patient care, rapid fixation protocols are being introduced. One such technology already being employed is to raise the temperature of the fixative to increase the cross-linking rate (Ferris et al. 2009; Iesurum et al. 2006; Antunes et al. 2006; Looi and Loh 2005; Hafajee and Leong 2004; Adams 2004; Morales et al. 2002; Arber 2002; Ruijter et al. 1997; Boon 1996; Ainley and Ironside 1994; Boon and Marani 1991; Kok and Boon 1990; Leong 1988; Boon et al. 1988; Leong and Duncis 1986; Kok et al. 1986; Boon, Kok, and Ouwerkerk-Noordam 1986; Leong, Daymon, and Milios 1985). While this is practically effective, the use of increased fixative temperature has led to many reports of unsatisfactory tissue morphology based on hematoxylin and eosin (H&E) stain and variability in other molecular analysis, such as routine immunohistochemical (IHC) stains (Durgun-Yucel et al. 1992; Dawson 1972; Ericsson and Biberfeld 1967). Biologically, the use of heated fixative serves to crosslink proteins on the outside of the tissue sample while compromising the structure of proteins in the middle where sufficient fixative has not penetrated. A more promising rapid method that produces superior tissue fixation uses 10% NBF in two-temperature zones (cold+hot) (Chafin et al. 2013, Theiss et al. 2014). The cold step allows proper diffusion of formaldehyde into the tissue interior followed by a short, heated phase that rapidly forms formaldehyde-based crosslinks.

Presently there are no established methods of actively monitoring either the diffusion of formaldehyde into tissues or the actual formation of crosslinks. Inadequately diffused tissues will only crosslink and fix where the fixative has penetrated, forming an outer ring of well-fixed tissue. Inadequate fixation is a leading cause of reported errors in anatomical pathology laboratories (Mathews, Newbury, and Housser 2011; Engel and Moore 2011; De Marzo et al. 2002; Plebani et al. 2015; Plebani 2015; Bonini et al. 2002). Because current tissue fixation protocols lack real-time monitoring there is no way to guarantee sufficient formaldehyde concentrations in the tissue or conversely to know if a sample has become over fixed, which also has detrimental effects on stain quality (Singhal et al. 2016; Arber 2002). In short, current fixation techniques offer no quality assurance or tracking capability to tissue processing laboratories. This means when samples are improperly fixed expensive rework is required, if another sample is capable of being procured again at all. Although several methods for statically detecting diffusion exist including optical, ultrasound, and MRI, these detection mechanisms have not been implemented for tissue processing to better preserve cancer indicators (Partridge et al. 2012; Uhl M. 2014; Tanimoto et al. 2007; Petriaek and Schwille 2008; DuMond and Youtz 2004). Some researchers have soaked tissues in radioactive formaldehyde and measured fluid penetration after exposure to photographic film as a measure of diffusion rates (Helander 1994). However, very little radioactivity is actually incorporated into the tissue and long exposure times led to fuzzy and unreliable results. Others have used ultrasound monitoring to look at crosslinking by comparing samples of unfixed to fixed tissues (Oldenburg and Boppart 2010; Hall et al. 2000; Bamber, Hill, and King 1981; Bamber and Hill 1981; Bamber et al. 1979; Bamber and Hill 1979). Ultimately, neither of these techniques allows for monitoring in real-time when changes could be implemented to guarantee excellent tissue fixation and proper functional staining.

Therefore, to ensure sufficient formaldehyde was present throughout a tissue to guarantee proper staining, a dynamic method to optimize tissue fixation using real-time detection of formalin diffusion was developed (such as described herein). An automated system that can detect penetration of a fixative into a raw biological tissue using acoustic time-of-flight (TOF) technology that exploits the discrete sounds velocities of interstitial fluid and formalin has been previously described (Bauer et al. 2016). As formalin diffuses into a tissue specimen and replaces exchangeable fluid (e.g., interstitial fluids), the overall composition of the tissue is physically altered resulting in a TOF differential. As faster formalin diffuses into the sample the tissue's net sound velocity increases resulting in a monotonic decrease to the TOF signal. The present disclosure is directed to a real-time statistical model and custom-modified tissue processor system that determines when a sample is adequately diffused enough to produce high-quality staining from downstream IHC assays.

Methods

Tissue Acquisition and Fixation

Human tonsil tissue was obtained fresh and unfixed from a local Tucson, Arizona hospital under a contractual agreement with approved protocols. Whole tonsils from same day surgeries were transported to Roche Tissue Diagnostics on wet ice in biohazard bags. Samples of tonsil tissues of precise sizes were obtained by using 6 mm diameter biopsy punch (Miltex #33-36). For cold+hot fixation, 6 mm tonsil cores were placed into 10% NBF (Saturated aqueous formaldehyde from Fisher Scientific, Houston, Texas, buffered to pH 6.8-7.2 with 100 mM phosphate buffer) previously chilled to 4°. Samples were then removed and placed into 45° C. NBF for an additional 1 hour to initiate crosslinking. Other punches were placed into room temperature NBF for 24 hours to serve as positive controls for well-fixed tissue. Additional biopsy punches were secured in tissue cassettes and placed in between the TOF sensors on the automated fixation device. After fixation, samples were processed in a commercial tissue processor set to an overnight cycle and embedded into wax.

Time-of-Flight Measurement

Briefly, pairs of 4 MHz focused transducers were spatially aligned and tissue samples were placed at their common foci. One transducer was programmed to send out a sinusoidal pulse that was detected by an accompanying transducer after traversing the formalin and tissue and the received pulse was used to calculate the transit time. An initial calibration TOF reading was acquired by measuring the signal through only formalin. That baseline reading was subtracted from the TOF with the tissue present to isolate the phase alteration from the tissue. This detection method simultaneously isolated the acoustic TOF shift due to diffusion and compensated for environmentally-induced fluctuations in the formalin. Multiple TOF measurements were recorded throughout each tissue specimen and the spatially averaged signal was recorded as representative of the tissue's overall rate of formalin diffusion. In practice, the form of the TOF diffusion signal from multiple tissue types was well-correlated with a single-exponential decay function. (Lerch et al. 2017).

Histology

Paraffin tissue blocks were sectioned to 4 μm thick and placed onto Fisherbrand™ Superfrost™ Plus microscope slides (Thermo Fisher Scientific). One section was stained with H&E on a Ventana Medical Systems HE600 automated staining system to evaluate tissue morphology. Additionally, to evaluate IHC stain intensity and coverage serial sections of each block were stained for anti-FOXP3 (SP33) or anti-bcl-2 (SP66) with Di-aminobenzidine (DAB) stain according to the manufacturer's protocol on a Ventana Benchmark Ultra XT automated staining system.

Statistical Modeling

The statistical model used to calculate in real-time when the TOF signal was representative of the tissue's actual diffusion rate was initially developed using custom developed code written in MATLAB (Mathworks) using multiple functions from the Statistics and Machine Learning toolbox. When the final model was translated to the laboratory for implementation on our TOF-scanning hardware, it was translated into Python using several libraries including numpy, matplotlib, scipy, and kapteyn.

Imaging and Image Processing

Each slide was imaged on a whole slide scanner (VENTANA iScan HT slide scanner) at 20× magnification with DAB stain and a hematoxylin counterstain. A custom developed software package written in MATLAB was used to analyze the images. A segmentation algorithm differentiated the entire tissue section from the background. A separate algorithm identified regions within the tissue footprint that comprised non-staining tissues (e.g., holes, cracks, stroma), to yield the most representative statistics around percent of tissue staining. The transmission images were log transformed and spectrally unmixed to isolate the DAB staining from the hematoxylin counterstain. The unmixed DAB concentration mappings were used to determine which pixels were DAB positive using a global threshold. Raw DAB concentrations were also recorded so the intensity of DAB staining could be analyzed. To study the effects of improper fixation, an algorithm was written that calculated the Euclidean distance to the nearest edge pixel so that intensity of DAB stain and DAB positivity could be studied for different fixation protocols.

Results

Criterion for Real-Time Prediction of Stain Quality

To construct a model that could predict optimal fixation quality in real-time, the relationship between formalin diffusion and morphological properties needed to be understood. Diffusion is controlled mainly by concentration gradients and time according to Fick's Laws of diffusion. Several time course experiments were performed using 6 mm cores of human tonsil tissues submerged into 4° C. NBF followed by 1 hour in 45° C. NBF (Lerch et al. 2017). After multiple experiments were analyzed, a minimum of 3 hours of cold NBF (C/H:3+1) was determined to produce acceptable histomorphology. Tissue morphology was improved with 5 hours in cold NBF (C/H:5+1) but further cold soak times provided no additional benefit. Multiple cores were then examined and it was confirmed that a C/H:5+1 protocol produced high-quality staining, see cumulative results in FIG. 12A.

In the previous section, the diffusion times required to produce high-quality H&E staining were empirically determined. Next, the diffusivity properties of human tonsil tissues were quantitatively characterized to develop an analytical metric to determine when a sample was properly diffused. Several whole tonsil tissues were cored to 6 mm in diameter. A total of 38 6 mm tonsil samples were measured in cold (7±0.5° C.) 10% NBF. Of the 38 samples, 14 were monitored for 3 hours and the remaining 24 samples were monitored for 5 hours. For each sample the diffusion was measured throughout the sample (1 mm intervals) and the spatially-averaged TOF curves were calculated. The characteristic TOF-based diffusion signals were highly correlated with a single-exponential curve of the form, $$TOF(t) = A_{avg} * e^{\frac{-t}{\tau_{avg}}} + C \qquad \text{(Equation 13)}$$

where C is a constant offset in nanoseconds, $A_{avg}$ is the amplitude of the exponential decay in nanoseconds, and τavg is the tissue's average decay constant in hours. Samples scanned for 3 hours and 5 hours had average decay constants of 2.33 hours and 2.72 hours, respectively. The difference of 0.39 hours was statistically insignificant, indicating that the two datasets faithfully measured the same physical phenomena. This established that the TOF measurement system produced consistent and reproducible results for long and short diffusion times.

Figure 13B:
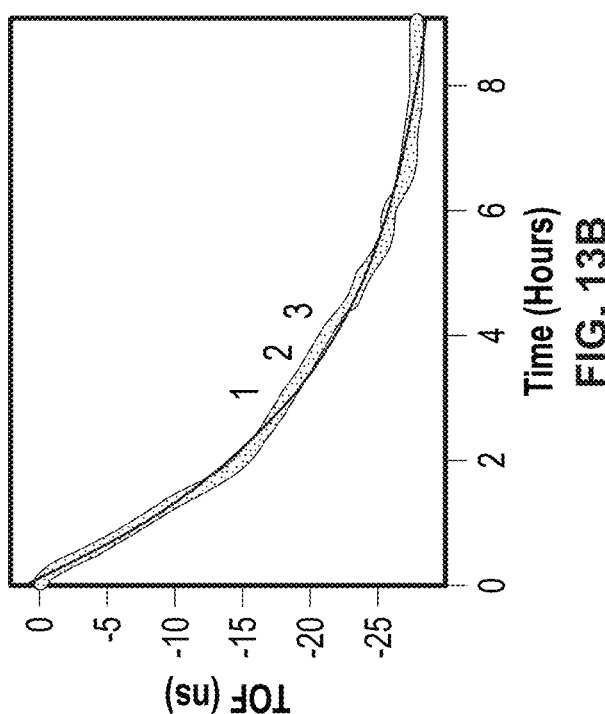
Figure 13A:
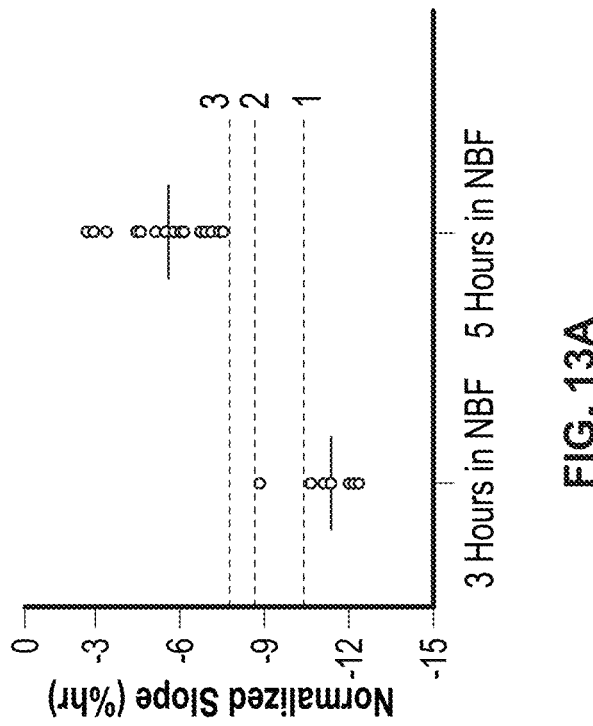

Having validated the diffusion monitoring system, the dataset of thirty-eight (38) 6 mm tonsil samples was analyzed to find a correlation between the diffusive properties of each tissue and the empirically determined diffusion times required to produce ideal downstream staining. Numerous analytic techniques were employed including multivariate analysis, cluster based algorithms, characterization of the signal's derivative, and principal component analysis. A slope based analysis, physically representing the rate of diffusion, was found to provide ideal and meaningful discrimination of samples that were in cold formalin for 3 hours (i.e., adequately staining) versus 5 hours (i.e., optimally staining throughout the sample). To significantly mitigate noise and more accurately represent the active rate of diffusion, the derivative of the TOF signal was calculated based on a fit to a single exponential function. Additionally, ideal discrimination of the two datasets was achieved by amplitude-normalizing each signal, $$m(t = t_o) = 100\left(\frac{-1}{\tau_{avg}}e^{\frac{-t_o}{\tau_{avg}}}\right)\left[\frac{\%}{\text{hr}}\right] \qquad \text{(Equation 14)}$$

where m is the derivative of the amplitude-normalized TOF signal at time to and the brackets denote the slope's units of percent TOF change per hour of diffusion. FIG. 13A displays the normalized slope, at 3 hours and 5 hours respectively, of each sample. The average rate of diffusion at 3 hours was −11.3%/hr, whereas at 5 hours the rate of diffusion had significantly slowed to −5.3%/hr, with several samples approaching full osmotic equilibrium as indicated by a near zero rate of diffusion. The different distributions of normalized rates of diffusion at 3 hours and 5 hours were highly statistically significant (p<2e-15), indicating a drastic and physically real difference in the rate of diffusion at 3 hours versus 5 hours. Thus, the TOF-based diffusion metric and H&E-based stain quality were highly-correlated, indicating our diffusion monitoring system, if properly calibrated, was fundamentally capable of predicting eventual stain quality. Given this validation, the equation below was solved for the time required to reach a criterion rate of NBF diffusion, $$t_{done}(\tilde{m}) = -\tau_{avg} \ln(|\tilde{m}_{thres} \cdot \tau_{avg}|) \qquad \text{(Equation 15)}$$

where $t_{done}$ is the time required to reach a threshold slope ($m_{thres}$), and the | . . . | symbol indicates the absolute value. For a given tissue specific decay constant and normalized rate of diffusion, this equation can be used to calculate how long a sample needs to be in cold formalin before it will reach a threshold rate of diffusion. To evaluate rate of diffusion as a stain quality predictor, three threshold slope values ($m_{thres}$=−7.4%/hr, −8.0%/hr, −10.4%/hr) were chosen for evaluation, as displayed visually in FIG. 13A. Note that large absolute slope values represent more fluid exchange per hour. Thus, as a sample's active diffusion slows, the rate of diffusion will approach osmotic equilibrium (i.e., 0%/hr). Therefore, a larger threshold slope criterion predicts samples have adequate formaldehyde sooner. This is illustrated graphically in FIG. 13B on a representative 6 mm piece of human tonsil, where decreasing diffusion rates translate to longer completion times.

Additionally, the projected completion times for tissues in each dataset (3 hours and 5 hours) are displayed in FIGS. 13C-E as calculated from the equation provided above. For example, FIG. 13C displays the projected completion times for the largest threshold slope of −10.4%/hr. This slope criterion predicted an average completion time of 3.27 hours. However, six (6) of the sample's (16%) projected completion times are less than 3 hours and from our previous histological staining results, these samples are known to not be adequately diffused throughout. Additionally, one sample would be misidentified with this slope criterion. Based on these findings all samples must not have sufficient formalin to stain acceptably when their rate of diffusion is −10.4%/hr. The middle threshold slope value of −8.0%/hr produces ideal discrimination between the two datasets and reasonable completion times between 3 and 5 hours. However, to be as conservative as possible, the lowest threshold slope value of −7.4%/hr was selected as the criterion for when samples will stain optimally throughout. With this metric, 6 mm tonsil cores were projected to take between 3.21 hours and 4.96 hours, from downstream histological staining this was understood to be reasonable. Based on these experiments and analysis, once a sample's real-time rate of normalized diffusion slows to, $$\tilde{m}_{thres}(t) \le -7.4\%/\text{hr}$$

the sample will have sufficient formalin throughout to guarantee ideal and uniform histological staining.

Statistical Model for Real-Time Validation of TOF Signal

A practical embodiment of the TOF technology requires the diffusion curve to be analyzed with temporally sparse data in the absence of a ground truth assessment of the tissue's true temporal diffusion profile. For instance, the prediction of when a sample is optimally fixed is based on the detected rate of NBF diffusion at a given time. However, this prediction is only valid if the exponential fit of the tissue's diffusion curve is representative of the tissue's actual rate of diffusion. In particular at the beginning of an experiment when data is sparse, the detected rate of diffusion can change significantly due to a variety of sources (e.g., tissue deformation, thermal noise, fluidic variables, etc.) in addition to noise inherent to the TOF calculation. To overcome these limitations, a statistical model to validate when the TOF curve had converged to the true diffusion profile of the tissue was developed and was therefore accurate enough to make a prediction as to whether the sample was adequately fixed.

The developed solution was a statistical model that had three independent components that query different components of the TOF signal. All three components were continually re-calculated as TOF data points were calculated during cold NBF diffusion. When all three statistical parameters were simultaneously satisfied, the diffusion profile was judged to be accurate.

Condition #1 (Past Confidence model): This condition establishes that the current TOF fit is consistent with previously collected data. In this example, the decay constant of the single exponential line must converge, as defined by 10 consecutive decay constants having less than a 2% difference relative to the average of the previous 6 decay constants.

Condition #2 (Present Confidence model): This condition establishes the statistical confidence of the presently collected data. In this example, the 95% percent confidence interval of the most recent decay constant must be below 0.7 hours.

Condition #3 (Future Confidence model): This condition establishes that there is sufficient statistical confidence to predict future TOF values. In this example, the 95% confidence interval of the TOF signal across all times (past, present, and future) must be below 2 ns.

Once all three statistical conditions were satisfied, the confidence model validated that the TOF signal from the tissue was representative of the actual rate of diffusion and predicted at what time the tissue will be properly fixed according to Equation 14 with the threshold condition described in Equation 15. A graphical depiction of the real-time statistical model is displayed in FIG. 14A where the TOF diffusion signal was judged representative at 3.08 hours, at which point the predictive confidence model calculated the tissue would be properly diffused at 4.47 hours. The calculation of the present, future, and past confidence models, up to the point they were satisfied, is plotted in FIGS. 14B, 14C, and 14D, respectively.

The overall efficacy of the methodology was tested on 105 previously collected TOF curves (Lerch et al. 2017). A simulation was written in which this a priori data was analyzed by the statistical model to simulate how it would behave on real-life empirical data. At the time the model validated the signal, the predicted time of optimal fixation was calculated to be within 27 minutes of the true time, as calculated by the fit at the end of the experiment. The statistical confidence of the decay constant at the time of convergence was ±7 minutes. These results confirm that the model determined in real-time when the TOF signal was representative of the tissue's actual rate of diffusion and that predictions based on that data were accurate. FIG. 14E plots the time to validate characteristic diffusion curves versus the predicted fixation times. On average, the model converged to a valid fit 55 minutes before the sample was properly diffused. These results detail how the model was capable of determining when biospecimen will be optimally diffused nearly an hour before they were, and thus established the feasibility of a commercial embodiment of TOF-based diffusion monitoring coupled with a real-time assessment of fixation quality.

Validation of Fixation Predictive Model with IHC Staining

To confirm that the developed predictive model was truly predictive of eventual stain quality, digital pathology tools to objectively and repeatably evaluate the level of staining of each slide were developed. Digital analysis was performed on IHC slides with DAB staining a single marker and hematoxylin counterstain. A whole slide scan of each slide was acquired. The software segmented the tissue, and identified and removed areas that did not stain, such as connective tissue and stroma. For all regions with active staining, the software quantified the percent of the tissue that was DAB positive. Additionally, it calculated the edge distance, defined as the shortest possible distance to the border of the tissue sample. Next radial concentric 0.33 mm "zones" of the tissue were calculated so staining could be analyzed in regions with roughly equal concentrations of formalin. This geometrical representation of the tissue enabled the effects of improper fixation to be explicitly analyzed because formalin diffuses into a tissue from the periphery resulting in progressively less staining at the core of the tissue. A histogram was calculated plotting the percent of the tissue staining versus distance to the nearest tissue edge. Finally, each radial zone of the tissue was analyzed for proper staining by defining suppressed staining as DAB positivity less than half of the edge/maximum positivity. A graphical depiction of the image analysis workflow is presented in FIG. 15.

To confirm that the disclosed system and method could accurately ascertain in real-time when a tissue was optimally diffused, a large scale study with 87 distinct tonsil cores differentially fixed with one of four fixation protocols was studied. For all fixation protocols, after fixation tissues were processed in a standardized fashion, embedded in paraffin blocks, and slides were cut and stained with DAB for FOXP3 and bcl-2. The first three fixation protocols were: cold NBF for 2 hours followed by heated NBF for 1 hour (C/H: 2+1, N=24), cold NBF for 6 hours followed by heated NBF for 1 hour (C/H: 6+1, N=21), and room temperature NBF fixation for 24 hours (RT:24 hr, N=24). Finally, real-time fixation prediction algorithm was tested using the cold+hot fixation method in which tonsils were placed in cold NBF until our system determined they were sufficiently diffused at which point they were moved to heated formalin for 1 hour to initiate crosslinking (C/H:Dynamic, N=18). In this experiment, the C/H:6+1 and RT:24 hr protocols represented internal controls because these fixation methods were known to produce high-quality staining. Alternatively, the C/H:2+1 samples represented intentionally under fixed tissues. Representative images of the staining patterns for each fixation method are displayed in FIG. 16. The two standard fixation protocols produced tissue that stained nearly uniformly whereas the C/H:2+1 tissue had significantly suppressed staining at the center of the tissue. Importantly, the tissue from the C/H:Dynamic protocol produced uniform FOXP3 staining consistent with the two gold-standard fixation protocols.

Furthermore, cumulative box and whisker plots for the entire 87 tissue study for FOXP3 staining are presented in FIG. 17. The stain penetration depth, as defined by the distance at which staining drops to half its edge value, is plotted in FIG. 17A and the area of the tissue that properly stained is plotted in FIG. 17B. For both metrics the C/H:2+1 samples exhibited significantly reduced staining compared to the other three fixation methods (p<0.002). Importantly, C/H:Dynamic samples displayed staining results that were concordant with both the RT:24 hr samples as well as C/H:6+1 samples. Additionally, dynamically fixed samples were in cold NBF for only 4.2 hours, meaning the TOF predictive algorithm produced tissues that stained as well as traditionally fixed tissues but several hours faster. Additionally, the average spatial stain profile for FOXP3 for all four fixations protocols is plotted in FIG. 17C. The dynamically fixed samples again displayed a staining pattern consistent with C/H:6+1 and RT:24 hr fixation. This is in marked contrast to the C/H:2+1 samples that had roughly 70% less staining at the center versus the edge of the tissue.

Discussion

A dominate source of error in the histology laboratory is caused by improperly fixed tissues, resulting in decreased stain intensity and poor morphology (Mathews, Newbury, and Housser 2011; Engel and Moore 2011; De Marzo et al. 2002). In this work, it has been shown the development of a first-of-its-kind tissue fixation system capable of determining in real-time when a biospecimen has adequate formaldehyde to guarantee high-quality fixation as demonstrated by ideal and spatially uniform functional staining from downstream IHC assays. The predictive algorithm was trained on a combination of H&E-based morphology as well as characteristic diffusion curves from tonsil samples. Ultimately, our system was validated by comparing staining results from different fixation protocols. Dynamically fixed samples, with diffusion times actively controlled by our statistical model, were found to have equivalent FOXP3 and bcl-2 staining compared to the current clinical gold-standard of 24 hour room temperature fixation.

In today's histology lab, the process of tissue fixation is largely dictated by workflow considerations, rather than on scientific principles, with protocols that can vary significantly at different institutions. One difficulty of having multiple non-standardized procedures is the inability to share data and results easily across multiple sites. Clinicians would benefit greatly from data collected from standardized samples that were treated with the same fixation protocol. For instance, digital pathology algorithms can output inconsistent results when analyzing samples with improper preanalytical processing. More consistent staining levels are reported with properly fixed tissues compared to poorly fixed samples for FOXP3 and bcl-2 staining (FIG. 19). Another benefit of standardizing tissue fixation is increased efficiency which would reduce the amount of costly re-work due to poor quality or lost tissues. The costs of this re-work often falls on the testing lab and could be greatly reduced with a standardized system as part of a fully documented preanalytical workflow.

It has been previously demonstrated that a novel fixation protocol, based on two temperature zones, better preserves labile biomarkers such as phospho-proteins and mRNA (Theiss 2017, Increased detection of RNA species in histological tissues using a two temperature fixation protocol). More rapid and efficient techniques, such as two-temperature fixation, will become necessary as the number of samples continues to increase and diagnostic assays rely on next generation biomarkers. The present disclosure provides a system to take advantage of this more efficient method of fixing tissues by standardizing formaldehyde penetration. Histology practices have been around for decades and these practices are difficult to change. The methods and instrumentation described herein take advantage of the same reagents (10% NBF) and procedures (formaldehyde crosslinking) and therefore do not alter downstream assay protocols or results. Rather, this and other more efficient methods of tissue standardization will be necessary to enable accurate preservation and quantitation of future analytes.

In this work a system and method has been tested and validated using FOXP3 expression in human tonsil samples, however, it is believed the system and method will be applicable to all biomarkers and tissue types. For example, additional data relating to faithful preservation of bcl-2 with our novel fixation method is presented herein. The dynamic fixation protocol demonstrated equivalent staining to clinical 24 hour room temperature fixation (compare FIGS. 18 and 19). The expression pattern for bcl-2 did not show a heavy dependence on fixation quality, which was expected because it is a known as a robust clinical biomarker. This result highlights that improved fixation will be particularly beneficial for labile biomarkers. Analysis of staining intensity for differentially fixed tissues is presented in FIG. 20. Additionally, diffusion data for 34 different tissue types has been previously generated and shown that each has its own characteristic diffusion rate and therefore the disclosed predictive statistical model can be applied to multiple tissue types (FIG. 20) (Bauer et al. 2016).

One of the next steps for this technology is to explore the use of this predictive algorithm empirically on other tissue types and biomarkers, in particular biomarkers known to be preanalytically sensitive. Future work will entail extending our current criterion, developed with tonsil tissue, to a plurality of tissue types so that a universal fixation criterion can be realized. It is postulated that the current metrology can be tuned to create a generalizable model that can optimally predict when all types of tissue are appropriately fixed. It is believed the histology lab of the future could employ this analytical method as part of a random-access automated processing unit that could ensure and document that individual tissue samples are optimally fixed, and truly transform tissue fixation into a science.

REFERENCES

Adams, D. 2004. 'Microwave-assisted rapid tissue processing', Am J Clin Pathol, 122: 612-3; author reply 13-4.

Ainley, C. D., and J. W. Ironside. 1994. 'Microwave technology in diagnostic neuropathology', J Neurosci Methods, 55: 183-90.

Antunes, L., K. Montagne, N. Weinbreck, L. Marchal, D. Thiebault, C. Bonnet, D. Gauche, and F. Plenat. 2006. 'Possible role of tissue shrinkage in high-temperature antigen retrieval', Histopathology, 48: 471-3.

Arber, D. A. 2002. 'Effect of prolonged formalin fixation on the immunohistochemical reactivity of breast markers', Appl Immunohistochem Mol Morphol, 10: 183-6.

Bamber, J. C., and C. R. Hill. 1979. 'Ultrasonic attenuation and propagation speed in mammalian tissues as a function of temperature', Ultrasound Med Biol, 5: 149-57.

'Acoustic properties of normal and cancerous human liver-I. Dependence on pathological condition', Ultrasound Med Biol, 7: 121-33.

Bamber, J. C., C. R. Hill, and J. A. King. 1981. 'Acoustic properties of normal and cancerous human liver-II. Dependence of tissue structure', Ultrasound Med Biol, 7: 135-44.

Bamber, J. C., C. R. Hill, J. A. King, and F. Dunn. 1979. 'Ultrasonic propagation through fixed and unfixed tissues', Ultrasound Med Biol, 5: 159-65.

Bauer, D. R., M. Otter, and D. R. Chafin. 2018. 'A New Paradigm for Tissue Diagnostics: Tools and Techniques to Standardize Tissue Collection, Transport, and Fixation', Curr Pathobiol Rep, 6: 135-43.

Bauer, D. R., B. Stevens, D. Chafin, A. P. Theiss, and M. Otter. 2016. 'Active monitoring of formaldehyde diffusion into histological tissues with digital acoustic interferometry', J Med Imaging (Bellingham), 3: 017002.

Bonini, P., M. Plebani, F. Ceriotti, and F. Rubboli. 2002. 'Errors in laboratory medicine', Clin Chem, 48: 691-8.

Boon, M. E. 1996. 'Microwave-antigen retrieval: the importance of pH of the retrieval solution for MIB-1 staining', Eur J Morphol, 34: 375-9.

Boon, M. E., P. O. Gerrits, H. E. Moorlag, P. Nieuwenhuis, and L. P. Kok. 1988. 'Formaldehyde fixation and microwave irradiation', Histochem J, 20: 313-22.

Boon, M. E., L. P. Kok, and E. Ouwerkerk-Noordam. 1986. 'Microwave-stimulated diffusion for fast processing of tissue: reduced dehydrating, clearing, and impregnating times', Histopathology, 10: 303-9.

Boon, M. E., and E. Marani. 1991. 'The major importance of temperature data in publications concerning microwave techniques', Eur J Morphol, 29: 184-5.

Chafin, D., A. Theiss, E. Roberts, G. Borlee, M. Otter, and G. S. Baird. 2013. 'Rapid two-temperature formalin fixation', PLoS One, 8: e54138.

Dawson, I. M. 1972. 'Fixation: what should the pathologist do?', Histochem J, 4: 381-5.

De Marzo, A. M., H. H. Fedor, W. R. Gage, and M. A. Rubin. 2002. 'Inadequate formalin fixation decreases reliability of p27 immunohistochemical staining: probing optimal fixation time using high-density tissue microarrays', Hum Pathol, 33: 756-60.

DuMond, Jesse, and J. Paul Youtz. 2004. 'An X-Ray Method of Determining Rates of Diffusion in the Solid State'.

Durgun-Yucel, B., F. Dere, A. H. Yucel, and O. Oguz. 1992. 'Rapid fixation of whole organ specimens and attendant problems', Acta Med Okayama, 46: 75-81.

Engel, K. B., and H. M. Moore. 2011. 'Effects of preanalytical variables on the detection of proteins by immunohistochemistry in formalin-fixed, paraffin-embedded tissue', Arch Pathol Lab Med, 135: 537-43.

Ericsson, J. L., and P. Biberfeld. 1967. 'Studies on aldehyde fixation. Fixation rates and their relation to fine structure and some histochemical reactions in liver', Lab Invest, 17: 281-98.

Ferris, A. M., R. T. Giberson, M. A. Sanders, and J. R. Day. 2009. 'Advanced laboratory techniques for sample processing and immunolabeling using microwave radiation', J Neurosci Methods, 182: 157-64.

Fox, C. H., F. B. Johnson, J. Whiting, and P. P. Roller. 1985. 'Formaldehyde fixation', J Histochem Cytochem, 33: 845-53.

Hafajee, Z. A., and A. S. Leong. 2004. 'Ultra-rapid microwave-stimulated tissue processing with a modified protocol incorporating microwave fixation', Pathology, 36: 325-9.

Hall, C. S., C. L. Dent, M. J. Scott, and S. A. Wickline. 2000. 'High-frequency ultrasound detection of the temporal evolution of protein cross linking in myocardial tissue', IEEE Trans Ultrason Ferroelectr Freq Control, 47: 1051-8.

Helander, K. G. 1994. 'Kinetic studies of formaldehyde binding in tissue', Biotech Histochem, 69: 177-9.

Iesurum, A., T. Balbi, D. Vasapollo, A. Cicognani, and C. Ghimenton. 2006. 'Microwave processing and ethanol-based fixation in forensic pathology', Am J Forensic Med Pathol, 27: 178-82.

Kok, L. P., and M. E. Boon. 1990. 'Physics of microwave technology in histochemistry', Histochem J, 22: 381-8.

Kok, L. P., M. E. Boon, E. Ouwerkerk-Noordam, and P. O. Gerrits. 1986. 'The application of a microwave technique for the preparation of cell blocks from sputum', J Microsc, 144: 193-9.

Leong, A. S. 1988. 'Microwave irradiation in histopathology', Pathol Annu, 23 Pt 2: 213-34.

Leong, A. S., M. E. Daymon, and J. Milios. 1985. 'Microwave irradiation as a form of fixation for light and electron microscopy', J Pathol, 146: 313-21.

Leong, A. S., and C. G. Duncis. 1986. 'A method of rapid fixation of large biopsy specimens using microwave irradiation', Pathology, 18: 222-5.

Lerch, M. L., D. R. Bauer, D. Chafin, A. Theiss, M. Otter, and G. S. Baird. 2017. 'Precision Medicine Starts With Preanalytics: Real-Time Assessment of Tissue Fixation Quality by Ultrasound Time-of-Flight Analysis', Appl Immunohistochem Mol Morphol, 25: 160-67.

Looi, L. M., and K. C. Loh. 2005. 'Microwave-stimulated formaldehyde fixation of experimental renal biopsy tissues: computerised morphometric analysis of distortion artefacts', Malays J Pathol, 27: 23-7.

Mathews, M., J. Newbury, and E. M. Housser. 2011. 'Shaping policy: the Canadian Cancer Society and the Hormone Receptor Testing Inquiry', Curr Oncol, 18: 174-9.

Middleton, L. P., K. M. Price, P. Puig, L. J. Heydon, E. Tarco, N. Sneige, K. Barr, and M. T. Deavers. 2009. 'Implementation of American Society of Clinical Oncology/College of American Pathologists HER2 Guideline Recommendations in a tertiary care facility increases HER2 immunohistochemistry and fluorescence in situ hybridization concordance and decreases the number of inconclusive cases', Arch Pathol Lab Med, 133: 775-80.

Morales, A. R., H. Essenfeld, E. Essenfeld, M. C. Duboue, V. Vincek, and M. Nadji. 2002. 'Continuous-specimen-flow, high-throughput, 1-hour tissue processing. A system for rapid diagnostic tissue preparation', Arch Pathol Lab Med, 126: 583-90.

Oldenburg, A. L., and S. A. Boppart. 2010. 'Resonant acoustic spectroscopy of soft tissues using embedded magnetomotive nanotransducers and optical coherence tomography', Phys Med Biol, 55: 1189-201.

Partridge, Savannah C., Christiane D. Mullins, Brenda F. Kurland, Michael D. Allain, Wendy B. DeMartini, Peter R. Eby, and Constance D. Lehman. 2012. 'Apparent Diffusion Coefficient Values for Discriminating Benign and Malignant Breast MRI Lesions: Effects of Lesion Type and Size', American Roentgen Ray Society.

Petrášek, Zdeněk, and Petra Schwille. 2008. 'Precise Measurement of Diffusion Coefficients using Scanning Fluorescence Correlation Spectroscopy', Biophysical Journal, 94: 1437-48.

Plebani, M. 2015. 'Diagnostic Errors and Laboratory Medicine—Causes and Strategies', EJIFCC, 26: 7-14.

Plebani, M., L. Sciacovelli, A. Aita, M. Pelloso, and M. L. Chiozza. 2015. 'Performance criteria and quality indicators for the pre-analytical phase', Clin Chem Lab Med, 53: 943-8.

Ruijter, E. T., G. J. Miller, T. W. Aalders, C. A. van de Kaa, J. A. Schalken, F. M. Debruyne, and M. E. Boon. 1997. 'Rapid microwave-stimulated fixation of entire prostatectomy specimens. Biomed-II MPC Study Group', J Pathol, 183: 369-75.

Singhal, P., N. N. Singh, G. Sreedhar, S. Banerjee, M. Batra, and A. Garg. 2016. 'Evaluation of Histomorphometric Changes in Tissue Architecture in Relation to Alteration in Fixation Protocol—An Invitro Study', J Clin Diagn Res, 10: ZC28-32.

Tanimoto, A., J. Nakashima, H. Kohno, H. Shinmoto, and S. Kuribayashi. 2007. 'Prostate cancer screening: the clinical value of diffusion-weighted imaging and dynamic MR imaging in combination with T2-weighted imaging', J Magn Reson Imaging, 25: 146-52.

Theiss, A. P., D. Chafin, D. R. Bauer, T. M. Grogan, and G. S. Baird. 2014. 'Immunohistochemistry of colorectal cancer biomarker phosphorylation requires controlled tissue fixation', PLoS One, 9: el 13608.

Uhl M., Altehoefer C., Kontny U., Il'yasov, K., Buchert M., Langer M. 2014. 'MRI-diffusion imaging of neuroblastomas: first results and correlation', European Radiology.

Additional Embodiments

Hine (Stain Technol. 1981 March; 56(2):119-23) discloses a method of staining whole tissue blocks by immersing a tissue sample in a hematoxylin solution and eosin solution after fixation and prior to embedding and sectioning. Additionally, fixation is frequently performed by immersing an unfixed tissue sample into a volume of fixative solution, and the fixative solution is allowed to diffuse into the tissue sample. As demonstrated by Chafin et al., (PLoS ONE 8(1): e54138. doi:10.1371/journal.pone. 0054138 (2013)), a failure to ensure that a fixative has sufficiently diffused into the tissue can compromise the integrity of the tissue sample. Thus, in one embodiment, the present systems and methods are applied to determine a sufficient time of diffusion of a fixative into a tissue sample prior to downstream process, e.g., staining with a counterstain (such as hematoxylin and eosin) and or labeling one or more biomarkers).

In some embodiments the present systems and methods are used to run a two-temperature immersion fixation method on a tissue sample. As used herein, a "two-temperature fixation method" is a fixation method in which tissue is first immersed in cold fixative solution for a first period of time, followed by heating the tissue for the second period of time. The cold step permits the fixative solution to diffuse throughout the tissue without substantially causing cross-linking. Then, once the tissue has adequately diffused throughout the tissue, the heating step leads to cross-linking by the fixative. The combination of a cold diffusion followed by a heating step leads to a tissue sample that is more completely fixed than by using standard methods. Thus, in some embodiments, a tissue sample is fixed by: (1) immersing an unfixed tissue sample in a cold fixative solution and monitoring diffusion of the fixative into the tissue sample by monitoring TOF in the tissue sample using the systems and methods as disclosed herein (diffusion step); and (2) allowing the temperature of the tissue sample to raise after a threshold TOF has been measured (fixation step).

Additional Embodiment 1. A method of estimating a time in which a fluid will optimally be diffused into a biological specimen immersed in the fluid, comprising:

(a) acquiring acoustic data at one or more positions along the biological specimen immersed in the fluid;

(b) deriving time-of-flight (TOF) data from the acquired acoustic data, wherein the derived TOF data comprises one or more computed TOF data points, one or more computed TOF curves, and/or one or more computed decay constants;

(c) simultaneously computing at least two confidence models based on the derived TOF data, wherein the at least two confidence models comprise a past confidence model, a present confidence model, and a future confidence model;

(d) determining a point in time when the computed at least two confidence models each independently meet predetermined threshold criteria; and (e) estimating the time in which the fluid will optimally be diffused into the biological specimen based on TOF data corresponding to the determined point in time when the computed at least two of confidence models each independently met the predetermined threshold criteria.

Additional Embodiment 2. The method of additional embodiment 1, wherein the fluid comprises one or more fixatives.

Additional Embodiment 3. The method of additional embodiment 2, wherein the one or more fixatives are aldehyde-based fixatives.

Additional Embodiment 4. The method of additional embodiment 2, wherein the fluid is selected from the group consisting of ethanol, xylene, and paraffin.

Additional Embodiment 5. The method of additional embodiment 1, wherein the computed at least two confidence models include the past confidence model and the present confidence model.

Additional Embodiment 6. The method of additional embodiment 1, wherein the computed at least two confidence models include each of the past confidence model, the present confidence model, and the future confidence model.

Additional Embodiment 7. The method of any one of the preceding additional embodiments, wherein the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant.

Additional Embodiment 8. The method of additional embodiment 7, wherein the determination of whether the predetermined number of retrieved computed candidate decay constants are within the predetermined threshold percentage value of the calculated average decay constant comprises performing convergence testing.

Additional Embodiment 9. The method of additional embodiment 8, wherein the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value.

Additional Embodiment 10. The method of additional embodiment 9, wherein the average decay constant is derived by: (i) retrieving a computed a decay constant for each of a predetermined number of TOF data points preceding the candidate TOF data point; and (ii) averaging each of the retrieved computed decay constants.

Additional Embodiment 11. The method of additional embodiment 10, wherein the predetermined number of TOF data points preceding the candidate TOF data point is at least about 3.

Additional Embodiment 12. The method of additional embodiment 9, wherein the predetermined threshold percentage value is less than about 5%.

Additional Embodiment 13. The method of additional embodiment 9, wherein the predetermined threshold percentage value is less than about 2.5%.

Additional Embodiment 14. The method of any one of the preceding additional embodiments, wherein the computed present confidence model meets predetermined present confidence model threshold criteria when a calculated present confidence interval is below a predetermined present confidence model threshold value.

Additional Embodiment 15. The method of additional embodiment 14, wherein the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

Additional Embodiment 16. The method of any one of the preceding additional embodiments, wherein the computed future confidence model meets predetermined future confidence model threshold criteria when a calculated future confidence interval is below a predetermined future confidence model threshold value.

Additional Embodiment 17. The method of additional embodiment 16, wherein the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

Additional Embodiment 18. The method of any one of the preceding additional embodiments, further comprising staining the biological specimen for the presence of at least one biomarker.

Additional Embodiment 19. The method of additional embodiment 18, wherein the at least one biomarker is a cancer biomarker.

Additional Embodiment 20. The method of additional embodiment 18, further comprising scoring the biological specimen stained for the presence of the at least one biomarker.

Additional Embodiment 21. The method of any one of the preceding additional embodiments, further comprising staining the biological specimen for the presence of at least two biomarkers.

Additional Embodiment 22. A method of predicting a time to fixation completion of a biological specimen immersed in one or more fixatives, comprising:
(a) acquiring acoustic data at one or more positions along the biological specimen immersed in the one or more fixatives (401);
(b) deriving time-of-flight (TOF) data from the acquired acoustic data, wherein the derived TOF data comprises one or more computed TOF data points, one or more computed TOF curves, and/or one or more computed decay constants (402);
(c) simultaneously computing at least two confidence models based on the derived TOF data, wherein the at least two confidence models comprise a past confidence model, a present confidence model, and a future confidence model (403);
(d) determine a point in time when the computed at least two confidence models each independently meet predetermined threshold criteria (404); and
(e) predicting the time to fixation completion based on TOF data corresponding to the determined point in time when the computed at least two of confidence models each independently met the predetermined threshold criteria (405).

Additional Embodiment 23. The method of additional embodiment 22, wherein the biological specimen is first immersed in one or more fixatives at a temperature below about 15° C.

Additional Embodiment 24. The method of any one of additional embodiments 22 and 23, wherein the acoustic data is acquired after the one or more fixatives are warmed to the temperature of greater than about 15° C.

Additional Embodiment 25. The method of any one of additional embodiments 22 and 23, wherein the acoustic data is acquired after the one or more fixatives are warmed to the temperature of greater than about 25° C.

Additional Embodiment 26. The method of any one of additional embodiments 22-25, wherein the computed at least two confidence models include the past confidence model and the present confidence model.

Additional Embodiment 27. The method of any one of additional embodiments 22-25, wherein the computed at least two confidence models include each of the past confidence model, the present confidence model, and the future confidence model.

Additional Embodiment 28. A non-transitory computer-readable medium storing instructions for estimating a time in which a fluid will optimally be diffused into a biological specimen immersed in the fluid comprising:

a. deriving time-of-flight (TOF) data from acquired acoustic data;

b. simultaneously computing at least two confidence models based on the derived TOF data, wherein the at least two confidence models comprise a past confidence model, a present confidence model, and a future confidence model;

c. determining a point in time when the computed at least two confidence models each independently meet predetermined threshold criteria; and d. estimating the time in which the fluid will optimally be diffused into the biological specimen based on TOF data corresponding to the determined point in time when the computed at least two of confidence models each independently met the predetermined threshold criteria.

Additional Embodiment 29. The non-transitory computer-readable medium of additional embodiment 28, further comprising instructions for computing one or more decay constants.

Additional Embodiment 30. The non-transitory computer-readable medium of any one of additional embodiments 28-29, further comprising instructions for performing convergence testing.

Additional Embodiment 31. The non-transitory computer-readable medium of additional embodiment 30, wherein the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value.

Additional Embodiment 32. A non-transitory computer-readable medium storing instructions for determining a point in time when at least two confidence models each independently meet predetermined threshold criteria comprising: (a) deriving TOF data from acoustic data acquired of a biological specimen immersed in a fluid; (b) continuously computing a past confidence model, a present confidence model, and a future confidence model until each of the past, present, and future confidence models simultaneously and independently meet predetermined threshold criteria; and (c) identifying the point in time corresponding to the derived TOF data at which the past, present, and future confidence models were simultaneously and independently satisfied.

Additional Embodiment 33. The non-transitory computer-readable medium of additional embodiment 32, wherein the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant.

Additional Embodiment 34. The non-transitory computer-readable medium of additional embodiment 33, wherein the determination of whether the predetermined number of retrieved computed candidate decay constants are within the predetermined threshold percentage value of the calculated average decay constant comprises performing convergence testing.

Additional Embodiment 35. The non-transitory computer-readable medium of additional embodiment 34, wherein the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value.

Additional Embodiment 36. The non-transitory computer-readable medium of additional embodiment 35, wherein the average decay constant is derived by: (i) retrieving a computed a decay constant for each of a predetermined number of TOF data points preceding the candidate TOF data point; and (ii) averaging each of the retrieved computed decay constants.

Additional Embodiment 37. The non-transitory computer-readable medium of any one of additional embodiments 32-36, wherein the computed present confidence model meets predetermined present confidence model threshold criteria when a calculated present confidence interval is below a predetermined present confidence model threshold value.

Additional Embodiment 38. The non-transitory computer-readable medium of additional embodiment 37, wherein the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

Additional Embodiment 39. The non-transitory computer-readable medium of any one of additional embodiments 32-38, wherein the computed future confidence model meets predetermined future confidence model threshold criteria when a calculated future confidence interval is below a predetermined future confidence model threshold value.

Additional Embodiment 40. The non-transitory computer-readable medium of additional embodiment 39, wherein the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

Additional Embodiment 41. The non-transitory computer-readable medium of any one of additional embodiments 32-40, further comprising instructions for estimate a time in which the fluid is optimally diffused into the biological specimen.

Additional Embodiment 42. The non-transitory computer-readable medium of additional embodiment 41, wherein the fluid comprises one or more fixatives.

Additional Embodiment 43. The non-transitory computer-readable medium of additional embodiment 41, wherein the fluid is selected from the group consisting of ethanol, xylene, and paraffin.

Additional Embodiment 44. A system (200) for estimating a time in which a fluid will optimally be diffused into a biological specimen immersed in the fluid, the system comprising: (i) one or more processors (206), and (ii) one or more memories (205) coupled to the one or more processors (206), the one or more memories (205) to store computer-executable instructions that, when executed by the one or more processors (206), cause the system (200) to perform operations comprising:

(a) deriving time-of-flight (TOF) data from acoustic data acquired at one or more positions along a biological specimen immersed in a fluid;

(b) simultaneously computing at least two confidence models based on the derived TOF data, wherein the at least two confidence models comprise a past confidence model, a present confidence model, and a future confidence model;

(c) determining a point in time when the computed at least two confidence models each independently meet predetermined threshold criteria; and (d) estimating the time in which the fluid will optimally be diffused into the biological specimen based on TOF data corresponding to the determined point in time when the computed at least two of confidence models each independently met the predetermined threshold criteria.

Additional Embodiment 45. The system of additional embodiment 44, wherein the fluid comprises one or more fixatives.

Additional Embodiment 46. The system of additional embodiment 44, wherein the fluid is selected from the group consisting of ethanol, xylene, and paraffin.

Additional Embodiment 47. A method of estimating a time in which one or more fixatives will optimally be diffused into a biological specimen immersed in the fluid, comprising:

(a) immersing the biological specimen in the one or more fixatives, wherein the one or more fixatives are maintained at a temperature of less than about 15° C.

(b) acquiring acoustic data at one or more positions along the biological specimen immersed in the fluid (401);

(c) deriving time-of-flight (TOF) data from the acquired acoustic data, wherein the derived TOF data comprises one or more computed TOF data points, one or more computed TOF curves, and/or one or more computed decay constants (402);

(d) simultaneously computing at least two confidence models based on the derived TOF data, wherein the at least two confidence models comprise a past confidence model, a present confidence model, and a future confidence model (403);

(e) determining a point in time when the computed at least two confidence models each independently meet predetermined threshold criteria (404); and (f) estimating the time in which the fluid will optimally be diffused into the biological specimen based on TOF data corresponding to the determined point in time when the computed at least two of confidence models each independently met the predetermined threshold criteria (405).

Additional Embodiment 48. The method of additional embodiment 47, wherein the temperature is less than about 10° C.

Additional Embodiment 49. The method of additional embodiment 47, wherein the temperature ranges from about −10° C. to about 10° C.

Additional Embodiment 50. The method of additional embodiment 47, wherein the temperature ranges from about −4° C. to about 4° C.

Additional Embodiment 51. A method of predicting a time to fixation completion of a biological specimen immersed in one or more fixatives, comprising:

(a) immersing the biological specimen in the one or more fixatives, wherein the one or more fixatives are maintained at a temperature of greater than about 20° C.;

(b) acquiring acoustic data at one or more positions along the biological specimen immersed in the one or more fixatives;

(c) deriving time-of-flight (TOF) data from the acquired acoustic data, wherein the derived TOF data comprises one or more computed TOF data points, one or more computed TOF curves, and/or one or more computed decay constants;

(d) simultaneously computing at least two confidence models based on the derived TOF data, wherein the at least two confidence models comprise a past confidence model, a present confidence model, and a future confidence model;

(e) determine a point in time when the computed at least two confidence models each independently meet predetermined threshold criteria; and (f) predicting the time to fixation completion based on TOF data corresponding to the determined point in time when the computed at least two of confidence models each independently met the predetermined threshold criteria.

Additional Embodiment 52. The method of additional embodiment 51, wherein the temperature is greater than about 25° C.

Additional Embodiment 53. The method of additional embodiment 51, wherein the temperature is greater than about 30° C.

Additional Embodiment 54. The method of additional embodiment 51, wherein the temperature is greater than about 35° C.

Additional Embodiment 55. The method of additional embodiment 51, wherein the temperature is greater than about 40° C.

Additional Embodiment 56. The method of additional embodiment 51, wherein the temperature is greater than about 45° C.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method of estimating a time in which a fluid will optimally be diffused into a biological specimen immersed in the fluid, comprising:
   (a) acquiring acoustic data at one or more positions along the biological specimen immersed in the fluid;
   (b) deriving time-of-flight (TOF) data from the acquired acoustic data, wherein the derived TOF data comprises one or more computed TOF data points, one or more computed TOF curves, and/or one or more computed decay constants;
   (c) simultaneously computing at least two confidence models based on the derived TOF data, wherein the at least two confidence models are selected from a past confidence model, a present confidence model, and a future confidence model;
   (d) determining a point in time when the computed at least two confidence models each independently meet predetermined threshold criteria; and
   (e) estimating the time in which the fluid will optimally be diffused into the biological specimen based on TOF data corresponding to the determined point in time when the computed at least two of confidence models each independently met the predetermined threshold criteria.

2. The method of claim 1, wherein the fluid comprises one or more fixatives.

3. The method of claim 2, wherein the fluid is selected from the group consisting of ethanol, xylene, and paraffin.

4. The method of claim 1, wherein the computed at least two confidence models include the past confidence model and the present confidence model.

5. The method of claim 1, wherein the computed confidence models include each of the past confidence model, the present confidence model, and the future confidence model.

6. The method of claim 1, wherein the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant.

7. The method of claim 6, wherein the determination of whether the predetermined number of retrieved computed candidate decay constants are within the predetermined threshold percentage value of the calculated average decay constant comprises performing convergence testing.

8. The method of claim 7, wherein the performing of the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value.

9. The method of claim 8, wherein the average decay constant is derived by: (i) retrieving a computed a-decay constant for each of a predetermined number of TOF data points preceding the candidate TOF data point; and (ii) averaging each of the retrieved computed decay constants.

10. The method of claim 9, wherein the predetermined number of TOF data points preceding the candidate TOF data point is at least about 3.

11. The method of claim 8, wherein the predetermined threshold percentage value is less than about 5%.

12. The method of claim 1, wherein the computed present confidence model meets predetermined present confidence model threshold criteria when a calculated present confidence interval is below a predetermined present confidence model threshold value.

13. The method of claim 12, wherein the present confidence interval is calculated by (a) performing a non-linear regression fit of a TOF curve using some or all of the computed TOF data points of the computed TOF curve; and (b) determining the confidence interval of a retrieved computed decay constant based on the performed non-linear regression fitting.

14. The method of claim 1, wherein the computed future confidence model meets predetermined future confidence model threshold criteria when a calculated future confidence interval is below a predetermined future confidence model threshold value.

15. The method of claim 14, wherein the future confidence interval is calculated by (a) performing a non-linear regression fit of a TOF curve using all of the computed TOF data points of the computed TOF curve; (b) determining the confidence interval of a retrieved computed decay constant based on the performed non-linear regression fitting from time zero to a future point in time; and (c) calculating an average confidence interval of the TOF curve.

16. A non-transitory computer-readable medium storing instructions for estimating a time in which a fluid will optimally be diffused into a biological specimen immersed in the fluid comprising:
   a. deriving time-of-flight (TOF) data from acquired acoustic data;
   b. simultaneously computing at least two confidence models based on the derived TOF data, wherein the at least two confidence models comprise a past confidence model, a present confidence model, and a future confidence model;
   c. determining a point in time when the computed at least two confidence models each independently meet predetermined threshold criteria; and
   d. estimating the time in which the fluid will optimally be diffused into the biological specimen based on TOF data corresponding to the determined point in time when the computed at least two confidence models each independently met the predetermined threshold criteria,
      wherein the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant.

17. The non-transitory computer-readable medium of claim 16, further comprising instructions for computing one or more decay constants.

18. The non-transitory computer-readable medium of claim 16, further comprising instructions for performing convergence testing.

19. The non-transitory computer-readable medium of claim 18, wherein the convergence testing comprises (i) computing a candidate decay constant of a candidate computed TOF data point to provide a theoretical value; (ii) calculating an average decay constant based on a predetermined number of computed decay constants corresponding to a predetermined number of TOF data points computed over time and preceding the candidate TOF data point to provide an experimental value; (iii) determining an actual percent error based on the computed theoretical value and the calculated experimental value; and (iv) comparing the determined percent error to a predetermined threshold percentage value.

20. A system for estimating a time in which a fluid will optimally be diffused into a biological specimen immersed in the fluid, the system comprising: (i) one or more processors, and (ii) one or more memories coupled to the one or more processors, the one or more memories to store computer-executable instructions that, when executed by the one or more processors, cause the system to perform operations comprising:

(a) deriving time-of-flight (TOF) data from acoustic data acquired at one or more positions along a biological specimen immersed in a fluid;

(b) simultaneously computing at least two confidence models based on the derived TOF data, wherein the at least two confidence models comprise a past confidence model, a present confidence model, and a future confidence model;

(c) determining a point in time when the computed at least two confidence models each independently meet predetermined threshold criteria; and (d) estimating the time in which the fluid will optimally be diffused into the biological specimen based on TOF data corresponding to the determined point in time when the computed at least two of confidence models each independently met the predetermined threshold criteria, wherein the computed past confidence model meets predetermined past confidence model threshold criteria when a predetermined number of retrieved computed candidate decay constants corresponding to a plurality of derived TOF data points are each determined to be within a predetermined threshold percentage value of a calculated average decay constant.

\*   \*   \*   \*   \*